(12) United States Patent
LaMont et al.

(10) Patent No.: US 12,285,034 B2
(45) Date of Patent: Apr. 29, 2025

(54) HUMAN AND NON-HUMAN ANIMAL USE OF MICROBIAL ANAPLEROTIC OIL

(71) Applicant: HELIAE DEVELOPMENT, LLC, Gilbert, AZ (US)

(72) Inventors: Micheal LaMont, Gilbert, AZ (US); Magdalena Amezquita Ernult, Phoenix, AZ (US); Eneko Ganuza Taberna, Tempe, AZ (US)

(73) Assignee: HELIAE DEVELOPMENT, LLC, Gilbert, AZ (US)

(*) Notice: Subject to any disclaimer, the term of this patent is extended or adjusted under 35 U.S.C. 154(b) by 0 days.

(21) Appl. No.: 18/364,153

(22) Filed: Aug. 2, 2023

(65) Prior Publication Data

US 2023/0397642 A1    Dec. 14, 2023

Related U.S. Application Data

(63) Continuation of application No. 17/818,772, filed on Aug. 10, 2022, now Pat. No. 11,758,934, which is a continuation of application No. 17/240,667, filed on Apr. 26, 2021, now Pat. No. 11,457,655, which is a continuation of application No. 17/090,589, filed on Nov. 5, 2020, now Pat. No. 10,986,856, which is a
(Continued)

(51) Int. Cl.
| | |
|---|---|
| A23L 29/00 | (2016.01) |
| C12N 1/12 | (2006.01) |
| C12P 7/6409 | (2022.01) |
| C12R 1/89 | (2006.01) |

(52) U.S. Cl.
CPC ............. *A23L 29/04* (2016.08); *C12N 1/12* (2013.01); *C12N 1/125* (2021.05); *C12P 7/6409* (2013.01); *C12R 2001/89* (2021.05)

(58) Field of Classification Search
CPC ....................................................... A23L 29/04
See application file for complete search history.

(56) References Cited

U.S. PATENT DOCUMENTS

| | | | |
|---|---|---|---|
| 8,399,515 | B2 | 3/2013 | Roe |
| 9,662,306 | B2 | 5/2017 | Venn-Watson |

(Continued)

FOREIGN PATENT DOCUMENTS

| | | |
|---|---|---|
| CN | 106916856 A | 7/2017 |
| JP | 2017063633 A | 4/2017 |

(Continued)

OTHER PUBLICATIONS

Henry et al., "Antioxidant and cyclooxygenase activities of fatty acids found in food," J Agric Food Chem 50:2231-2234, 2002.*
(Continued)

*Primary Examiner* — Rosanne Kosson
(74) *Attorney, Agent, or Firm* — Timothy M. Shropshire

(57) ABSTRACT

Disclosed are techniques and systems for producing microbials having anaplerotic oils that are rich in odd-chain fatty acids, and other beneficial components, at higher concentrations than those present in other natural dietary sources of OCFA, at lower cost, and higher production yield. Further, disclosed are examples of incorporation of these higher concentration OCFA products into food for human and non-human animal consumption.

20 Claims, 53 Drawing Sheets

Related U.S. Application Data continuation of application No. 16/720,972, filed on Dec. 19, 2019, now Pat. No. 10,874,131, which is a continuation-in-part of application No. 16/229,551, filed on Dec. 21, 2018, now Pat. No. 10,745,724.

(60) Provisional application No. 62/783,546, filed on Dec. 21, 2018, provisional application No. 62/731,476, filed on Sep. 14, 2018, provisional application No. 62/609,700, filed on Dec. 22, 2017.

(56) References Cited

U.S. PATENT DOCUMENTS

| | | | |
|---|---|---|---|
| 10,440,972 | B2 | 10/2019 | Ameye et al. |
| 10,745,724 | B2 | 8/2020 | Taberna et al. |
| 10,874,131 | B2 | 12/2020 | Micheal et al. |
| 10,986,856 | B2 | 4/2021 | Lamont et al. |
| 11,434,511 | B2 | 9/2022 | Ganuza Taberna et al. |
| 11,447,803 | B2 | 9/2022 | Ganuza Taberna et al. |
| 11,457,655 | B2 | 10/2022 | Lamont et al. |
| 11,758,934 | B2 | 9/2023 | Lamont et al. |
| 2010/0285105 | A1 | 11/2010 | Radianingtyas |
| 2014/0193867 | A1 | 7/2014 | San et al. |
| 2014/0329287 | A1 | 11/2014 | Blazeck et al. |
| 2015/0267145 | A1 | 9/2015 | Pottathil |
| 2016/0030375 | A1 | 2/2016 | Roe |
| 2019/0194702 | A1 | 6/2019 | Taberna et al. |
| 2020/0138074 | A1 | 5/2020 | Micheal et al. |
| 2020/0347418 | A1 | 11/2020 | Ganuza Taberna et al. |
| 2021/0051988 | A1 | 2/2021 | Lamont et al. |
| 2021/0054421 | A1 | 2/2021 | Ganuza Taberna et al. |
| 2021/0251270 | A1 | 8/2021 | Lamont et al. |
| 2022/0396814 | A1 | 12/2022 | Ganuza Taberna et al. |
| 2022/0400723 | A1 | 12/2022 | Lamont et al. |

FOREIGN PATENT DOCUMENTS

| | | |
|---|---|---|
| WO | WO-2006038063 A1 | 4/2006 |
| WO | WO-2014074769 A2 | 5/2014 |
| WO | WO-2016137897 A1 | 9/2016 |
| WO | WO-2018200837 A1 | 11/2018 |
| WO | WO-2018202852 A1 | 11/2018 |
| WO | WO-2019126652 A1 | 6/2019 |
| WO | WO-2020061445 A1 | 3/2020 |
| WO | WO-2020132285 A1 | 6/2020 |

OTHER PUBLICATIONS

English machine translation of Fengyi (Fengyi Biotechnology R & D Center Co. Ltd.), CN 106916856 A, 2017.*
Adlercreutz et al., "Enzyme-catalysed lipid modification". Biotechnology and Genetic Engineering Reviews. Dec. 1, 1994;12(1):231-54.
Bellou et al., "Microbial oils as food additives: recent approaches for improving microbial oil production and its polyunsaturated fatty acid content," Current Opinion in Biotechnology, Sep. 29, 2015, vol. 37, pp. 24-35.
Borges, K. et al., "Triheptanoin—a medium chain triglyceride with odd chain fatty acids: A new anaplerotic anticonvulsant treatment?", Epilepsy Research, 100(3): 239-244 (2011).
Buchhaupt, et al., "Chapter 37—Biotechnologal Production of Fatty Aldehydes". Flavour Science, 5 pages, (Elsevier Inc., 2014).
Chandra, et al. "Lipid metabolism in response to individual short chain fatty acids during mixotrophic mode of microalgal cultivation: Influence of biodiesel saturation and protein profile", Bioresouce Technology 188, (2015), pp. 169-176.
Chang "New Australian thraustochytrids: A renewable Source of Biofuels, Omega-3 Oils and Bioproducts", Ph. Thesis, University of Tasmania, Aug. 2013, 199 pages.
Chaung et al., "Effect of culture conditions on growth, lipid content, and fatty acid composition of Aurantiochytrium mangrovei strain BL10", AMB Express, vol. 2, No. 42, 2012, pp. 1-11.
Emmanuel "The Relative Contribution of Propionate, and Long-chain Even-numbered Fatty Acids to the Production of Long-chain Odd-numbered Fatty Acids in Rumen Bacteria", Biochimica et Biophysica Acta, vol. 528, 1978, pp. 239-246.
Extended European Search Report for European Application No. 19898607.7 mailed Dec. 9, 2021, 12 pages.
Fan et al., "Differentiation in fatty acid profiles of pigmented and nonpigmented Aurantiochytrium isolated from Hong Kong mangroves". J Agric Food Chem. Jul. 22, 2009;57(14):6334-41.
Fan et al., "Eicosapentaenoic and docosahexaenoic acids production by okra-utilizing potention of thraustrochyrtirds", J Ind Microbio Biotechnol. 2001; Jun. 27: 199-202.
Forouhi et al., "Differences in the prospective association between individual plasma phospholipid saturated fatty acids and incident type 2 diabetes: the EPIC-InterAct case-cohort study". Lancet Diabetes Endocrinol. Oct. 2014;2(10):810-8.
Hamberg et al., "α-Oxidation of fatty acids in higher plants". J. Biol. Chem. 1999;274: 11 pages.
International Search Report and Written Opinion for PCT Application No. PCT/US2018/067104 mailed Apr. 10, 2019, 14 pages.
International Search Report and Written Opinion for PCT Application No. PCT/US2019/067551 mailed Feb. 25, 2020, 7 pages.
Jenkins et al., "A review of odd-chain fatty acid metabolism and the role of pentadecanoic acid (C15: 0) and heptadecanoic acid (C17: 0) in health and disease". Molecules. Jan. 30, 2015;20(2):2425-44.
Kaya et al., "On the function of pentdecanoic acid and docosahexaenoic acid during culturing of the thraustochytrid, *Aurantiochytrium* sp. NB6-3", Journal of Biochemical & Microbial Technology, 2015, 3[1]:1-7.
Mochel et al., "Pyruvate carboxylase deficiency: clinical and biochemical response to anaplerotic diet therapy," Molecular Genetics and Metabolism, 84:305-312 (2005).
Ochsenreither et al., "Production strategies and applications of microbial single cell oils". Frontiers in microbiology. Oct. 5, 2016;7: 26 pages.
Otto et al., "Dietary intake of saturated fat by food source and incident cardiovascular disease: the Multi-Ethnic Study of Atherosclerosis". Am J Clin Nutr. Aug. 2012;96(2):397-404.
Paoli, et al, "Beyond weight loss; a review of the therapeutic uses of very low-carbohydrate (Ketogenic) diets". European Hournal of Clinical Nutriton, 2013 67(8), 789-796.
Park et al., "Anaplerotic triheptanoin diet enhances mitochondrial substrate use to remodel the metabolome and improve lifespan, motor function, and sociability in MeCP2-null mice". PLoS One. Oct. 9, 2014;9(10): 22 pages.
Park et al., "Optimization of odd chain fatty acid production by Yarrowia lipolytica". Biotechnol Biofuels. 2018; 11(158); 1-12.
Philipson et al., "When BAD is good for beta cells". Cell Metab. Apr. 2008;7(4):280-1.
Rezanaka, et al, "Odd-numbered very-long chain fatty acids from the microbial, animal and plant kingdoms", Progress in Lipid Research (2009), 48(3-4), 206-238.
Roe et al., "Anaplerotic diet therapy in inherited metabolic disease: therapeutic potential," Journal of Inherited Metabolic Disease, 29:332-340 (Apr.-Jun. 2006).
Roe et al., "Treatment of cardiomyopathy and rhabdomyolysis in long-chain fat oxidation disorders using an anaplerotic odd-chain triglyceride," Journal of Clinical Investigation, 110(2):259-269 (Jul. 2002).
Roe et al., "Adult Polyglucosan Body Disease (APBD): Anaplerotic diet therapy (Triheptanoin) and demonstration of defective methylation pathways". Mol Genet Metab. Oct.-Nov. 2010;101(2-3):246-52.
Santaren et al., Serum pentadecanoic acid (15:0), a short-term marker of dairy food intake, is inversely associated with incident type 2 diabetes and its underlying disorders. Am J Clin Nutr. Dec. 2014;100(6):1532-40.
Schneider et al. "Waxmonester fermentation in Euglena gracilis T. Factors favouring the Synthesis of odd-numbered fatty acids and alcohols", Planta (1985) 166:67-73.
Shine et al., "Fat Metabolism in Higher Plants Recent Studies on Plant a-Oxidation Systems" Arch Biochem. Biophys 147-157 (1974).
Song et al., "Different Impacts of Short-Chain Fatty Acids on Saturated and Polyunsaturated Fatty Acid Biosynthesis in

(56) References Cited

OTHER PUBLICATIONS

*Aurantiochytrium* sp. SD 116", Journal of Agricultural and Food Chemistry, Sep. 23, 2013, vol. 61, pp. 9876-9881.
Taberna "Heterotrophic cultivation of microalgae as a source of docosahexaenoic acid for aquaculture (Doctoral dissertation)", Universidad de Las Palmas De Gran Canaria, 2008, 203 pages.
Takahashi et al., "Alpha-Oxidation of Fatty acids in Fasted or diabetic rats", Diabets Res. Clin Pract. 16, 103-108 (1992).
Weitkunat et al., "Odd-Chain Fatty Acids as a Biomarker for Dietary Fiber Intake: A Novel Pathway for Endogenous Production from Propionate", The American Journal of Clinical Nutrion (2017) 105(6), 8 pages.
Wikipedia "Euglena gracilis", retrieved on Oct. 3, 2024, 4 pages.
Wikipedia "Microalgae", retrieved on Oct. 3, 2024, 5 pages.
Yokoyama et al. Taxonomic rearrangement of the genus Schizochytrium sensu lato based on morphology, chemotaxonomic characteristics, and 18S rRNA gene phylogeny (Thrausochytriaceae, Labyrinthulomycetes): emendation for Schizochytrium and erection of Aurantiochytrium and *Oblongichytrium* gen. nov. Mycoscience (2007) 48:199-211.
Zhao et al., "Analysis of the biosynthetic process of fatty acids in Thraustochytrium", Biochimie, Oct. 31, 2017, vol. 144, pp. 108-114.
Zhu, et al., "Changes of Lipid content and fatty acid compostions of Schizochytrium limacinum in response to different temperatures and salinities". Process Biochemistry, 42(2), 210-214, 2007.

\* cited by examiner

| Time (h) | 0 | 8 | 16 | 24 | 32 | 40 | 48 | 56 | 64 | 72 | 74 |
|---|---|---|---|---|---|---|---|---|---|---|---|
| Total Lipids (% DW) | | | 7.0 ± 1.4 | 32.5 ± 0.7 | 32.5 ± 0.7 | 49.0 ± 9.9 | 52.5 ± 4.9 | 53.0 ± 15.6 | 58.0 ± 8.5 | 58.0 | 53.0 |
| Protein (% DW) | | | | | | | | | | | 10.0 |
| Total Fatty Acids (% DW) | 32.4 ± 5.8 | 10.2 ± 1.1 | 6.8 ± 0.7 | 31.0 ± 2.1 | 27.7 ± 6.6 | 45.2 ± 10.0 | 49.8 ± 5.6 | 49.3 ± 15.5 | 51.3 ± 7.4 | 56.5 | 46.5 |
| Fatty Acid Profile (% TFA) | | | | | | | | | | | |
| 13:0 | 0.0 ± 0.0 | 0.0 ± 0.0 | 0.0 ± 0.0 | 0.1 ± 0.2 | 0.9 ± 0.1 | 1.3 ± 0.1 | 1.4 ± 0.2 | 1.4 ± 0.3 | 1.3 ± 0.3 | 1.1 | 1.1 |
| 14:0 | 2.3 ± 0.1 | 2.6 ± 0.1 | 0.7 ± 1.0 | 2.8 ± 0.1 | 2.3 ± 0.2 | 2.1 ± 0.2 | 1.9 ± 0.3 | 1.9 ± 0.1 | 1.7 ± 0.2 | 1.8 | 1.8 |
| 15:0 | 0.0 ± 0.0 | 0.0 ± 0.0 | 0.0 ± 0.0 | 7.8 ± 0.7 | 25.4 ± 0.4 | 32.6 ± 0.3 | 37.6 ± 3.0 | 37.2 ± 0.8 | 38.7 ± 2.6 | 36.9 | 36.9 |
| 16:0 | 50.6 ± 3.3 | 58.8 ± 1.8 | 37.6 ± 1.4 | 46.1 ± 0.2 | 32.7 ± 1.2 | 26.1 ± 0.5 | 20.9 ± 3.0 | 21.1 ± 0.2 | 19.0 ± 1.9 | 19.9 | 20.0 |
| 17:0 | 0.0 ± 0.0 | 0.0 ± 0.0 | 0.0 ± 0.0 | 2.0 ± 0.1 | 4.9 ± 0.6 | 5.6 ± 0.5 | 6.5 ± 0.6 | 6.6 ± 0.3 | 7.3 ± 0.1 | 7.6 | 7.8 |
| 18:0 | 2.0 ± 0.3 | 2.1 ± 0.1 | 0.5 ± 0.7 | 1.2 ± 0.0 | 0.9 ± 0.0 | 0.7 ± 0.0 | 0.6 ± 0.0 | 0.6 ± 0.0 | 0.5 ± 0.0 | 0.5 | 0.5 |
| 22:5 (n-6) | 8.7 ± 0.2 | 6.2 ± 0.6 | 10.0 ± 0.6 | 6.8 ± 0.3 | 5.2 ± 0.1 | 4.8 ± 0.1 | 4.8 ± 0.1 | 4.9 ± 0.3 | 5.0 ± 0.4 | 5.3 | 5.3 |
| 22:6 (n-3) | 35.0 ± 3.5 | 25.3 ± 2.2 | 48.4 ± 2.3 | 32.2 ± 1.0 | 26.1 ± 1.1 | 25.0 ± 0.1 | 25.0 ± 0.2 | 25.5 ± 0.2 | 25.4 ± 0.4 | 25.9 | 25.8 |
| Other FA | 1.5 ± 0.2 | 5.1 ± 1.0 | 2.8 ± 0.2 | 1.1 ± 0.6 | 1.6 ± 0.0 | 1.8 ± 0.1 | 1.3 ± 0.6 | 1.0 ± 0.1 | 1.0 ± 0.0 | 1.0 | 0.9 |
| DHA (% DW) | 11.4 ± 3.2 | 2.6 ± 0.5 | 3.3 ± 0.2 | 10.0 ± 0.4 | 7.2 ± 1.4 | 11.3 ± 2.6 | 12.4 ± 1.3 | 12.6 ± 4.0 | 13.1 ± 2.1 | 14.6 | 12.0 |
| OCFA (% TFA) | 0.0 ± 0.0 | 0.0 ± 0.0 | 0.0 ± 0.0 | 9.9 ± 0.9 | 31.2 ± 0.1 | 39.5 ± 0.8 | 45.5 ± 3.8 | 45.2 ± 0.8 | 47.3 ± 2.9 | 45.7 | 45.7 |

Table 24 – Total lipids and Fatty Acid profile from 1000 L pilot *Aurantiochytrium acetophilum* HS399 odd chain fatty acid fermentation.

FIGURE 48

| | Propionate | Pentanoate | Heptanoate | Yeast extract | Proteose peptone | Methionine | Valine | Isoleucine |
|---|---|---|---|---|---|---|---|---|
| Promoter Concentration (g/L) | 6 | 6 | 6 | 30 | 30 | 8 | 8 | 8 |
| Final Cell Dry Weight (g/L) | 33.1 ± 0.28 | 32.1 ± 0.39 | 27.6 ± 0.46 | 41.56 ± 0.40 | 42.34 ± 0.19 | 23.55 ± 2.19 | 29.89 ± 1.14 | 24.15 ± 0.61 |
| Harvest time (h) | 96 | 96 | 96 | 120 | 120 | 102 | 102 | 102 |
| Total Lipids (% DW) | 71.0 ± 0.0 | 74.0 ± 1.4 | 66.3 ± 0.4 | 55.0 ± 1.0 | 57.0 ± 0.0 | 64.0 ± 0.0 | 67.3 ± 0.6 | 69.5 ± 5.6 |
| Total Fatty Acids (% DW) | 57.3 ± 0.5 | 58.5 ± 1.3 | 53.5 ± 0.7 | 42.0 ± 2.8 | 48.1 ± 0.3 | 54.4 ± 0.1 | 54.0 ± 2.6 | 55.3 ± 2.6 |
| Fatty Acid Profile (% TFA) | | | | | | | | |
| 13:0 | 1.8 ± 0.0 | 1.0 ± 0.0 | 1.6 ± 0.2 | 0.0 ± 0.0 | 0.0 ± 0.0 | 0.0 ± 0.0 | 0.3 ± 0.0 | 1.1 ± 0.2 |
| 14:0 | 1.9 ± 0.0 | 1.6 ± 0.1 | 1.5 ± 0.2 | 3.0 ± 0.1 | 3.7 ± 0.1 | 2.9 ± 0.0 | 2.3 ± 0.1 | 2.1 ± 0.4 |
| 15:0 | 32.6 ± 0.5 | 37.2 ± 0.2 | 41.5 ± 3.4 | 4.0 ± 0.1 | 0.7 ± 0.0 | 0.8 ± 0.1 | 16.8 ± 0.3 | 28.4 ± 5.9 |
| 16:0 | 23.5 ± 0.4 | 15.2 ± 0.7 | 13.7 ± 3.5 | 39.9 ± 1.2 | 41.6 ± 0.1 | 52.3 ± 0.6 | 30.2 ± 0.6 | 23.6 ± 6.1 |
| 17:0 | 5.3 ± 0.2 | 8.2 ± 0.0 | 8.6 ± 0.8 | 1.3 ± 0.0 | 0.3 ± 0.0 | 0.4 ± 0.0 | 4.3 ± 0.1 | 5.0 ± 1.1 |
| 18:0 | 0.8 ± 0.0 | 0.4 ± 0.0 | 0.4 ± 0.1 | 1.5 ± 0.0 | 1.4 ± 0.0 | 1.5 ± 0.0 | 0.9 ± 0.0 | 0.7 ± 0.2 |
| 22:5 (n-6) | 5.3 ± 0.1 | 4.2 ± 0.0 | 4.2 ± 0.1 | 8.8 ± 0.2 | 9.1 ± 0.0 | 7.5 ± 0.0 | 7.4 ± 0.1 | 5.5 ± 0.3 |
| 22:6 (n-3) | 27.0 ± 0.2 | 29.8 ± 0.4 | 26.6 ± 0.4 | 39.4 ± 0.9 | 41.0 ± 0.0 | 33.5 ± 0.4 | 36.0 ± 0.3 | 31.8 ± 0.3 |
| Other FA | 1.6 ± 0.0 | 2.3 ± 0.2 | 1.8 ± 0.1 | 1.6 ± 0.4 | 2.2 ± 0.3 | 1.0 ± 0.2 | 1.4 ± 0.3 | 1.7 ± 0.0 |
| OCFA (%FA) | 39.9 ± 0.7 | 46.4 ± 0.1 | 51.9 ± 4.4 | 5.3 ± 0.2 | 1.1 ± 0.0 | 1.3 ± 0.1 | 21.4 ± 0.4 | 34.6 ± 7.4 |
| OCFA (%DW) | 22.9 ± 0.4 | 27.2 ± 0.7 | 27.7 ± 2.0 | 2.2 ± 0.1 | 0.5 ± 0.0 | 0.7 ± 0.1 | 11.6 ± 0.7 | 19.0 ± 3.1 |

Table 25 – List of OCFA Promotors.

FIGURE 54

Table 1. Fatty acids composition of vegetable oils [1].

| FAs [%] | SAF | GRP | SIL | HMP | SFL | WHG | PMS | SES | RB | ALM | RPS | PNT | OL | COC |
|---|---|---|---|---|---|---|---|---|---|---|---|---|---|---|
| C6:0 | nd | nd | nd | nd | nd | nd | nd | nd | nd | nd | nd | nd | nd | 0.32 |
| C8:0 | nd | 0.01 | nd | nd | nd | nd | nd | nd | nd | nd | nd | nd | nd | 7.6 |
| C10:0 | nd | nd | nd | nd | nd | nd | nd | nd | nd | 0.01 | nd | nd | nd | 5.5 |
| C12:0 | nd | 0.01 | 0.01 | nd | 0.02 | 0.07 | nd | nd | nd | 0.09 | nd | nd | nd | 47.7 |
| C14:0 | 0.10 | 0.05 | 0.09 | 0.07 | 0.09 | nd | 0.17 | nd | 0.39 | 0.07 | nd | 0.04 | nd | 19.9 |
| C15:0 | nd | 0.01 | 0.02 | nd | nd | 0.04 | nd | nd | nd | 0.02 | nd | nd | nd | nd |
| C16:0 | 6.7 | 6.6 | 7.9 | 6.4 | 6.2 | 17.4 | 13.1 | 9.7 | 20.0 | 6.8 | 4.6 | 7.5 | 16.5 | nd |
| C17:0 | 0.04 | 0.06 | 0.06 | 0.03 | 0.02 | 0.03 | 0.13 | nd | nd | 0.05 | 0.04 | 0.07 | nd | nd |
| C18:0 | 2.4 | 3.5 | 4.5 | 2.6 | 2.8 | 0.7 | 5.7 | 6.5 | 2.1 | 2.3 | 1.7 | 2.1 | 2.3 | 2.7 |
| C20:0 | nd | 0.16 | 2.6 | nd | 0.21 | nd | 0.47 | 0.63 | nd | 0.09 | nd | 1.01 | 0.43 | nd |
| C22:0 | nd | nd | nd | nd | nd | nd | nd | 0.14 | nd | nd | nd | nd | 0.15 | nd |
| C16:1 (n-7) | 0.08 | 0.08 | 0.05 | 0.11 | 0.12 | 0.21 | 0.12 | 0.11 | 0.19 | 0.53 | 0.21 | 0.07 | 1.8 | nd |
| C17:1 (n-7) | nd | nd | 0.03 | nd | nd | nd | nd | nd | nd | nd | nd | nd | nd | nd |
| C18:1cis (n-9) | 11.5 | 14.3 | 20.4 | 11.5 | 28.0 | 12.7 | 24.9 | 41.5 | 42.7 | 67.2 | 63.3 | 71.1 | 66.4 | 6.2 |
| C18:1trans (n-9) | nd | nd | nd | nd | nd | nd | nd | nd | nd | 0.14 | nd | nd | nd | nd |
| C20:1(n-9) | nd | 0.40 | 0.15 | 16.5 | 0.18 | 7.91 | 1.08 | 0.32 | 1.11 | 0.16 | 9.1 | nd | 0.30 | nd |
| C18:2cis (n-6) | 79.0 | 74.7 | 63.3 | 59.4 | 62.2 | 59.7 | 54.2 | 40.9 | 33.1 | 22.8 | 19.6 | 18.2 | 16.4 | 1.6 |
| C18:3 (n-3) | 0.15 | 0.15 | 0.88 | 0.36 | 0.16 | 1.2 | 0.12 | 0.21 | 0.45 | nd | 1.2 | nd | 1.6 | nd |
| C18:3 (n-6) | nd | nd | nd | 3.0 | nd | nd | nd | nd | nd | nd | nd | nd | nd | nd |
| SFAs | 9.3 | 10.4 | 15.1 | 9.2 | 9.4 | 18.2 | 19.6 | 16.9 | 22.5 | 9.3 | 6.3 | 10.7 | 19.4 | 92.1 |
| MUFAs | 11.6 | 14.8 | 20.7 | 28.1 | 28.3 | 20.9 | 26.1 | 42.0 | 44.0 | 67.9 | 72.8 | 71.1 | 68.2 | 6.2 |
| PUFAs | 79.1 | 74.9 | 64.2 | 62.8 | 62.4 | 61.0 | 54.3 | 41.2 | 33.6 | 22.8 | 20.9 | 18.2 | 18.0 | 1.6 |
| n-3 PUFAs | 0.2 | 0.2 | 0.9 | 0.4 | 0.2 | 1.2 | 0.1 | 0.2 | 0.5 | 0.0 | 1.2 | 0.0 | 1.6 | 0.0 |
| n-6 PUFAs | 79.0 | 74.7 | 63.3 | 62.4 | 62.2 | 59.7 | 54.2 | 40.9 | 33.1 | 22.8 | 19.6 | 18.2 | 16.4 | 1.6 |

[1] Data are expressed as percentages of total fatty acid methyl esters (FAMEs); nd means that FAs was not determined. Abbreviations of the samples mean: SAF—safflower, GRP—grape, SIL—*silybum marianum*, HMP—hemp, SFL—sunflower, WHG—wheat germ, PMS—pumpkin seed, SES—sesame, RB—rice bran, ALM—almond, RPS—rapeseed, PNT—peanut, OL—olive, and COC—coconut oils.

Table 26 – Fatty Acids Compositions of Vegetable Oils

FIGURE 55

HUMAN AND NON-HUMAN ANIMAL USE OF MICROBIAL ANAPLEROTIC OIL

CROSS-REFERENCE TO RELATED APPLICATIONS

This application is a continuation of U.S. patent application Ser. No. 17/818,772 (now U.S. Pat. No. 11,758,934, issued Sep. 19, 2023), filed Aug. 10, 2022, which is a continuation of U.S. patent application Ser. No. 17/240,667 (now U.S. Pat. No. 11,457,655, issued Oct. 4, 2022), filed Apr. 26, 2021, which is a continuation of U.S. patent application Ser. No. 17/090,589 (now U.S. Pat. No. 10,986,856, issued Apr. 27, 2021), filed Nov. 5, 2020, which is a continuation of U.S. patent application Ser. No. 16/720,972 (now U.S. Pat. No. 10,874,131, issued Dec. 29, 2020), filed Dec. 19, 2019, which claims priority to U.S. Provisional Patent Application No. 62/783,546, filed Dec. 21, 2018, and is a continuation-in-part of U.S. patent application Ser. No. 16/229,551 (now U.S. Pat. No. 10,745,724, issued Aug. 18, 2020), filed Dec. 21, 2018, which claims priority to U.S. Provisional Patent Application No. 62/731,476, filed Sep. 14, 2018, and U.S. Provisional Patent Application No. 62/609,700, filed Dec. 22, 2017.

FIELD OF THE INVENTION

The present invention generally relates to uses for microalgae oil rich in odd-chain fatty acid, and more specifically, to human and non-human animal uses of microbial anaplerotic oil.

BACKGROUND

The citric acid cycle can govern the energy metabolism in aerobic organisms. In addition, the cycle can provide precursors for biosynthesis of several amino acids, lipids, chlorophyll and other growth-related metabolites. The citric acid cycle is non-catalytic, which means that molecules used in biosynthesis need to be replenished so that the cycle can keep generating energy. Regardless of how much acetyl CoA is fed into the citric acid cycle, the cycle is able to produce merely a limited amount of citric acid intermediates. Anaplerotic substrates can be used to produce intermediates that are used to replenish the oxidative capacity of the citric acid cycle.

Anaplerosis refers to the process of replenishing the citric acid cycle intermediates and restoring energy balance of the cell (metabolic homeostasis). Odd-chain fatty acids (OCFA) can be considered anaplerotic because, along with acetate units, they can also release propionic acid which can enter the citric acid cycle through the methylmalonate pathway (OCFA catabolism). Typical dietary sources of OCFA are milk and butter, but they have only trace amounts (<2% total fatty acids, TFA) of pentadecanoic (C15:0) and heptadecanoic (C17:0) acid. Synthetically produced concentrated sources, such as tripentanoin and triheptanoin (e.g., oils containing C5:0 and C7:0), are not considered nutritional lipids. Further, current methods that involve the use of *Yarrowia lipolytica* to produce odd chain fatty acids utilize genetic modification. Specifically, for example, these methods utilize the deletion of the PHD1 gene in order to improve lipid accumulation. Ref 10.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

Disclosed are compositions rich in odd-chain fatty acids (OCFA), including pentadecanoic and heptadecanoic fatty acids, and products rich in tridecanoic, pentadecanoic and heptadecanoic fatty acids derived from microalgae, yeast or fungi; OCFA promoters that can be used to induce OCFA production; and processes that help reduce an amount of propionate used in OCFA production. Further, techniques and systems can utilize OCFA rich anaplerotic oils from cultured microbials as supplements or additives to foods as a nutritional supplement. For example, such supplements may be used to replace significant amounts of the dietary even chain saturated fat with odd chain saturated fat, without significantly changing the dietary habits of the consumer. In this example, the supplements described herein can be incorporated both as a direct food ingredient and in many different food products. Further, techniques and systems can be used to identify the benefits of consumption of these compositions rich in OCFA.

Further, techniques and systems are disclosed for identifying propionic acid toxicity in some types of microorganisms, for example, in order to utilize an upper threshold of propionic acid during cultivation to promote OCFA production. Additionally, techniques and systems are disclosed for identifying and using promotors of OCFA production.

In accordance with one or more embodiments of the present invention, a method for incorporating microbial anaplerotic oil rich in odd-chain fatty acids (OCFA) into food for consumption is disclosed. The method comprises: identifying a unit amount of saturated fat that is present in a target food; determining an amount of microbial anaplerotic oil rich in OCFA to incorporate into the target food, the determining comprising: identifying an amount of OCFA present in the microbial anaplerotic oil as a ratio of OCFA amount per unit of microbial anaplerotic oil, wherein at least five percent of the total fatty acid (TFA) of the microbial anaplerotic oil are OCFA; and combining the ratio with the unit amount of saturated fat resulting in the amount of microbial anaplerotic oil rich in OCFA to incorporate into the target food; and adding the determined amount of microbial anaplerotic oil rich in OCFA to the target food.

In accordance with one or more embodiments of the present invention, a food additive comprising microbial anaplerotic oil rich in odd-chain fatty acids (OCFA) is disclosed. The microbial anaplerotic oil is derived from a microbial strain cultured with added propionate resulting in elevated levels of OCFA in a microbial mass of the microbial strain wherein: at least five percent of the microbial anaplerotic oil from the microbial strain's total fatty acid (TFA) content is odd-chain fatty acids (OCFA); and at least one percent cell dry weight (CDW) of the microbial mass from the microbial strain is odd-chain fatty acids (OCFA).

In accordance with one or more embodiments of the present invention, a food rich in odd-chain fatty acids (OCFA) for consumption by human and non-human animals is disclosed. The food comprises: an amount of microbial anaplerotic oil derived from a microbial strain cultured with an added propionate precursor or added propionate, resulting in elevated levels of OCFA in a microbial mass, the microbial anaplerotic oil comprising: a melting point greater than or equal to thirty-five degrees Celsius; at least five percent of the microbial anaplerotic oil from the microbial strain's total fatty acid (TFA) content is odd-chain fatty acids (OCFA); and at least one percent cell dry weight (CDW) of the microbial mass from the microbial strain is odd-chain fatty acids (OCFA).

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

The claimed matter may take physical form in certain parts and arrangements of parts, a preferred embodiment of which will be described in detail in the specification and illustrated in the accompanying drawings which form a part hereof, and wherein:

FIG. 48 is a table, (Table 24) that illustrates total lipids and Fatty Acid profile from a 1000 L pilot fermenter for *Aurantiochytrium acetophilum* HS399 odd chain fatty acid fermentation;

FIG. 54 is a table (Table 25) that illustrates a list of results for respective alternative promoters of odd chain fatty acid (OCFAs) production in *Aurantiochytrium acetophilum* HS399;

FIG. 55 is a table, (Table 26) that illustrates a list of fatty acid compositions of several vegetable oils;

DETAILED DESCRIPTION

Figure 1:
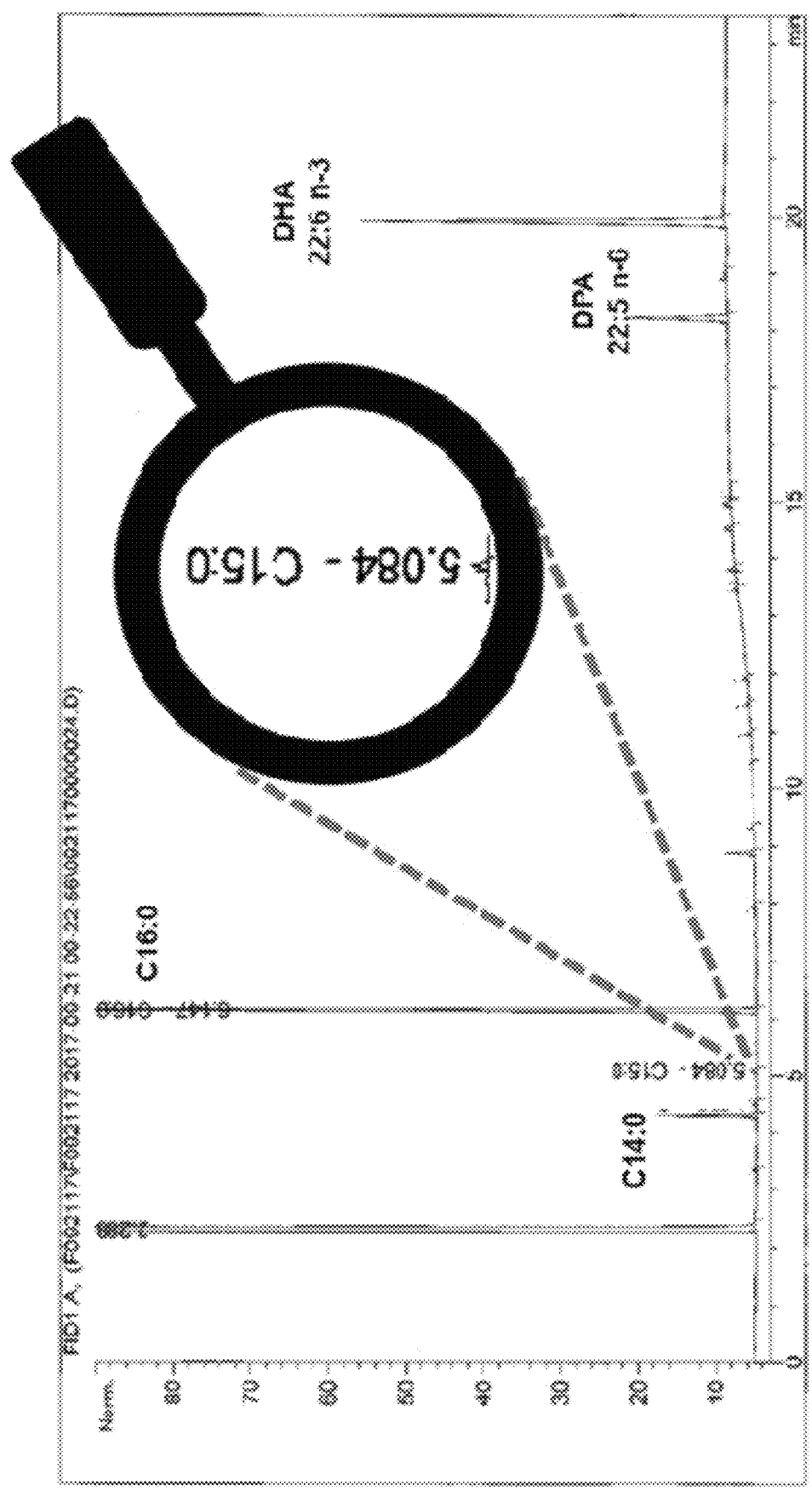
FIG. 1 is a chromatogram of *Aurantiochytrium acetophilum* HS399 displaying the microalgal fatty acid profile.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

With reference to the drawings, like reference numerals designate identical or corresponding parts throughout the several views. However, the inclusion of like elements in different views does not mean a given embodiment necessarily includes such elements or that all embodiments of the claimed subject matter include such elements. The examples and figures are illustrative only and not meant to limit the claimed subject matter, which is measured by the scope and spirit of the claims.

Anaplerosis refers to the replenishment of citric acid intermediates that have been extracted by the cell for biosynthesis. Anaplerotic substrates, such as glucose, protein and odd chain fatty acids (OCFAs), could be converted into citric acid intermediates to restore an energy imbalance of the cell. Anaplerotic substrates are often referred as gluconeogenic substrates. OCFAs are different from other anaplerotic substrates because they can undergo ketosis and cross the blood-brain barrier. Therefore, OCFAs have been associated with a decrease in metabolic disease risk, and their intake has been proposed for the treatment and prevention of various gene and brain disorders. The presence of OCFAs in diet is scarce and typically limited to ruminant fat (e.g., butter), which contains only trace amounts (<2% total fatty acid (TFA)) of pentadecanoic acid (C15:0) and heptadecanoic acid (17:0). Existing pharma OCFAs, such as tripentanoin and triheptanoin oils, are produced synthetically, and are made of fatty acids that are not typically present in a human diet. Alternatively, as described herein, a process may be devised that can result in a natural oil comprising large (e.g., >50 total fatty acid (TFA)) quantities of dietary (e.g., C15:0 and C17:0) OCFAs.

Typical anaplerotic substrates can include pyruvate (e.g., derived from carbohydrates), glutamine/glutamate (e.g., derived from protein) and precursors of propionyl-CoA, such as OCFAs. Anaplerotic substrates can be used to restore energy balance in the mitochondria; and, there is a wide range of pathologies to which OCFAs may provide benefits. As an example, in this aspect, OCFAs have been experimentally used to treat: gene metabolic disorders, such as Glut1 deficiency, Fatty Acid Oxidation Disorder (FAOD), Pyruvate Carboxylase Deficiency, Carnitine Palmitoyltransferase II Deficiency, Huntington, Phenylketonuria, Adult Polyglucosan Body Disease (APBD), and Long-Chain Fat Oxidation Disorders; neural disorders, such as Epilepsy, Alzheimer's Disease, and Autism Spectrum Disorder (ASD); circulatory system disorders, and diabetes type II and other diseases associated to the metabolic syndrome epidemics.

Dietary odd chain fatty acids (OCFA), pentadecanoic acid (C15:0) and heptadecanoic acid (C17:0), also known as margaric acid, may be derived from ruminant fat (e.g., butter), and are thought to be likely derived from bacterial anaerobic activity in the rumen of dairy producing animals. These OCFAs can be found in very small amounts (e.g., <2% total fatty acids (TFA)) in some dairy products (e.g., milk and butter). Pentadecanoic acid (C15:0) and heptadecanoic acid (C17:0) have also been found to be produced in the human gut, which may be triggered by dietary fiber intake, presumably supporting bacterial anaerobic activity. Ref. 1. Because only trace amounts of odd chain fatty acids (e.g., C15:0 and C17:0) are present in human diets, alternative sources (i.e., nutraceuticals, medical foods or therapeutics) can be used to significantly increase the intake of this type of nutrient.

Currently, merely limited amounts of odd chain fatty acids (e.g., C15:0 and C17:0) are readily available from known natural, dietary sources, such as ruminant fat. Techniques and systems can be devised for producing a natural anaplerotic oil that contains significant dietary OCFAs. In one aspect, compositions can be created that comprise a higher concentration, than current sources, of odd chain fatty acids, such as pentadecanoic (C15:0) and heptadecanoic (C17:0) fatty acids. Further, in one aspect, a method can be devised for efficient and affective generation of such fatty acids from a newly derived source.

Microbials can produce a variety of fatty acids, the composition of which can vary among different strains. As an example, thraustochytrid microalgae can accumulate lipids up to eighty-five (85%) of their dry weight; and, amongst the oleaginous microorganisms, they may be one of the fastest growing. Further, these organisms can be adapted to fermentation conditions (e.g., low shear sensitivity, high osmotolerance) for use in industrial production of microbe-based oils. For example, *A. acetophilum* HS399 is a thraustochytrid that can produce an oil containing palmitic acid (e.g., 45% total fatty acids (TFA)), n-6 docosapentaenoic acid (e.g., 8% TFA), and n-3 docosahexaenoic (e.g., 40% TFA) as the main fatty acids, with other fatty acids present in trace amounts. Pursuant to the requirements of the Budapest Treaty, a live culture of the *Aurantiochytrium acetophilum* HS399 microalgae strain described herein was deposited on Sep. 12, 2019 at National Center for Marine Algae and Microbiota (NCMA), located at 60 Bigelow Drive, East Boothbay, ME 04544, USA and received Bigelow Accession Number 201909001.

The trace fatty acids of *A. acetophilum* HS399 can include pentadecanoic acid (C15:0) and heptadecanoic acid (C17:0) (e.g., at <0.3% TFA). The trace fatty acids, including these two identified fatty acids, are typically ignored in the lipid profile reports for these organisms. OCFA, including pentadecanoic acid and heptadecanoic acid, are fatty acids that contain an odd number of carbon atoms in the structure. OCFA are typically related to bacterial activity (e.g., propionic acid bacteria), and are less likely to be present in algae, yeast/fungi, and plants.

FIG. 1 is a chromatogram of *Aurantiochytrium acetophilum* HS399 illustrating the microalgae's fatty acid profile. As shown in FIG. 1, *A. acetophilum* HS399 naturally contains trace amounts of C15:0. The presence of trace amounts in *A. acetophilum* HS399 suggests that the pathway responsible for the synthesis of OCFA may be present in *A. acetophilum* HS399. Because of the composition of their fatty acid profile, and their ability to be grown rapidly, microbials such as *A. acetophilum* HS399 may provide an attractive source of odd-chain fatty acids, by generating odd-chain fatty acids in a more concentrated manner than other known natural sources, such as milk fat (e.g., providing a more cost effective and efficient source of OCFA). As an example, a benefit of using microbials in place of butter and other ruminant fat is the higher concentration of OCFA found in them. In addition, as another example benefit, some microbial oil lacks residues of phytol or phytanic acid that are often present in ruminant fat. Consumption of phytol or phytanic acid can lead to health concerns in some individuals.

Techniques can be devised that provide for an increased production of naturally occurring odd-chain fatty acids from microbials than might be generated from typical microbials. The cultivated microbial and/or isolated composition may be used individually as products or as an ingredient in a variety of products. As an example, microalgae such as *A. acetophilum* HS399 can be cultivated to produce a desirable fatty acid profile comprising OCFA, which may be isolated through various extraction processes. In this example, the isolated oil from *A. acetophilum* HS399, containing the OCFA, may comprise a composition rich in OCFA, such as pentadecanoic acid (C15:0) and heptadecanoic acid (C17:0). As described herein, in one implementation, the algae may be cultivated using an improved method that includes the use of a complex culture media, which can promote increased production of the OCFA.

In one implementation, the microbials, such as microorganisms comprising algae, microalgae, yeast, and fungi, including species from the class Labyrinthulomycetes, such as the species *Aurantiochytrium acetophilum*, may be cultivated using an improved method that includes the presence of a complex media, which can promote increased production of the OCFA. In this implementation, an amount of heptadecanoic acid produced by *A. acetophilum* HS399 can increase from <0.3 up to 1% TFA when a complex culture media containing yeast extract and proteose peptone is used as a replacement for previously utilized media (e.g., defined media). In this implementation, the increase of heptadecanoic acid may be proportional to the amount of proteose peptone used in the complex culture media. The increase in heptadecanoic acid in the cultured *A. acetophilum* HS399, using this technique, suggests that the presence of OCFA in thraustochytrids may not be strain specific, nor stress related. Ref. 3, 5. Instead, using this technique, the increase in heptadecanoic acid is likely due to the presence of added nutrients in the media that provide for the accumulation of this OCFA. Therefore, the high levels of odd chain fatty acids reported in some thraustochytrids strains (Ref. 4) might not be a strain specific trait, nor a physiological response to stress (Ref. 3,5) but rather the result of poor growth and/or high yeast extract or other OCFA precursors.

In one implementation, propionic acid (e.g., and or one or more propionates, such as the anion, salts, and/or esters of propionic acid) may be used as a precursor for production of OCFA. Proteose peptone comprises valine, isoleucine, and methionine amino acids, respectively comprising at least a three-carbon chain, which may provide a precursor three-carbon backbone of propionic acid. In this implementation, for example, it is likely that *A. acetophilum* HS399 can incorporate propionic acid in its lipid generation pathway, resulting in the production of OCFA.

Generally, fatty acid synthesis in oleaginous microbials consists of a lipid synthesis pathway involving acetyl CoA, and some metabolic cycles. As an example, acetyl-coenzyme A (Acetyl-CoA) is a universal two carbon donor, or building block, for fatty acid biosynthesis. Acetyl-CoA can be supplied by multiple paths, from various origins, and then subsequently activated into acetyl-acyl carrier protein (ACP) or converted to Malonyl CoA through Acetyl-CoA carboxylase. Later, by sequential reactions of condensation, reduction dehydration and reduction, palmitic acid will be produced.

In one aspect, analysis of the genome of *A. acetophilum* HS399 suggests that saturated fats are synthesized through the Fatty Acid Synthase (FAS) pathway that uses acetyl-coA as a building block for the fatty acid elongation. The production of even chain fatty acids uses a malonyl-ACP as a substrate for elongation. As described herein, in one implementation, when propionic acid is present the acyl carrier protein (ACP) cleaves to methyl-malonyl instead of malonyl, resulting in the FAS producing of odd chain fatty acids instead of even chain fatty acids. Palmitic acid (C16:0) is typically the primary even chain fatty acid in *A. acetophilum* HS399, while the primary OCFA is typically pentadecanoic (C15:0) instead of heptadecanoic acid (17:0). In this implementation, fatty acid synthesis of palmitic acid (C16:0) undergoes through 6-consecutive elongation cycles, while the (C15:0) OCFA undergoes only 5-elongation cycles before the fatty acid is liberated from the acyl carrier protein. This suggests that FAS is governed by a chain length factor.

Figure 2:
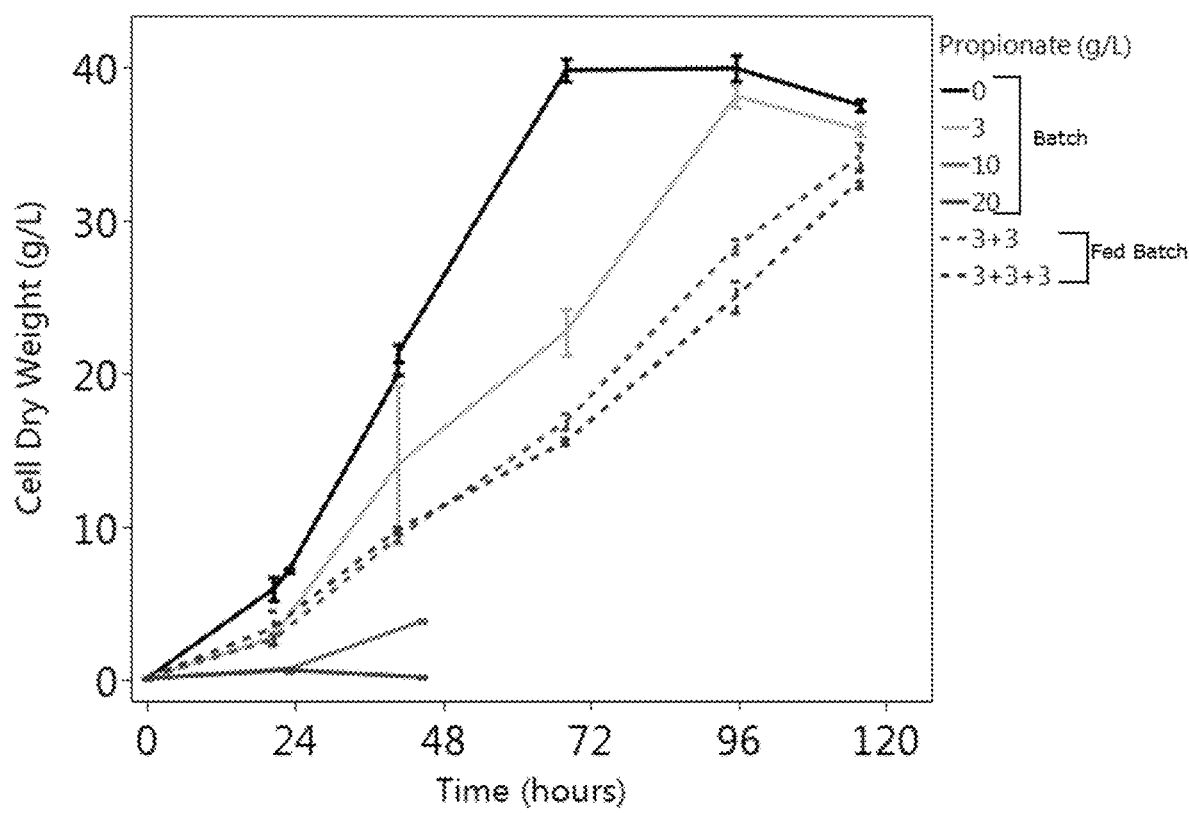
FIG. 2 is a line graph depicting the impact of propionate supplementation on microalgae growth under batch and fed-batch conditions.

In one aspect, propionic acid is commonly used for its antimicrobial characteristics, among other things. For example, propionic acid can inhibit growth of mold and bacteria at low levels (e.g., <1% by weight), and is often used as an antimicrobial agent to preserve animal and/or human food sources. Other uses include adding propionic acid to products to mitigate algae growth on surfaces. In this aspect, as an illustrative example, FIG. 2 illustrates propionic acid's growth inhibitory characteristics for *A. acetophilum* HS399, at concentrations as low as 3 grams/liter (g/L); and lethality to *A. acetophilum* HS399 at concentrations of 10 g/L.

Figure 3:
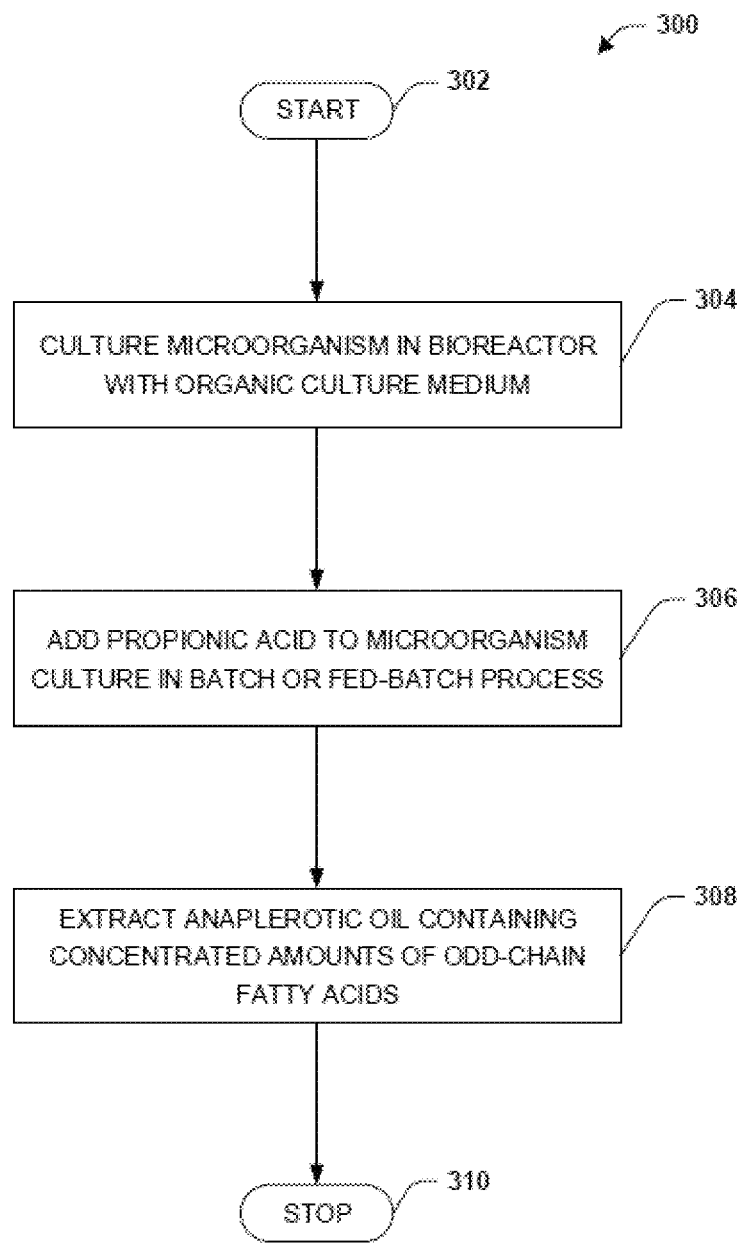
FIG. 3 is a flow chart of steps involved in a method according to an exemplary embodiment of the present disclosure.

In this aspect, in addition to the common and traditional use of propionic acid as an antimicrobial agent that kills algae, as described herein, techniques have been devised for propionic acid to be used to facilitate in growing algae, and/or to increase OCFA production in the algae. In one implementation, in this aspect, propionic acid (e.g., and/or propionates) can be introduced into an algal bioprocess using a fed-batch approach, while reducing the potential toxic effects on the algae. FIG. 3 is a flow diagram illustrating an exemplary method 300 for introducing propionic acid into an algal growth culture program. The exemplary method begins at 302. At reference numeral 304, a microorganism (e.g., microalgae such as *A. acetophilum* HS399) can be added to the culture medium. At reference numeral 306, propionic acid may be added to the culture medium comprising the microorganism (e.g., *A. acetophilum* HS399) in a batch, continuous or fed-batch process, and cultured in a bioreactor having with the culture medium (e.g., organic).

In one embodiment, the propionic acid can be added at a ratio of at least 0.05 g of propionic acid per gram of *A. acetophilum* HS399 biomass, in order to accumulate elevated amounts of OCFA. In one embodiment, 0.15 g of propionic acid per gram of *A. acetophilum* HS399 biomass, in order to accumulate OCFA above 50% TFA. In another implementation, the propionic acid can be added at a rate of above zero and up to about 3 g/L per day. In one implementation, the propionic acid can be added at a rate of zero and up to about 3 g/L per day for three days, resulting in a total propionic acid addition of about 9 g/L. In one embodiment, adding the propionate can comprise adding the propionate in a fed-batch into the culture medium. In one embodiment, adding the propionate can comprise adjusting the propionate fed to produce OCFAs in a range of 5 and 70% TFAs.

At reference numeral 308, anaplerotic oil containing concentrated amounts of OCFA can be extracted from the *A. acetophilum* HS399. In one embodiment, anaplerotic oil can be produced from the cultured microorganisms, wherein at least five percent of the total fatty acids (TFA) of the anaplerotic oil are OCFA, and OCFA make up at least one percent cell dry weight (CDW) of the anaplerotic oil. Having extracted the anaplerotic oil containing concentrated amounts of OCFA the exemplary method 300 ends at 310.

In one implementation, the propionate fed approach can cause some microorganism (e.g., *A. acetophilum* HS399) growth inhibition, for example, but may not result in a complete culture loss of the microorganism batch. In this implementation, the fed-batch approach can achieve similar cell densities and overall lipid accumulation as a similar control batch with no propionic acid fed, with merely a one-day difference. As one example, propionic acid can be fed into the algal culture batch on demand (e.g., automatically, using a pH-auxostat fed batch system). As another example, propionic acid can be fed into the algal batch, along with a carbon source (e.g., glucose, glycerol or acetate), at a ratio below 0.1 of weight to weight (w/w) of propionic acid to carbon source (propionic acid/carbon source). In another example, propionic acid can be fed along with the carbon source at a ratio below 0.05 w/w propionic acid/carbon source, to mitigate avoid accumulation of propionate in the culture media. In one example, propionic acid may be fed into a culture at a culture pH higher than 5. A low pH increases the toxicity of propionic acid making it more difficult to balance the window between propionate incorporation and grown inhibition.

EXAMPLES

Embodiments described herein are exemplified and additional embodiments are disclosed in further detail in the following Examples, which are not in any way intended to limit the scope of any aspects of the inventive concepts, described herein.

Example 1—Propionic Acid Incorporation into *A. acetophilum* Fatty Acid Synthase (FAS)

In one example implementation, the resulting impact on growth and lipid accumulation of *Aurantiochytrium acetophilum* HS399 when using propionic acid can be illustrated. In this implementation, four treatments can be prepared with varying concentrations of propionate (e.g., 0, 10, 20, 30 g/L), hereinafter: "P0, P10, P20 and P30" respectively. In this implementation, propionate can be batched as sodium propionate in a flask culture. Respective Erlenmeyer flasks (250 mL) can be inoculated (1% v/v) in triplicates with a 24 hour (h) old culture of *A. acetophilum* HS399 and incubated in an orbital shaker at 180 rpm and 27° C.

In this implementation, the respective Erlenmeyer flasks contain 100 mL of a medium supplemented with (g/L): dextrose (50), ammonium acetate (2.3), NaCl (12.5), $MgSO_4$ $7H_2O$ (2.5), $KH_2PO_4$ (0.5), KCl (0.5) and $CaCl_2$ (0.1). This medium also contains trace element solution (5 ml/L) and vitamin solution (1 ml/L). The trace element solution contains (g/L): EDTA di-sodium salt (6), $FeCl_3$ $6H_2O$ (0.29), $H_3BO_3$ (6.84), $MnCl_2$ $4H_2O$ (0.86), $ZnCl_2$ (0.06), $CoCl_2$ $6H_2O$ (0.026), $NiSO_4$ $6H_2O$ (0.052), $CuSO_4$ 5H$_2$O (0.002), Na$_2$MoO$_4$H$_2$O (0.005). The vitamin solution contains (mg/L): thiamine (100), biotin (0.5) and cyanocobalamin (0.5). All culture materials can be autoclaved (121° C., 15 min) and media can be filter sterilized before use. A propionic acid stock solution (200 g/L) can be used to feed propionic acid. Daily samples can be collected to analyze the cell dry weight, residual glucose, culture pH, lipid and fatty acid composition of the cultures. Cell dry weights are analyzed by vacuum filtration (0.2 μm) and washed with a solution of ammonium bicarbonate. Residual glucose is analyzed using a colorimetric method based on glucose peroxidase activity. Biomass for lipid analysis can be centrifuged and washed using purified water. The washed biomass can be freeze dried. Total lipids are analyzed using the Folch method (AOAC 996.06) and the FAMES are analyzed by gas chromatography using nonadecanoic (C19:0) acid as an internal standard.

Figure 4:
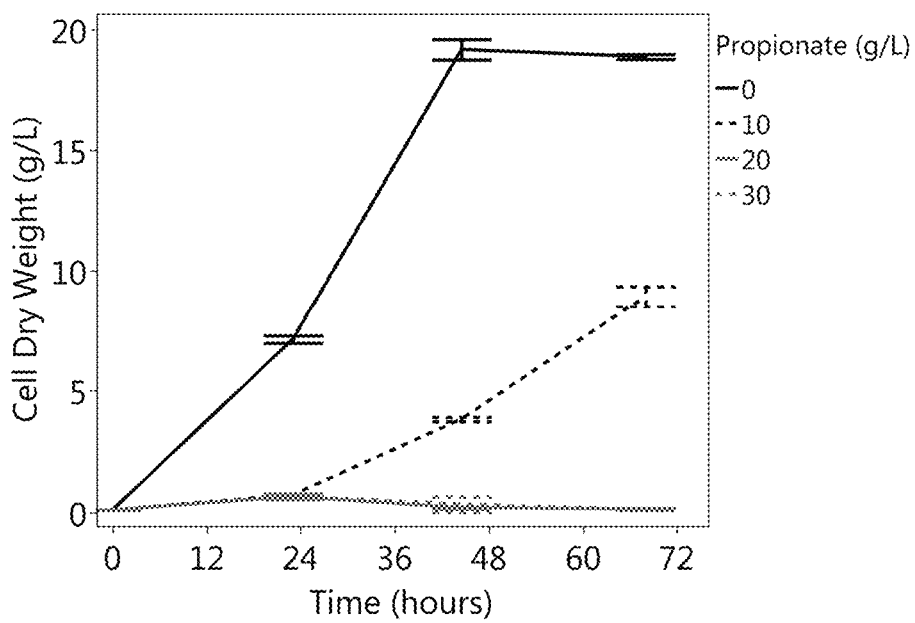
FIG. 4 is a line graph depicting *Aurantiochytrium acetophilum* HS399 growth in response to propionate supplementation.
Figure 5:
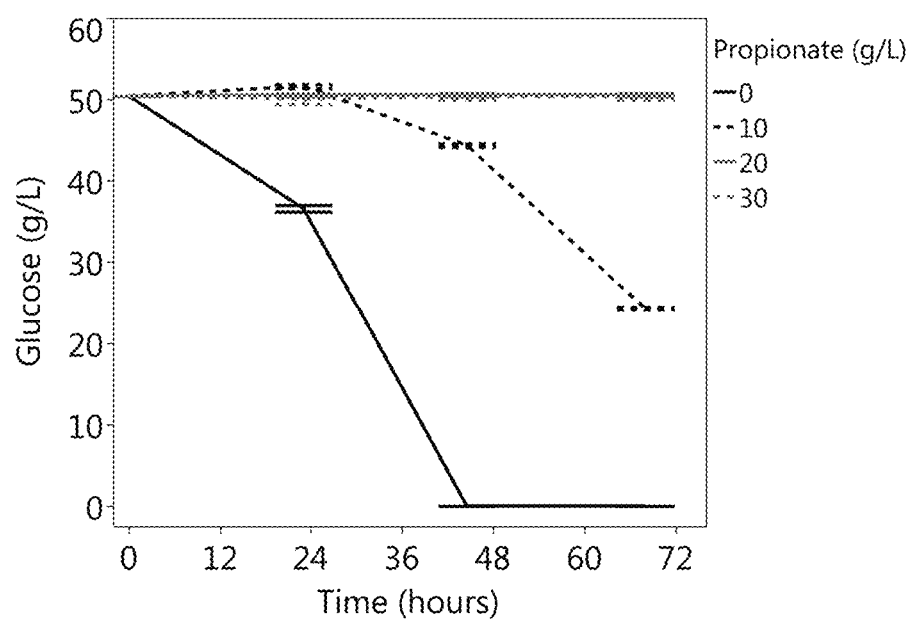
FIG. 5 is a line graph depicting *Aurantiochytrium acetophilum* HS399 residual glucose consumption in response to propionate supplementation.
Figure 6:
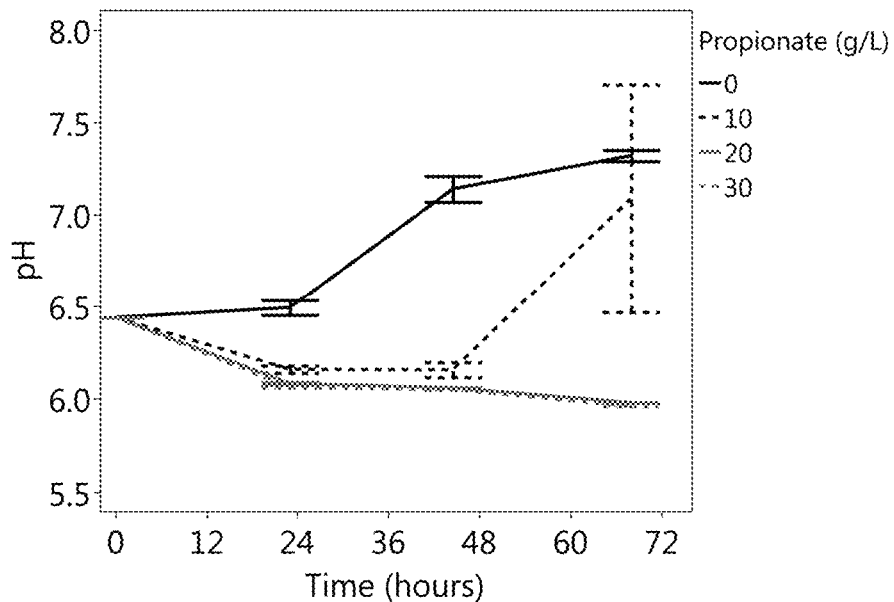
FIG. 6 is a line graph depicting the culture pH-drift of *Aurantiochytrium acetophilum* HS399 fed with varying levels of propionate.

FIG. 4 illustrates the resulting cell dry weights, and the resulting residual glucose is illustrated shown in FIG. 5. As illustrated by the results, propionic acid is lethal at concentrations of 20 g/L and 30 g/L, while concentrations of 10 g/L are strongly inhibitory to the growth of *A. acetophilum* HS399. FIG. 6 illustrates the *A. acetophilum* HS399 growth results in the alkalization of the medium, presumably associated to the consumption of organic acids. As shown by the lipid and fatty acid data at 68 h of incubation from P0 and P10 in Table 1 below, the presence of propionate decreases lipid and total fatty acid accumulation. Further, the presence of propionate produces results in a decrease in palmitic (C16:0) and an increase in saturated odd chain fatty acids (OCFAs) tridecanoic (C13:0), pentadecanoic (C15:0) and heptadecanoic acid (C17:0), which can result in propionic incorporation/deposition (see Table 2). As illustrated, the increase of total OCFA (C13, C15, C17) from 0.2% at zero propionate to 63% total OCFA at 10 g/L propionate suggests that propionate is incorporated into the fatty acid synthase pathway (FAS). The lack of OCFA in the polyunsaturated fraction suggests that propionate may not be incorporated/deposited in the polyketide synthase pathway (PKS).

TABLE 1

Impact of propionate supplementation in HS399 lipid and fatty acid profile after 68 h incubation

| Propionate (g/L) | 0 | 10 |
|---|---|---|
| Total Lipids (% DW) | 83.0 ± 0.0 | 55.3 ± 0.6 |
| Total Fatty Acids (% DW) | 69.5 ± 0.6 | 42.8 ± 0.9 |
| Fatty Acid Profile (% TFA) | | |
| 13:0 | 0.0 ± 0.0 | 3.0 ± 0.1 |
| 14:0 | 3.1 ± 0.0 | 0.9 ± 0.0 |
| 15:0 | 0.2 ± 0.0 | 51.7 ± 0.6 |
| 16:0 | 52.7 ± 0.1 | 5.1 ± 0.3 |
| 17:0 | 0.0 ± 0.0 | 8.3 ± 0.0 |
| 18:0 | 1.6 ± 0.0 | 0.2 ± 0.1 |
| 22:5 (n-6) | 7.3 ± 0.1 | 3.0 ± 0.1 |
| 22:6 (n-3) | 32.6 ± 0.1 | 24.9 ± 0.4 |
| Other FA | 2.2 ± 0.0 | 2.2 ± 1.2 |
| OCFA (% TFA) | 0.2 ± 0.0 | 63.1 ± 0.7 |

TABLE 2

Propionate deposition, feeding rate and productivity of OCFAs in response to propionate supplementation

| Propionate (g/L) | PA Feeding Rate ($g_{PA}/g_{Biomass}$) | Propionate deposition (%) | OCFA Productivity (g/L/d) |
|---|---|---|---|
| 0 | 0.00 ± 0.00 | 0.0 ± 0.0 | 0.00 ± 0.00 |
| 1100 | 1.12 ± 0.05 | 6.9 ± 0.5 | 0.81 ± 0.06 |

Example 2—Propionic Concentration in *Aurantiochytrium* Fatty Acid Profile

In another implementation, fed-batching *Aurantiochytrium acetophilum* HS399 with propionic acid may impact its growth, and lipid accumulation. As an example, in this implementation, four treatments can be prepared with varying concentrations of propionate (0, 3, 6, 9 g/L), hereinafter "P0, P3, P6 and P9" respectively. Propionate can be fed-batch fed as sodium propionate in a flask culture with daily additions at 3 g/L. Respective Erlenmeyer flasks (250 mL) are inoculated (1% v/v) in triplicates with a 24 h old culture of *A. acetophilum* HS399. The cultures are incubated in an orbital shaker at 180 rpm and 27° C.

Figure 9:
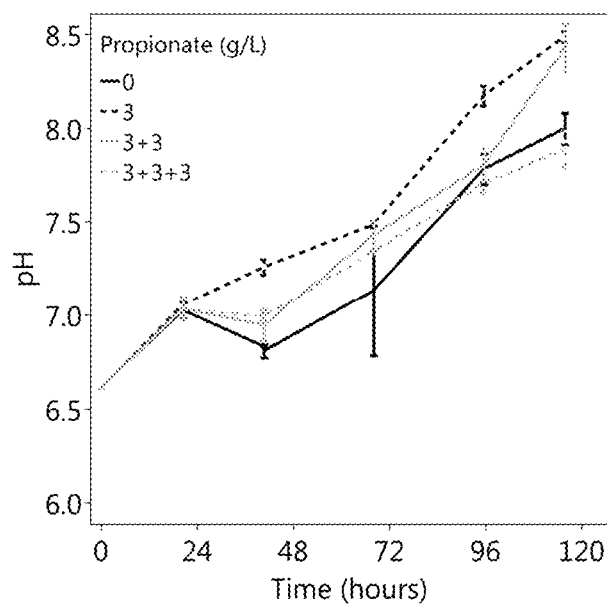
FIG. 9 is a line graph depicting the culture pH-drift of *Aurantiochytrium acetophilum* HS399 fed with varying levels of propionate.

Respective Erlenmeyer flasks contain 100 mL of a medium supplemented with (g/L): dextrose (100), ammonium acetate (4.6), NaCl (12.5), MgSO$_4$ 7H$_2$O (2.5), KH$_2$PO$_4$ (0.5), KCl (0.5) and CaCl$_2$ (0.1). This medium also contains trace element solution (5 ml/L) and vitamin solution (1 ml/L). The trace element solution contains (g/L): EDTA di-sodium salt (6), FeCl$_3$ 6H$_2$O (0.29), H$_2$BO$_3$ (6.84), MnCl$_2$ 4H$_2$O (0.86), ZnCl$_2$ (0.06), CoCl$_2$ 6H$_2$O (0.026), NiSO$_4$ 6H$_2$O (0.052), CuSO$_4$ 5H$_2$O (0.002), Na$_2$MoO$_4$H$_2$O (0.005). The vitamin solution contains (mg/L): thiamine (100), biotin (0.5) and cyanocobalamin (0.5). All culture materials can be autoclaved (e.g., 121° C., 15 min) and the media can be filter sterilized before use. A propionic acid stock solution (200 g/L) can be used as the fed propionic acid. In this example, P0 is not fed any propionate, P3 is fed 3 g/L on day 0 (inoculation day), P6 is fed 3 g/L on day 0 and 3 g/L on day 1, and P9 is fed 3 g/L on day 0, 1 and 2. Daily samples are collected to analyze the cell dry weight, residual glucose, culture pH (see FIG. 9), and lipid and fatty acid composition of the cultures. Cell dry weights (CDW) can be analyzed by filtration (e.g., 0.2 μm filter media) using a vacuum, and washed with a solution of ammonium bicarbonate. Residual glucose can be analyzed using colorimetric methods based on glucose peroxidase activity. Biomass for lipid analysis is centrifuged and washed using purified water. The washed biomass is freeze dried. Total lipids are analyzed using Folch method (AOAC 996.06) and the FAMES re analyzed by gas chromatography using nonadecanoic (C19:0) acid as an internal standard.

Figure 7:
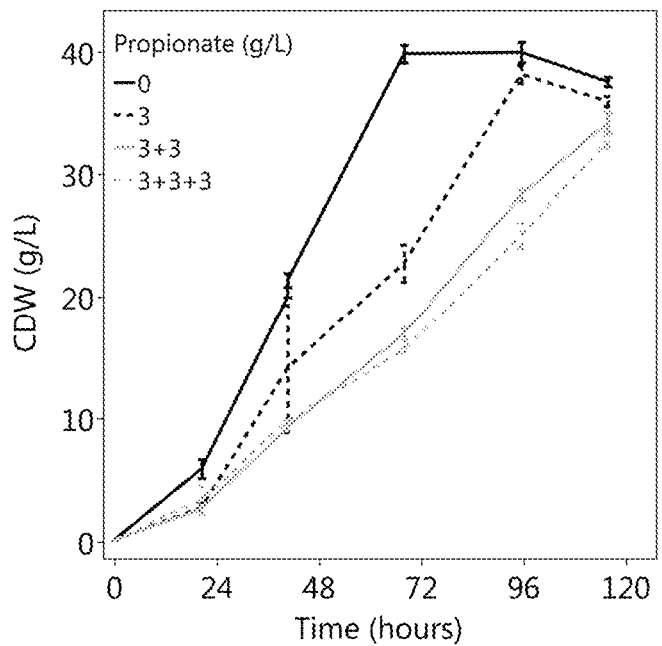
FIG. 7 is a line graph depicting *Aurantiochytrium acetophilum* HS399 growth in response to propionate supplementation.
Figure 8:
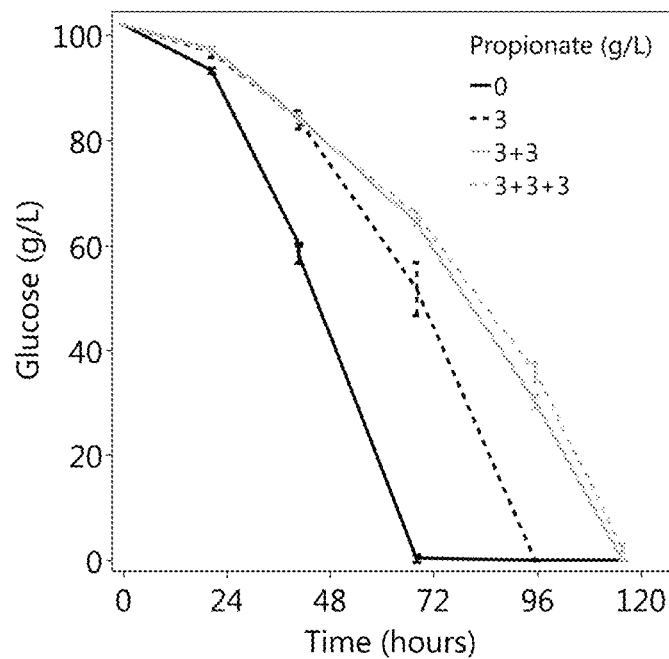
FIG. 8 is a line graph depicting *Aurantiochytrium acetophilum* HS399 residual glucose consumption in response to propionate supplementation.

In this example, as shown by the cell dry weights represented in FIG. 7, and the residual glucose represented in FIG. 8, the treatment that utilized propionic acid produced results illustrating growth inhibition at concentrations as low as 3 g/L (P3). Further, these results illustrate that the growth inhibition effect may be dose dependent, with the strongest inhibition resulting from treatments having higher propionate concentrations (P6 and P9). Even though growth inhibition was exhibited, the 70 h growth achieved in this example for the fed batching of 9 g/L of propionate (~15 g/L) was higher than the growth achieved for the of batching 9 g/L of propionate at inoculation (see Example 1). This example result illustrates that fed-batching can be an effective strategy for mitigating propionic toxicity, while inducing the cells to produce OCFAs.

As an example of this strategy, the lipid and fatty acid data is represented in Tables 3-5, below. These results illustrate lipid accumulation observed at 68 h, 96 h, and 116 h of incubation, respectively. As shown in these Tables, the differences in lipid accumulation due to propionate toxicity decreased at 96 h and 116 h, from the 68 h observation. As illustrated, the treatments, including those supplemented with propionate, accumulated lipids above 70% DW even with growth inhibition. Results of this example illustrate that higher, desired amount of odd chain fatty acids can be accumulated at 96 h for both P6 (62.4% TFA) and P9 (also 62.4% TFA), which illustrates that the 0.18 g of propionate per gram of biomass supplied in P6 may be appropriate to improve OCFA accumulation in *A. acetophilum* HS399 to a desirable level.

Figure 10:
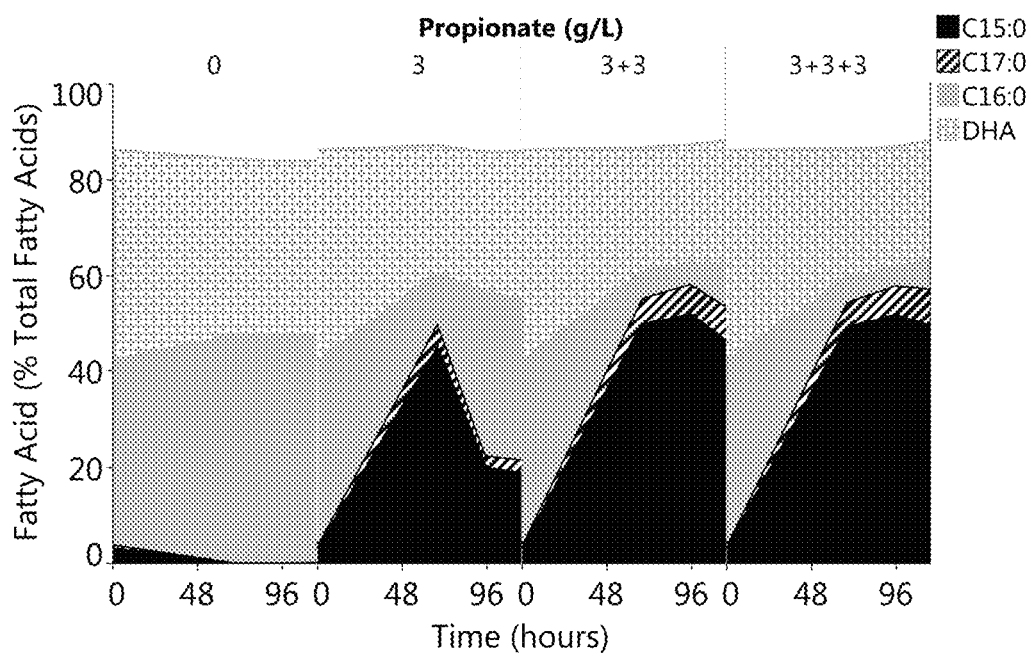
FIG. 10 is a graph depicting fatty acid distribution throughout the culture of *Aurantiochytrium acetophilum* HS399 fed-batch at different propionic levels.
Figure 11:
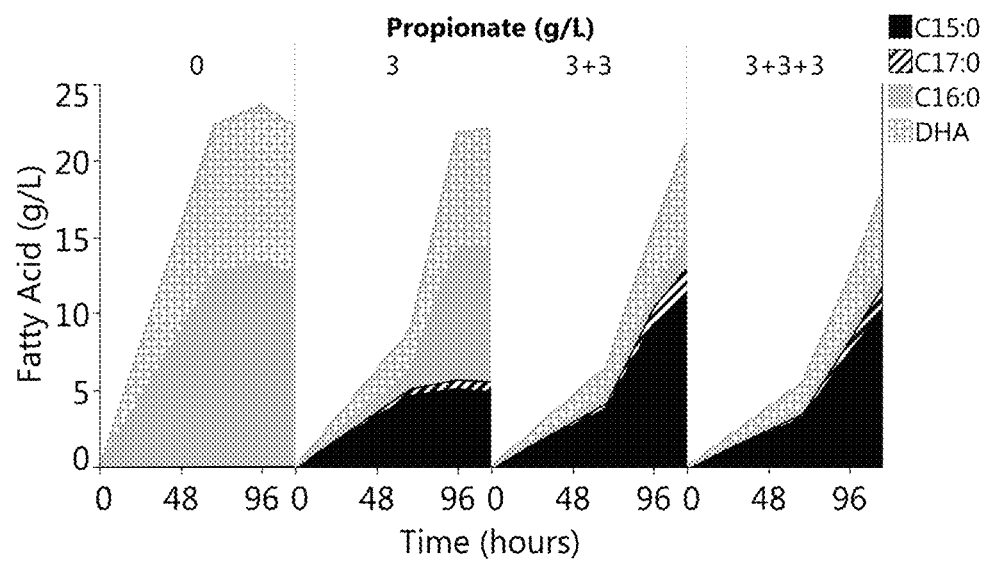
FIG. 11 is a graph depicting fatty acid accumulation throughout the culture of *Aurantiochytrium acetophilum* HS399 fed-batch at different propionic levels.
Figure 12:
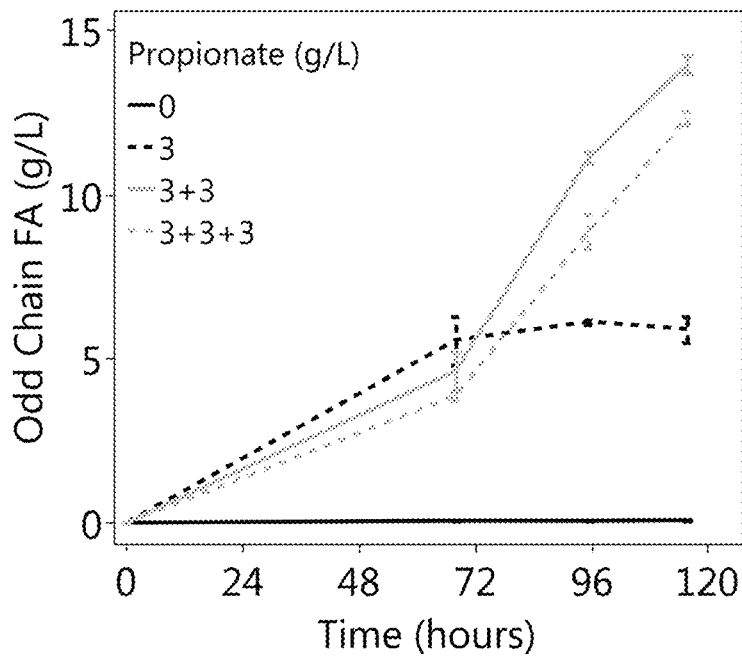
FIG. 12 is a line graph depicting OCFA accumulation in an *Aurantiochytrium acetophilum* HS399 culture fed varying amounts of propionate.

As an example, adding more propionic acid to these treatments/cultures may not further increase the propionic acid, but may increase propionic toxicity with potentially negative impact in growth and lipid accumulation. Further, as an example, adding less propionate (e.g., 0.6 g propionate per gram of biomass), may result in low OCFAs accumulation due to palmitic acid synthesis taking over the OCFAs synthesis after 68 h, as shown in FIG. 10, FIG. 11 and FIG. 12, and summarized in Table 6, below. In this example, the high (e.g., ~66%) propionic acid deposition in fatty acids suggest that propionate may be incorporated (e.g., at least once) in each fatty acid, presumably in the first condensation step of the FAS pathway (methyl malonyl acyl carrier protein condensation). In this example, the remaining propionate may be oxidized, and lost through anaplerosis into the Citric Acid Cycle.

TABLE 3

Lipid and fatty acid profile at 68 h

| | Propionate (g/L) | | | |
|---|---|---|---|---|
| | 0 | 3 | 3 + 3 | 3 + 3 + 3 |
| Total Fatty Acids (% DW) | 66.5 ± 1.5 | 45.1 ± 3.0 | 44.5 ± 4.5 | 40.7 ± 1.7 |
| Fatty Acid Profile (% TFA) | | | | |
| 13:0 | 0.0 ± 0.0 | 3.8 ± 0.6 | 5.2 ± 0.2 | 5.5 ± 0.5 |
| 14:0 | 4.0 ± 0.1 | 2.0 ± 0.3 | 1.5 ± 0.1 | 1.2 ± 0.0 |
| 15:0 | 0.2 ± 0.0 | 44.7 ± 6.0 | 49.6 ± 0.6 | 48.8 ± 0.1 |
| 16:0 | 47.1 ± 0.1 | 10.8 ± 5.6 | 5.4 ± 0.7 | 5.0 ± 0.0 |
| 17:0 | 0.0 ± 0.0 | 5.3 ± 0.6 | 5.8 ± 0.2 | 5.7 ± 0.2 |
| 18:0 | 1.5 ± 0.0 | 0.2 ± 0.3 | 0.0 ± 0.0 | 0.0 ± 0.0 |
| 22:5 (n-6) | 8.6 ± 0.0 | 4.5 ± 0.5 | 3.6 ± 0.1 | 3.5 ± 0.1 |
| 22:6 (n-3) | 36.9 ± 0.3 | 26.3 ± 0.7 | 25.7 ± 0.1 | 26.8 ± 0.3 |
| Other FA | 2.2 ± 0.2 | 2.8 ± 0.2 | 3.3 ± 0.1 | 3.7 ± 0.0 |
| OCFA (% TFA) | 0.2 ± 0.0 | 52.9 ± 7.3 | 60.9 ± 0.6 | 60.6 ± 0.4 |

TABLE 4

Lipid and fatty acid profile at 96 h

| | Propionate (g/L) | | | |
|---|---|---|---|---|
| | 0 | 3 | 3 + 3 | 3 + 3 + 3 |
| Total Lipids (% DW) | 82.3 ± 1.2 | 81.0 ± 1.0 | 73.3 ± 1.5 | 70.0 ± 1.0 |
| Total Fatty Acids (% DW) | 70.6 ± 3.7 | 66.8 ± 4.8 | 62.5 ± 0.3 | 56.3 ± 1.2 |

TABLE 4-continued

Lipid and fatty acid profile at 96 h

| | Propionate (g/L) | | | |
|---|---|---|---|---|
| | 0 | 3 | 3 + 3 | 3 + 3 + 3 |
| Fatty Acid Profile (% TFA) | | | | |
| 13:0 | 0.0 ± 0.0 | 1.4 ± 0.1 | 4.1 ± 0.1 | 4.4 ± 0.1 |
| 14:0 | 3.8 ± 0.1 | 2.8 ± 0.0 | 1.2 ± 0.1 | 1.1 ± 0.0 |
| 15:0 | 0.2 ± 0.0 | 19.7 ± 0.8 | 51.9 ± 0.2 | 51.7 ± 0.2 |
| 16:0 | 47.1 ± 0.4 | 33.9 ± 0.6 | 4.3 ± 0.2 | 3.8 ± 0.1 |
| 17:0 | 0.0 ± 0.0 | 2.7 ± 0.0 | 6.4 ± 0.1 | 6.3 ± 0.0 |
| 18:0 | 1.5 ± 0.0 | 1.0 ± 0.0 | 0.1 ± 0.0 | 0.1 ± 0.0 |
| 22:5 (n-6) | 8.6 ± 0.1 | 6.6 ± 0.1 | 3.5 ± 0.1 | 3.4 ± 0.1 |
| 22:6 (n-3) | 36.5 ± 0.4 | 29.4 ± 0.2 | 24.6 ± 0.1 | 24.9 ± 0.1 |
| Other FA | 2.1 ± 0.0 | 2.2 ± 0.1 | 3.4 ± 0.2 | 3.6 ± 0.1 |
| OCFA (% TFA) | 0.2 ± 0.0 | 24.0 ± 1.0 | 62.8 ± 0.2 | 62.9 ± 0.2 |

TABLE 5

Lipid and fatty acid profile at 116 h

| | Propionate (g/L) | | | |
|---|---|---|---|---|
| | 0 | 3 | 3 + 3 | 3 + 3 + 3 |
| Total Lipids (% DW) | 82.0 ± 1.7 | 74.8 ± 0.3 | 77.7 ± 0.6 | 74.0 ± 1.0 |
| Total Fatty Acids (% DW) | 70.7 ± 2.2 | 71.7 ± 4.3 | 70.8 ± 0.6 | 63.1 ± 2.0 |
| Fatty Acid Profile (% TFA) | | | | |
| 13:0 | 0.0 ± 0.0 | 1.1 ± 0.0 | 2.7 ± 0.1 | 3.0 ± 0.1 |
| 14:0 | 3.7 ± 0.1 | 2.5 ± 0.0 | 1.3 ± 0.0 | 1.1 ± 0.0 |
| 15:0 | 0.3 ± 0.1 | 18.6 ± 0.6 | 46.0 ± 1.1 | 49.2 ± 0.3 |
| 16:0 | 46.7 ± 0.1 | 33.8 ± 0.5 | 8.7 ± 1.0 | 5.8 ± 0.3 |
| 17:0 | 0.0 ± 0.0 | 3.0 ± 0.1 | 7.7 ± 0.2 | 8.2 ± 0.1 |
| 18:0 | 1.5 ± 0.0 | 1.1 ± 0.0 | 0.2 ± 0.0 | 0.2 ± 0.0 |
| 22:5 (n-6) | 8.7 ± 0.1 | 6.8 ± 0.0 | 4.4 ± 0.2 | 4.0 ± 0.0 |
| 22:6 (n-3) | 36.8 ± 0.3 | 30.4 ± 0.0 | 25.6 ± 0.2 | 24.9 ± 0.1 |
| Other FA | 2.2 ± 0.2 | 2.8 ± 0.2 | 3.3 ± 0.1 | 3.7 ± 0.0 |
| OCFA (% TFA) | 0.3 ± 0.1 | 22.8 ± 0.8 | 57.5 ± 1.4 | 60.8 ± 0.2 |

TABLE 6

Results of propionate feeding regime on propionate deposition and productivity of OCFAs by *Aurantiochytrium acetophilum* HS399

| Propionate (g/L) | PA Feeding Rate ($g_{PA}/g_{Biomass}$) | Propionate deposition (%) | OCFA Productivity (g/L/d) |
|---|---|---|---|
| 0 (96 h) | 0.00 ± 0.00 | 0.0 ± 0.0 | 0.0 ± 0.0 |
| 3 (96 h) | 0.08 ± 0.00 | 57.0 ± 0.9 | 1.53 ± 0.02 |
| 3 + 3 (116 h) | 0.18 ± 0.00 | 65.0 ± 0.6 | 2.89 ± 0.06 |
| 3 + 3 + 3 (166 h) | 0.28 ± 0.00 | 39.5 ± 1.7 | 2.56 ± 0.04 |

Table 5 (above) provides results of varying use of propionic acid in an algal culture after 116 hours culturing. As an example, the results in Table 5 illustrate four different approaches to the use of propionic acid in a batch of *Aurantiochytrium acetophilum* HS399, as indicated by the four columns: 0, 3, 3+3, and 3+3+3. The first column indicates no use of propionic acid in the algal batch; the second column indicates the use of merely one does of 3 g/L of propionic acid in the algal batch, the third column indicates the use of two separate doses of 3 g/L each of propionic acid, on separate days; and the fourth column indicates the use of three separate doses of 3 g/L each of propionic acid, at one per day. The respective rows of the Table 5 are indicative of the resulting percentage dry weight (% DW) levels of total lipids, total fatty acids, and each fatty acid profile for the respective approaches (e.g., titled by the fatty acid name or indicator, such as C13:0 (13 chain FA), C14:0 (14 chain fatty acid), etc.).

As illustrated, the use of propionic acid (in columns 2, 3 and 4) indicates an increase in the presence of pentadecanoic acid (C15:0: fifteen-chain FA) in the resulting *Aurantiochytrium acetophilum* HS399 batch, in a dose response manner. As illustrated in column one, no use of propionic acid results in 0.3% pentadecanoic acid of the TFA content. Column two shows that the addition of 3 g/L of propionic acid results in about 18% (18.6%) of pentadecanoic acid of the TFA content; column three shows the batch addition of two separate doses of 3 g/L of propionic acid results in about 40% (46%) of pentadecanoic acid of the TFA content; and column four shows the batch addition of three separate doses of 3 g/L of propionic acid (e.g., such as over a three-day period) results in greater than 40% (49.2%) of pentadecanoic acid of the TFA content.

Conversely, as seen in Table 5, the addition of the propionic acid indicates a reduction in the resulting palmitic acid (C16:0 or e.g., palmitate, such as the salts and esters of palmitic acid) over the same four dose approaches. That is for example, in Table 5, the palmitic acid (C16:0) indicates 46.7% of the TFA profile with no propionic acid; 33.8% at one 3 g/L dose; 8.7% at two doses of 3 g/L each; and 5.8% at three equal doses of 3 g/L. These results suggest that the number of iterative elongation cycles in fatty acid synthetase pathway may be determined by the length of the acyl chain. That is, in the presence of propionic acid, the fatty acid synthetase can prefer to eliminate one elongation cycle and produce pentadecanoic (C15:0), rather than producing heptadecanoic acid (C17:0), through full-seven-elongation cycles. This result appears to be consistent with the hypothesis that stearic acid (C18:0) is not a direct product of fatty acid synthetase, but the elongation of palmitic acid (C16:0).

Further, as illustrated in Table 5, the use of propionic acid in the algal culture batch can also result in production of other fatty acids, such as heptadecanoic acid (C17:0) and tridecanoic acid (C13:0) (e.g., both odd-chain fatty acids), with the total OCFA indicating a result above 60% of TFA (60.4% of TFA total for C13:0+C15:0+C17:0). As indicated in Table 5, as the OCFA production increases, in the respective columns 2-4, the amount of resulting palmitic acid is reduced to 5.8% of the TFA. Additionally, results indicate that the amount of docosahexaenoic acid (DHA) also decreases to greater than about 20% (24.9%) of the TFA. This result may suggest that propionic acid enhances the synthesis of saturated fats from the fatty acid synthase (FAS) over the production of polyunsaturated fatty acids through the polyketide synthase (PKS) pathway.

In one aspect, the resulting product of an algal culture batch utilizing the multi-step propionic dose approach (e.g., three doses of 3 g/L each over three days) may be a highly concentrated anaplerotic oil from microalgae. That is, for example, the resulting product can comprise about 38% of the cell dry weight (CDW) of OCFAs (e.g., 60.4% OCFAs of the 63.1% TFA=38.1% OCFAs of total DW of algal product). In this aspect, no other natural source (e.g., non-synthetic) is known to produce these quantities or concentrations of odd chain fatty acids per batch product (e.g., >50% TFA; and >30% CDW).

In this implementation, as shown in the pentadecanoic (15:0) row of Table 5, the disclosed process can increase the pentadecanoic acid content from about 0.3% TFA, in the resulting product, without the use of propionate, to about 49% in a fed-batch culture with 0.15 g propionate per gram of biomass. In one implementation, it may be desirable to control the daily propionic feed in order to control toxicity (as described herein); however, a per gram biomass fed propionate may be more desirable than the g/L measurement for controlling the product OCFA composition. The per gram biomass fed metric could be translated to different reactors, while the g/L measurement may be reactor or process specific.

In this example, as shown in Table 5, using this same comparison, heptadecanoic acid (C17) content results are shown to increase from just a trace amount to greater than about 5% (8%) TFA. Further, in this implementation, while the concentration of DHA (C22:6) is shown to decrease from about 37% to about 25%, the presence of DHA in the resulting biomass may comprise a significant source of this oil, when compared to synthetically produced anaplerotic oils (e.g., containing odd-chain fatty acids that can improve anaplerotic conditions), which typically lack DHA entirely.

That is, for example, tripentanoin and triheptanoin (short and medium-sized odd-chain fatty acids) are currently the primary concentrated sources of odd chain fatty acids available. However, these molecules are produced synthetically and do not resemble any naturally available oil. For example, the odd-chain triheptanoin does not exist naturally, and is obtained through chemical synthesis from glycerol and heptanoic acid (C7:0). In contrast, algal anaplerotic oil can be produced naturally, as described above; and the resulting oils can contain the same odd chain fatty acids that are present in dairy products (e.g., and other natural sources), for example, which may allow for appropriate introduction into a human diet. As an example, the anaplerotic oil production, described herein, can be from algae sources, and is believed to be less costly than synthetic production because it does not utilize modified fatty acids and chemical transesterification.

Example 3—Propionic Acid can Inhibit Growth at Various Concentrations

As another example, a strategy can be devised for propionate feeding to *Aurantiochytrium acetophilum* HS399 cultures, and the results can illustrate the effect on growth and propionate deposition in the lipid fraction. In this example, five treatments (P0, P3, P0+3, P0+1+1+1, P0+2+2+2) can be used, and respective treatments can receive a different amount of propionate, which is dependent on incubation time. In this example, treatment P3 receives 3 g/L propionate on day 0 at the beginning of the protein phase, while P0+3 receives 3 g/L propionate on day 1 at the beginning of the end of the protein phase-beginning of the lipogenic phase. The treatment P0+1+1+1 receives 1 g/L propionate on day 1, 2 and 3, and treatment P0+2+2+2 receives 2 g/L on day 1, 2 and 3 in an attempt to reduce the high residual propionate available during lipogenesis. Respective Erlenmeyer flasks (250 mL) are inoculated (1% v/v) in triplicates with a 24 h old culture of *A. acetophilum* HS399 and incubated in an orbital shaker at 180 rpm and 27° C.

Respective Erlenmeyer flasks contain 100 mL of a medium supplemented with (g/L): dextrose (100), ammonium acetate (4.6), NaCl (12.5), $MgSO_4$ $7H_2O$ (2.5), $KH_2PO_4$ (0.5), KCl (0.5) and $CaCl_2$ (0.1). This medium also contains trace element solution (5 ml/L) and vitamin solution (1 ml/L). The trace element solution contains (g/L): EDTA di-sodium salt (6), $FeCl_3$ $6H_2O$ (0.29), $H_3BO_3$ (6.84), $MnCl_2$ $4H_2O$ (0.86), $ZnCl_2$ (0.06), $CoCl_2$ $6H_2O$ (0.026), $NiSO_4$ $6H_2O$ (0.052), $CuSO_4$ $5H_2O$ (0.002), $Na_2MoO_4H_2O$ (0.005). The vitamin solution contains (mg/L): thiamine (100), biotin (0.5) and cyanocobalamin (0.5).

Figure 15:
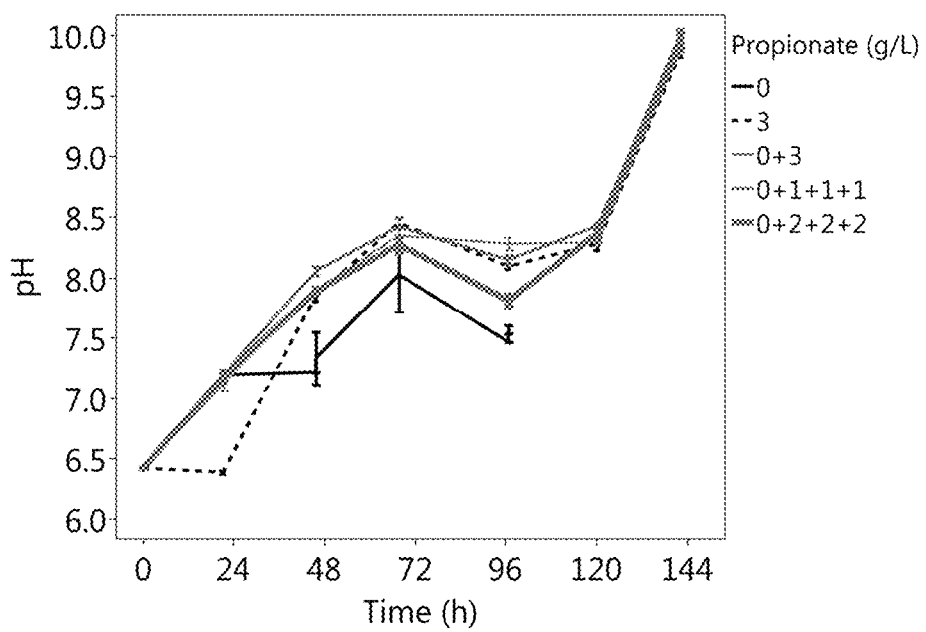
FIG. 15 is a line graph depicting the culture pH-drift of *Aurantiochytrium acetophilum* HS399 fed with varying levels of propionate.

In this example, respective culture materials are autoclaved (e.g., 121° C., 15 min) and the media is filter sterilized before use. A propionic acid stock solution (200 g/L) can be used as the fed propionic acid. Daily samples are collected to analyze the cell dry weight, residual glucose, culture pH (see FIG. 15), and lipid and fatty acid composition of the cultures. Cell dry weights are analyzed by filtration (e.g., 0.2 µm filter media) using a vacuum and washed with a solution of ammonium bicarbonate. Residual glucose is analyzed using a colorimetric method based on glucose peroxidase activity. Biomass for lipid analysis is centrifuged and washed using purified water. The washed biomass is freeze dried. Total lipids are analyzed using Folch method (AOAC 996.06) and the FAMES are analyzed by gas chromatography and flame ionization detection using nonadecanoic (C19:0) acid as an internal standard.

Figure 13:
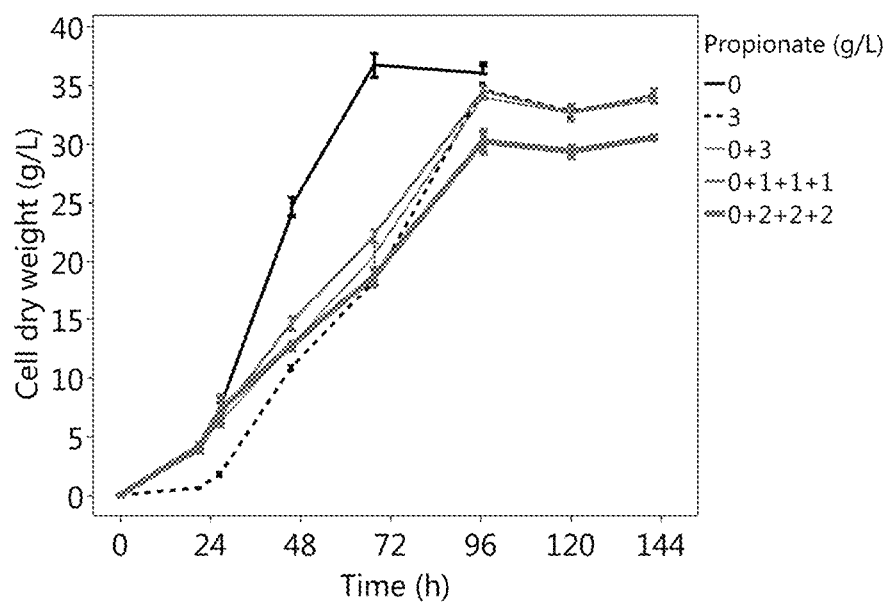
FIG. 13 is a line graph depicting cell dry weight for an *Aurantiochytrium acetophilum* HS399 culture fed varying amounts of propionate.
Figure 14:
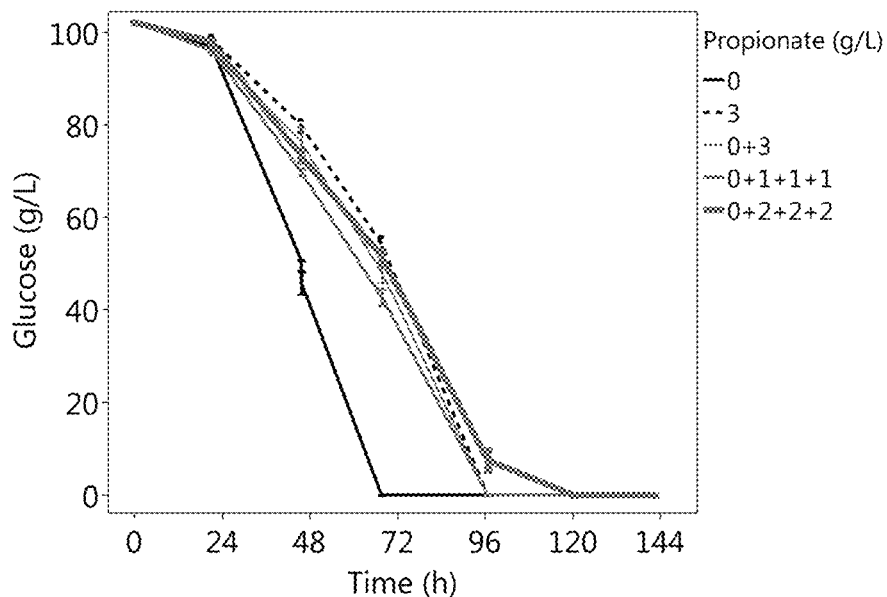
FIG. 14 is a line graph depicting *Aurantiochytrium acetophilum* HS399 residual glucose consumption in response to propionate supplementation.

As shown in FIGS. 13 and 14 respectively, the resulting cell dry weight and resulting residual glucose illustrate that feeding 3 g/L propionic acid (P3) provides a lag in growth in the first 24 h. Further, the results illustrate that this lag was mitigated by feeding 3 g/L at the end of the protein phase-beginning of lipogenesis (day 1). Additionally, the results illustrate that initial (24 h) growth for P0+3 was similar to the growth of the control treatment P0, and the growth lag observed in the P3 treatment was mitigated.

Table 7, below, provides the lipid and fatty acid analysis results, and Table 8 provides the propionate deposition. As shown in these tables, postponing the propionate feed to the lipogenic phase (P0+3) resulted in a higher production of OCFAs (27.4 TFA) and higher propionate deposition (59.3±1.1% of total) than when feeding the propionate initially (P3), at the beginning of the protein phase (25.2% TFA and 52.2±0.7% of total). Further, the results suggest that propionic acid lost through its oxidation by the citric acid cycle can be higher during the protein phase than the lipid phase. As an example, this may demonstrate that waiting for lipogenesis to feed propionate can help to mitigate toxicity and can help improve propionate incorporation into the OCFAs. Additionally, the results illustrate that OCFAs acid productivity may increase by approximately 20% by feeding propionate merely during lipogenesis (from 1.18±0.02 at P3 to 1.18±0.02 g OCFAs/L d for P0+3).

As an example, results suggest that fractionating the 3 g/L of propionate into three daily dosage of 1 g/L (P0+3 vs. P0+1+1+1) may not reduce the impact of propionic acid toxicity in *A. acetophilum* HS399 growth, as illustrated in FIG. 13. In this example, residual concentrations as low a 1 g/L may provide some growth inhibition. Further, the results obtained with P0+2+2+2, suggest that 6 g propionate/L produces a desirable amount (e.g., higher) of OCFAs in *A. acetophilum* HS399 flask cultures, which may translate into 0.18 g of propionate per g of biomass produced for other growth platforms.

TABLE 7

Total lipids and fatty acid profile at time of harvest (96 h)

| | Propionate (g/L) | | | | |
|---|---|---|---|---|---|
| | 0 | 3 | 0 + 3 | 0 + 1 + 1 + 1 | 0 + 2 + 2 + 2 |
| Harvest & Sample Day | 4 | 6 | 6 | 6 | 6 |
| Total Lipids (% DW) | 79.3 ± 0.6 | 78.0 ± 0.0 | 79.5 ± 0.5 | 79.7 ± 0.6 | 76.0 ± 1.0 |
| Ash (% DW) | | | | | |
| Total Fatty Acids (% DW) | 69.7 ± 1.4 | 64.8 ± 1.2 | 66.0 ± 2.2 | 67.2 ± 5.0 | 63.5 ± 1.6 |
| Fatty Acid Profile (% TFA) | | | | | |
| 13:0 | 0.0 ± 0.0 | 1.1 ± 0.0 | 1.0 ± 0.0 | 1.1 ± 0.0 | 1.8 ± 0.0 |
| 14:0 | 4.1 ± 0.1 | 2.3 ± 0.0 | 2.2 ± 0.1 | 2.0 ± 0.0 | 1.1 ± 0.0 |
| 15:0 | 0.2 ± 0.0 | 20.1 ± 0.2 | 22.1 ± 0.2 | 23.6 ± 0.4 | 42.3 ± 0.7 |
| 16:0 | 47.1 ± 0.4 | 31.3 ± 0.2 | 29.1 ±0.3 | 27.1 ± 0.2 | 7.6 ± 0.2 |
| 17:0 | 0.0 ± 0.0 | 4.0 ± 0.0 | 4.3 ± 0.1 | 4.6 ± 0.1 | 8.8 ± 0.1 |
| 18:0 | 1.4 ± 0.0 | 1.1 ± 0.0 | 1.0 ± 0.0 | 0.9 ± 0.0 | 0.2 ± 0.0 |
| 22:5 (n-6) | 8.1 ± 0.0 | 6.1 ± 0.0 | 5.8 ± 0.0 | 5.8 ± 0.0 | 4.2 ± 0.2 |
| 22:6 (n-3) | 36.5 ± 0.3 | 30.9 ± 0.2 | 31.5 ± 0.4 | 31.9 ± 0.2 | 30.1 ± 0.4 |
| Other FA | 2.3 ± 0.1 | 2.7 ± 0.1 | 2.6 ± 0.0 | 2.7 ± 0.1 | 3.3 ± 0.1 |
| OCFA (% TFA) | 0.4 ± 0.0 | 25.5 ± 0.2 | 27.6 ± 0.1 | 29.2 ± 0.4 | 53.5 ± 0.8 |

TABLE 8

Impact of propionate feeding regime on propionate deposition and productivity of OCFAs at 120 h incubation.

| Propionate (g/L) | PA Feeding Rate ($g_{PA}/g_{Biomass}$) | Propionate deposition (%) | OCFA Productivity (g/L/d) |
|---|---|---|---|
| 0 (Day 4) | 0.00 ± 0.00 | 0.0 ± 0.0 | 0.0 ± 0.0 |
| 3 (Day 5) | 0.09 ± 0.00 | 52.2 ± 0.7 | 1.04 ± 0.01 |
| 0 + 3 (Day 5) | 0.09 ± 0.00 | 59.3 ± 1.1 | 1.18 ± 0.02 |
| 0 + 1 + 1 + 1 (Day 5) | 0.09 ± 0.00 | 59.6 ± 1.4 | 1.19 ± 0.03 |
| 0 + 2 + 2 + 2 (Day 5) | 0.20 ± 0.00 | 46.7 ± 0.9 | 1.86 ± 0.04 |

Example 4—Modeling Propionic Acid Toxicity

Figure 16:
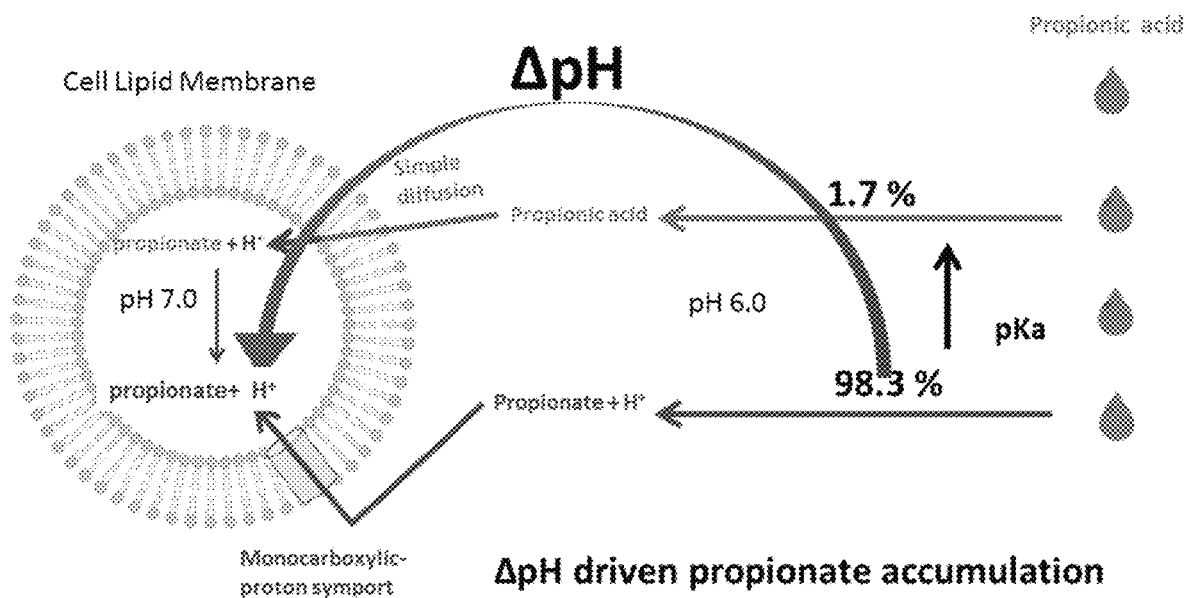
FIG. 16 is a schematic diagram illustrating the active and passive transport of propionic acid inside the cell. The pH gradient across the cell controls the passive uptake of propionic acid by the cell.

In one aspect, the uptake activity of propionate as an organic carbon source by microalgae may be dependent on the culture's pH. For example, when propionic acid is fed to a culture that is growing at a pH of 7, the residual organic acid can be mostly dissociated in the propionate form (propionic pKa=4.88), with only a minor amount remaining undissociated. In this aspect, while the propionate and free proton form enters the microalgae cell through a monocarboxylic symport structure, propionic acid is membrane permeable and may be diffused directly into the microalgae cell. Therefore, in this aspect, the uptake of propionate can be controlled by the cell, and the uptake of propionic acid may not be controlled by the cell. As an example, the uncontrolled uptake of propionic acid presumably lowers the internal *Aurantiochytrium* cell pH; in turn, the cell attempts to maintain its pH homeostasis by pumping protons out of the cell. In this example, a build-up of propionate inside the cell can result, which is proportional to the pH gradient between the intracellular and the extracellular (see FIG. 16). Therefore, in one implementation in this aspect, the internal propionate concentration, which could be used to measure propionic cell toxicity, may be calculated using at least the external culture pH, the internal cell pH, and the residual acetate concentration in the culture. In one implementation, the change in pH may be calculated with the following equation derived from the Henderson and Hasselbalch equation:

$$\Delta pH = pH_i - pH_O = \log\left(\frac{[P_i]}{[P_O]}\right)$$

In this implementation, pHi=pH inside the cell, pHo=pH outside the cell, P=propionate, O=outside cell, I=inside cell. Assumptions made in this calculation may include: the impact of the ionic strength in the propionic acid dissociation constant as negligible, propionic acid but not propionate is membrane permeable, and there are no other protection mechanisms involved in the regulation of cell pH. The relationship may be illustrated with the non-limiting Example 1 (above), which shows that propionate may be substantially lethal at residual (extracellular) concentrations of ~15 g/L and a pH of 6. The above-mentioned model can be used to translate this Example 1 into an intracellular propionate concentration of 176 g/L, providing a value that could be translated at different pHs and residual concentrations. Further, the relationship may be illustrated by the non-limiting Example 2 (above), which shows that propionate may be substantially non-lethal, but growth inhibitory, at concentrations as low as 1 g/L at pH of 7. The above-mentioned model can be used to translate Example 2 into an intracellular propionate concentration of 1 g/L, providing a value that could be translated at different pHs and residual concentrations. Therefore, in this implementation, the model can help provide an understanding of the impact of medium pH in propionate toxicity and can provide a tool to model propionic acid toxicity that could be used to improve a process to optimize OCFAs production.

Example 5—Propionic Acid/pH-Auxostat LED Strategy to Produce OCFA

In one implementation, a propionic acid/pH-auxostat led strategy may be used to produce anaplerotic oils containing odd chain fatty acids using the microalgae *A. acetophilum* HS399. In this implementation, for example, three treatments can be fed propionic acid as titrant to maintain pH at a desired level (e.g., organic acids: Propionic acid-pH7, Propionic acid-pH6 and Propionic acid-pH5). Further, a control treatment can be fed acetic acid at pH 7 (e.g., Acetic acid-pH7). In this implementation, initially (24 h incubation), the culture pH may not be controlled, and the pH of the respective treatments can drift from 7.5 to 8. After 24 h incubation, the desired pH set point of each treatment can be set using the respective organic acids.

In this implementation, for example, bubble column reactors (1.3 L) are inoculated (1% v/v) in triplicates with a 24 h old culture of *A. acetophilum* HS399. The cultures are aerated at 1.4 vvm and maintained at 27° C. under axenic conditions. The bubble columns contain 700 mL of a medium supplemented with (g/L): dextrose (40), ammonium acetate (1.1), NaCl (12.5), $MgSO_4$ $7H_2O$ (2.5), $KH_2PO_4$ (0.5), KCl (0.5) and $CaCl_2$ (0.1). This medium also contains a trace element solution (5 ml/L) and a vitamin solution (1 ml/L). The trace element solution can contain (g/L): EDTA di-sodium salt (6), $FeCl_3$ $6H_2O$ (0.29), $H_3BO_3$ (6.84), $MnCl_2$ $4H_2O$ (0.86), $ZnCl_2$ (0.06), $CoCl_2$ $6H_2O$ (0.026), $NiSO_4$ $6H_2O$ (0.052), $CuSO_4$ $5H_2O$ (0.002), $Na_2MoO_4H_2O$ (0.005). The vitamin solution can contain (mg/L): thiamine (100), biotin (0.5) and cyanocobalamin (0.5).

The respective culture materials can be autoclaved (121° C., 15 min) and the media can be filter sterilized before use. In this example, propionic and acetic acid are diluted to 3% w/w and added to the acid container, from which the cultures are fed through a peristaltic pump in response to the pH drift above their set point. Daily samples can be collected to analyze the cell dry weight, residual glucose, culture pH, and lipid and fatty acid composition of the cultures. Cell dry weights are analyzed by filtration (0.2 µm filter media) using a vacuum and washed with a solution of ammonium bicarbonate. Residual glucose is analyzed from culture supernatant (5000 g; 5 min) using a colorimetric method based on glucose peroxidase activity. Residual acetate and propionate are analyzed by HPLC using external standard. Biomass for lipid analysis can be centrifuged and washed using purified water; and the washed biomass is freeze dried. Total lipids are analyzed using Folch method (AOAC 996.06), and the FAMEs are analyzed by gas chromatography and flame ionization detection using nonadecanoic (C19:0) acid as an internal standard.

Figure 17:
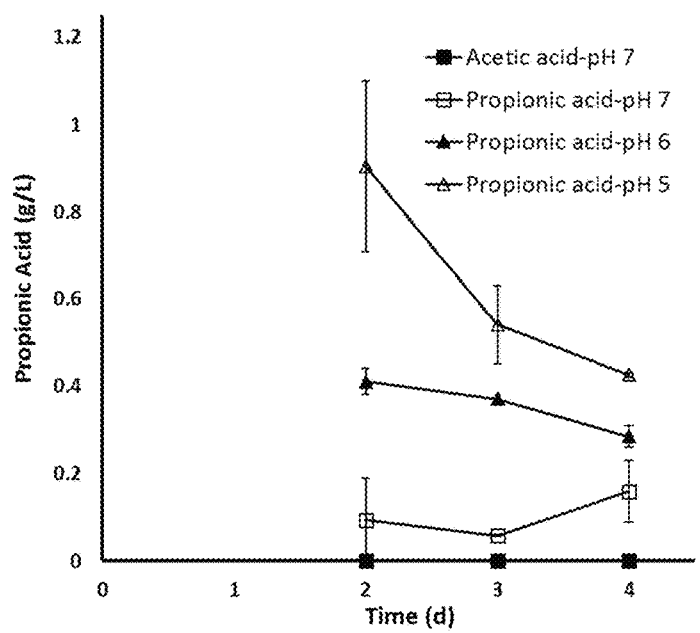
FIG. 17 is a line graph depicting the residual propionic acid as a function of pH in a pH-auxostat culture of *Aurantiochytrium acetophilum;*
Figure 18:
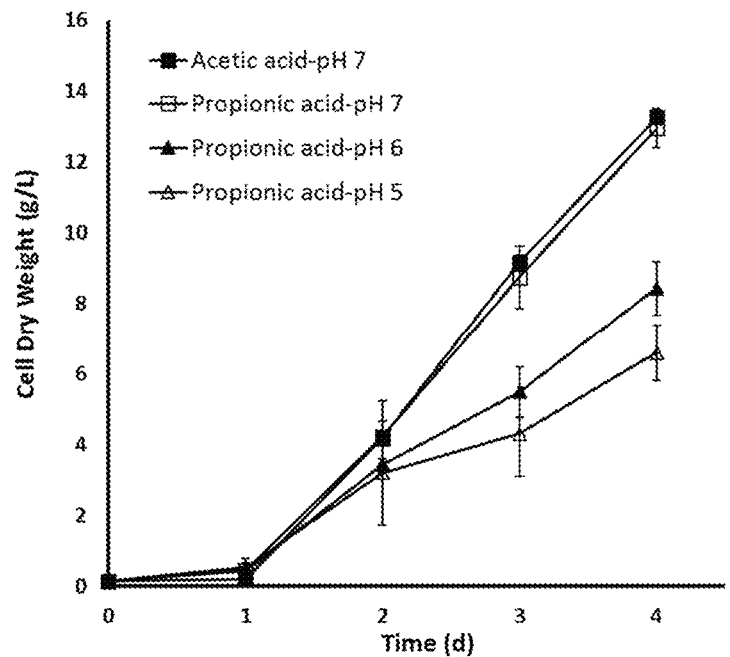
FIG. 18 is a line graph depicting dry cell weight for an *Aurantiochytrium acetophilum* HS399 culture which shows the impact of pH and an organic acid feeding regime on HS399 growth.
Figure 19:
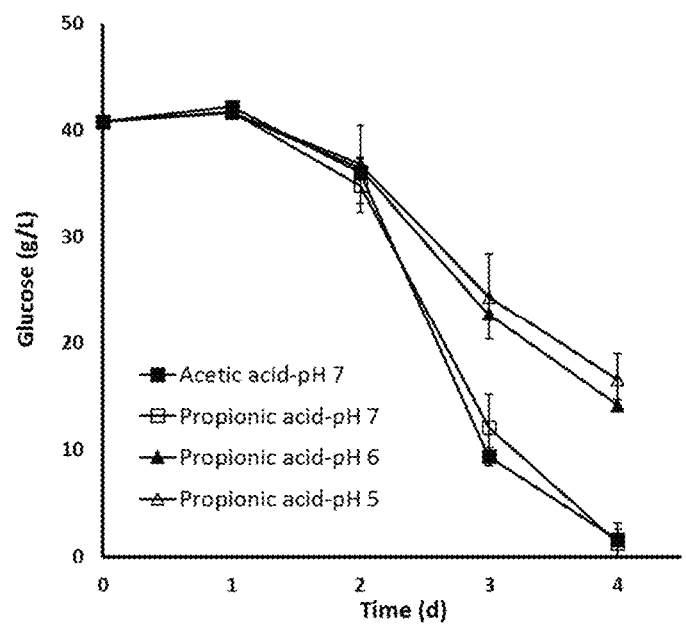
FIG. 19 is a line graph depicting residual glucose as a function of the pH-set point in a pH-auxostat culture of *Aurantiochytrium acetophilum* HS399.

Residual propionate results are provided in FIG. 17, illustrating that the pH-auxostat strategy was able to successfully maintain the propionate levels at the pH 5 and 6 set points. Further, as illustrated in FIG. 17, the treatments comprising a pH 7 set point did not appear to have sufficient residual propionate or acetate to identify whether the organic acid was present during the demonstration, and therefore they were not fed on demand, but ad libitum. The results of this example illustrate that using a propionic acid-pH7 pH-auxostat system may have interrupted the propionic acid feeding due to the displacement of residual propionate. As illustrated by the cell dry weight data represented in FIG. 18, propionic acid was not growth inhibitory. However, as illustrated by the data in Table 9, below, OCFA (6.3% TFA) may not be accumulated to levels observed previously in the flask (>50% TFA) or at lower pH treatments, likely due to the lack of propionic acid. Therefore, in one implementation, at a higher pH, supplementation with sodium propionate, or target alkalization of the media, may be used to provide for the presence of residual propionate in the batch even at high pH-set points. These results indicate that the lower pH set points can be highly growth inhibitory, as shown by the cell dry weight data (FIG. 18) and glucose analyses (FIG. 19). These results indicate that inhibition may be higher at lower pHs, as may be predicted by the model described in Example 4 (Table 10 below).

TABLE 9

Lipid and fatty acids analyses from the pH auxostat

|  | Acetic acid-pH 7 | | Propionic acid-pH 7 | | Propionic acid-pH 6 | | Propionic acid-pH 5 | |
| --- | --- | --- | --- | --- | --- | --- | --- | --- |
| Consumed Propionate (g/L) | 0.0 ± 0.0 | | 1.0 ± 0.1 | | 2.4 ± 0.1 | | 2.3 ± 0.2 | |
| Propionic Acid Deposited (%) | 0.0 ± 0.0 | | 24.7 ± 1.0 | | 40.3 ± 1.6 | | 30.9 ± 2.0 | |
| Total Lipids (% CDW) | 89.5 ± 0.5 | | 87.5 ± 1.5 | | 79.5 ± 1.5 | | 75.0 ± 3.0 | |
| Total Fatty Acid (% CDW) | 71.9 ± 5.2 | | 70.3 ± 2.8 | | 63.4 ± 0.3 | | 59.2 ± 3.1 | |
| Fatty Acid | (% TFA) | (% DW) | (% TFA) | (% DW) | (% TFA) | (% DW) | (% TFA) | (% DW) |
| C11:0 | 0.0 ± 0.0 | 0.0 ± 0.0 | 0.0 ± 0.0 | 0.0 ± 0.0 | 0.1 ± 0.1 | 0.1 ± 0.1 | 0.0 ± 0.0 | 0.0 ± 0.0 |
| C13:0 | 0.0 ± 0.0 | 0.0 ± 0.0 | 0.0 ± 0.0 | 0.0 ± 0.0 | 2.2 ± 0.3 | 1.4 ± 0.2 | 2.1 ± 0.1 | 1.2 ± 0.0 |
| C14:0 | 3.2 ± 0.0 | 2.3 ± 0.2 | 2.9 ± 0.1 | 2.0 ± 0.1 | 1.3 ± 0.0 | 0.8 ± 0.0 | 1.1 ± 0.1 | 0.7 ± 0.1 |
| C15:0 | 0.0 ± 0.0 | 0.0 ± 0.0 | 7.3 ± 1.7 | 5.1 ± 1.0 | 50.6 ± 0.3 | 32.1 ± 0.0 | 51.6 ± 1.7 | 30.5 ± 0.6 |
| C16:0 | 56.4 ± 0.0 | 40.6 ± 2.9 | 49.3 ± 1.7 | 34.7 ± 2.6 | 9.6 ± 0.8 | 6.1 ± 0.5 | 8.1 ± 1.8 | 4.8 ± 1.3 |
| C17:0 | 0.0 ± 0.0 | 0.0 ± 0.0 | 1.7 ± 0.4 | 1.2 ± 0.2 | 7.2 ± 0.4 | 4.6 ± 0.3 | 7.3 ± 0.1 | 4.3 ± 0.3 |
| C18:0 | 1.3 ± 0.0 | 1.0 ± 0.1 | 1.1 ± 0.0 | 0.8 ± 0.1 | 0.3 ± 0.0 | 0.2 ± 0.0 | 0.1 ± 0.1 | 0.1 ± 0.1 |
| C20:3n6 & C21:0 | 0.2 ± 0.0 | 0.2 ± 0.0 | 0.1 ± 0.1 | 0.1 ± 0.1 | 0.2 ± 0.2 | 0.1 ± 0.1 | 0.3 ± 0.0 | 0.2 ± 0.0 |
| C20:5n3 & C22:0 | 0.4 ± 0.0 | 0.3 ± 0.0 | 0.4 ± 0.0 | 0.3 ± 0.0 | 0.4 ± 0.0 | 0.3 ± 0.0 | 0.5 ± 0.0 | 0.3 ± 0.0 |
| C22:5n6 DPA | 6.7 ± 0.0 | 4.8 ± 0.4 | 6.5 ± 0.0 | 4.6 ± 0.2 | 4.7 ± 0.0 | 3.0 ± 0.0 | 4.4 ± 0.2 | 2.6 ± 0.2 |
| C22:6n3 | 31.6 ± 0.0 | 22.7 ± 1.6 | 30.7 ± 0.1 | 21.6 ± 0.9 | 23.4 ± 0.4 | 14.8 ± 0.2 | 24.7 ± 0.6 | 14.6 ± 0.4 |
| OCFA (% TFA) | 0.0 ± 0.0 | 0.0 ± 0.0 | 9.0 ± 2.1 | 6.3 ± 1.2 | 60.0 ± 0.2 | 38.0 ± 0.1 | 60.9 ± 1.7 | 36.0 ± 0.9 |

TABLE 10

The intracellular propionate, represented as an indicator of propionate toxicity for each treatment, was calculated from the propionate residual concentration and the pH set point using model described in Example 4.

|  | Actual Values Average Residual Propionic Acid (g/L) | Theoretical Values D1-D4 Average Internal Propionic Acid (g/L) |
| --- | --- | --- |
| Acetic acid-pH 7 | 0.0 ± 0.0 | 0.00 |
| Propionic acid-pH 7 | 0.1 ± 0.1 | 0.13 |
| Propionic acid-pH 6 | 0.4 ± 0.1 | 4.18 |
| Propionic acid-pH 5 | 0.6 ± 0.2 | 56.70 |

Example 6—Single Stage Approach to Producing OCFA

In another implementation, a New Brunswick 10 L Bioflo Pro 300 fermenter (Eppendorf) can be used to provide an improvement in the productivity of OCFAs accumulation, previously identified in flasks and bubble columns. In this implementation, a bioprocess can be devised to incorporate one or more portions of one or more techniques described herein. In this implementation, a propionic acid/pH-auxostat strategy can be adopted after day 1 to induce the production of OCFAs. As an example, in this implementation, the pH-auxostat is operated at a pH set point of 6.5 to mitigate propionic toxicity. The pH-auxostat is activated through the addition of 0.5 g/L of potassium propionate to provide residual propionate availability during the culture. A control treatment can be provided with propionate, to be used as comparison. Fermenters containing 5 L of fresh media are inoculated (1% v/v) in triplicates with a 24 h old culture of *A. acetophilum* HS399. The fermenters are aerated at 0.5 vvm and are maintained at 27° C. under axenic conditions. A stirring speed is increased in response to identified dissolved oxygen values below 10% saturation, from 200 rpm up to 1000 rpm.

In this implementation, for example, the 5 L of batch media can contain (g/L): corn syrup D95 (31), ammonium acetate (19.5), $MgSO_4$ $7H_2O$ (2.5), $KH_2PO_4$ (2.5), KCl (1) and $CaCl_2$ (0.2). This medium can also contain a trace element solution (25 ml/L) and vitamin solution (5 ml/L). The trace element solution contains (g/L): EDTA di-sodium salt (6), $FeCl_3$ $6H_2O$ (0.29), $H_3BO_3$ (6.84), $MnCl_2$ $4H_2O$ (0.86), $ZnCl_2$ (0.06), $CoCl_2$ $6H_2O$ (0.026), $NiSO_4$ $6H_2O$ (0.052), $CuSO_4$ $5H_2O$ (0.002), $Na_2MoO_4H_2O$ (0.005); and the vitamin solution contains (mg/L): thiamine (100), biotin (0.5) and cyanocobalamin (0.5). In this example, the fermenter is fed another 5-6 L of a medium containing (g/L): ammonium phosphate (2.5), ammonium hydroxide (29% pure) (15.2), corn syrup DE95 (1143). This medium can also contain a trace element solution (25 ml/L) and a vitamin solution (5 ml/L).

In this example, this medium is fed in a DO-stat mode in response to dissolved oxygen values detected above 15% saturation. As an example, the dissolved oxygen values can trigger a feeding pulse of 0.3 ml/L min that lasts 102 min. The pH is maintained at 5.8 using NaOH, while the batch ammonia is consumed. The pH can drift to higher values when the residual ammonia is substantially exhausted from the fermenter. At substantial residual ammonia exhaustion, the pH can be controlled with propionic acid at a pH 6.4, in some examples, while the pH of the control treatment may drift up to 7-8 without titration. Culture materials and media can be autoclaved (e.g., 121° C., 15 min) while separating the nitrogen and the carbon source. Foam can be controlled (e.g., automatically) through the addition of (<1 ml/L) Hodag antifoam.

In this implementation, samples can be collected daily to analyze the cell dry weight, residual glucose, culture pH, and lipid and fatty acid composition of the cultures. Cell dry weights can be analyzed by filtration (e.g., 0.2 μm filter media) using a vacuum, and washed with a solution of ammonium bicarbonate. Residual glucose can be analyzed from culture supernatant (e.g., 5000 g; 5 min) using a colorimetric method based on glucose peroxidase activity. Residual acetate and propionate can be analyzed by HPLC using an acceptable external standard. The biomass for lipid analysis can be centrifuged and washed using purified water, and the washed biomass can be freeze dried. Total lipids are analyzed using Folch method (AOAC 996.06) and the FAMEs are analyzed by gas chromatography and flame ionization detection using nonadecanoic (C19:0) acid as an internal standard.

Figure 20:
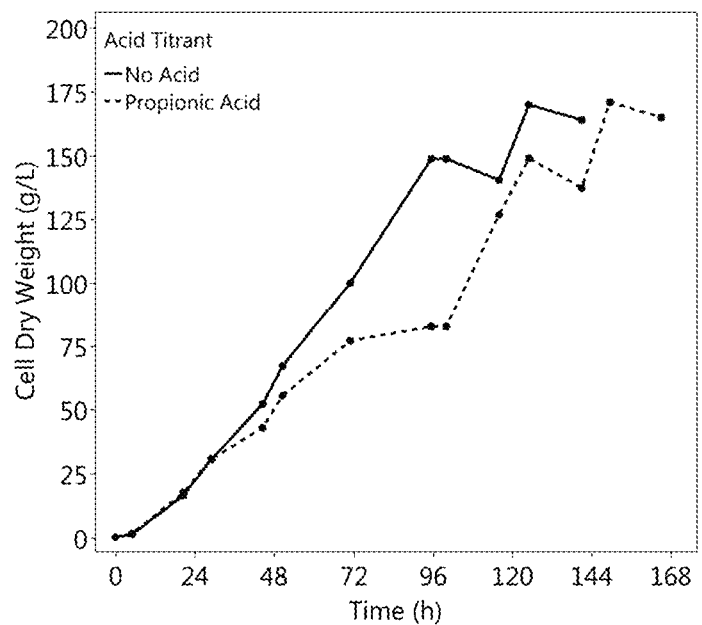
FIG. 20 is a line graph comparing the cell dry weight for an *Aurantiochytrium acetophilum* HS399 culture fed propionic acid and an *Aurantiochytrium acetophilum* HS399 culture that is not.
Figure 21:
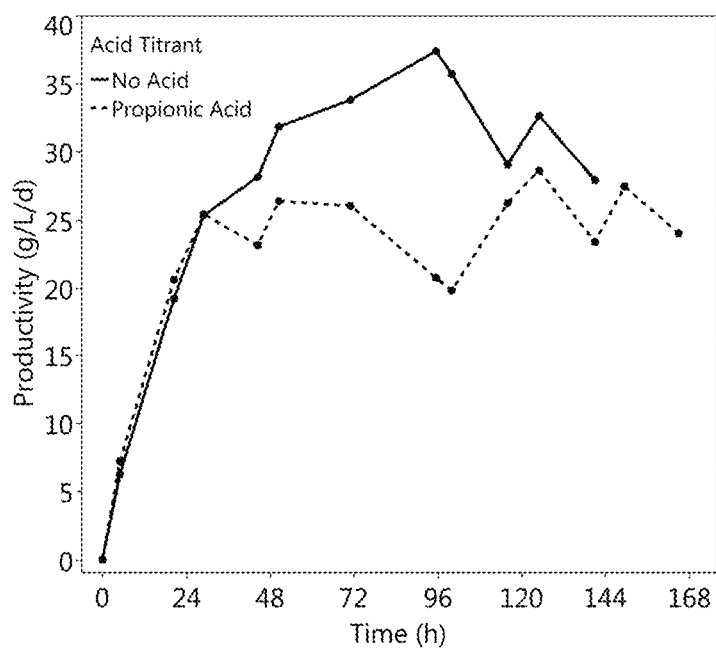
FIG. 21 is a line graph comparing the cumulative productivities for an *Aurantiochytrium acetophilum* HS399 culture fed propionic acid and an *Aurantiochytrium acetophilum* HS399 culture that is not.
Figure 22:
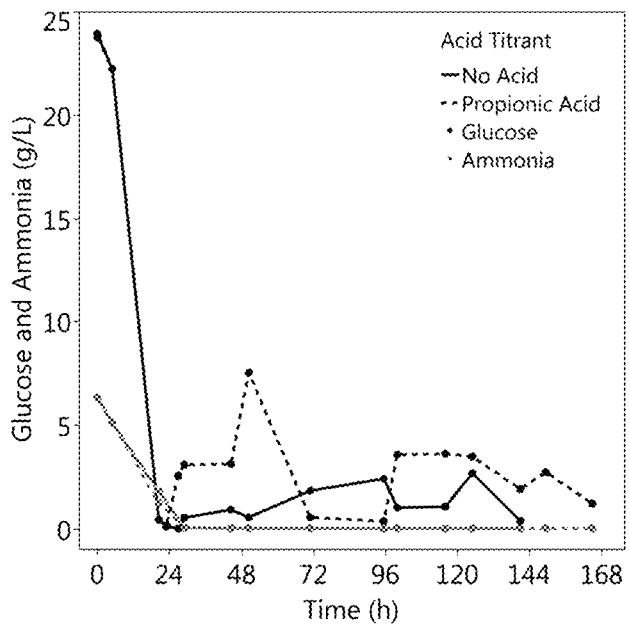
FIG. 22 is a line graph depicting the residual glucose and ammonia levels.
Figure 23:
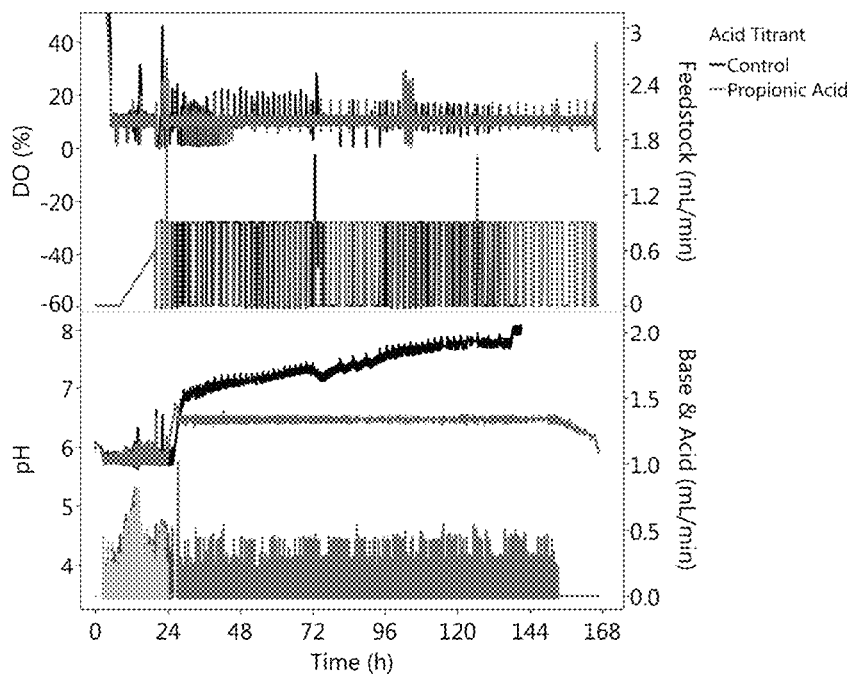
FIG. 23 is a graph showing online monitoring of the fermenter HS399 cultures with other parameters such as dissolved oxygen, feedstock and titrant pumping rate, and pH control.
Figure 24:
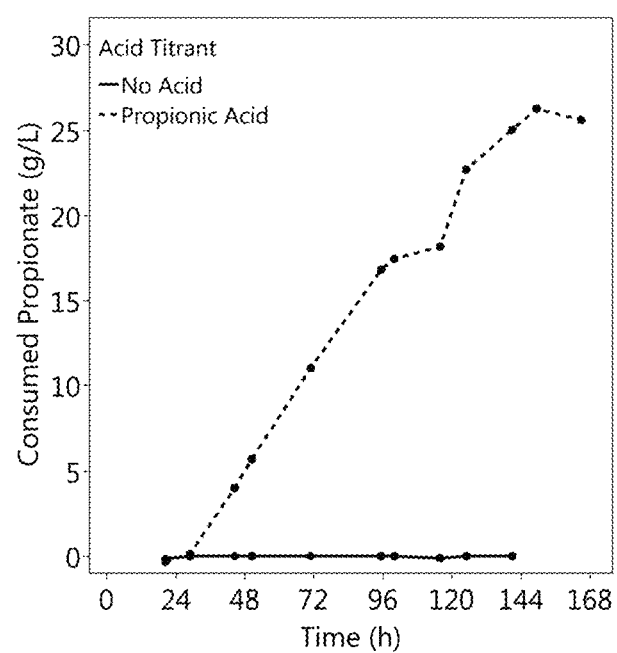
FIG. 24 is a line graph comparing the total propionate consumption of an *Aurantiochytrium acetophilum* HS399 culture fed propionic acid and an *Aurantiochytrium acetophilum* HS399 culture that is not.

Example results of the cell dry weights, in this implementation, are shown in FIG. 20. As an example, the results illustrate that, even though the propionic acid titration slightly inhibited *A. acetophilum* HS399 growth compared to no propionic acid titration, the cultures presented 170 g/L cell dry weight, and accumulated lipids at 70% DW, with 60% TFA being OCFAs. The results illustrated in FIG. 21 show that the average cumulative productivities are approximately 30 g/L/d, which translates into 10 g/L/day of OCFAs. In this implementation, as illustrated by these results, the example bioprocess can maintain the residual glucose and ammonia at desired levels, as illustrated by FIG. 22, and other cultivation parameters at desired levels, as shown in FIG. 23. As illustrated in FIG. 24, providing results of total propionate consumed during the process in this implementation, the process provided a consumption of 0.155 g of propionic per gram of biomass, which is in agreement with the values observed in flask (Example 2). In this implementation, as in previous implementations, the results of the OCFAs produced by the control treatment were negligible.

Fungi/Yeast

In another aspect, techniques and systems can be devised, as described herein, for a natural method of improving the production of OCFAs in microalgae and other microorganisms, like yeast/fungi, that do not utilize genetic modification. A process is disclosed herein for the production of an oil rich in OCFA. As one example, oil rich in OCFA may be produced at 28 g oil/L/day, and at 31 g/L/day or more. For example, such processes can produce a triacylglyceride containing OCFAs of 40% of TFA or more, and up to approximately 67% TFA. In one example, the cultures may achieve a final biomass yield of approximately 126 g/L.

In addition to *A. acetophilum* HS399 microalgae, as described above, certain microorganisms (e.g., yeast/fungus) can produce a variety of fatty acids, the composition of which can vary among different strains of microorganisms. As an example, *Yarrowia lipolytica* is considered to be an oleaginous yeast that can accumulate large amounts of lipids. Yeast species are typically described as "oleaginous" if the lipids they accumulate account for more than 20% of their biomass. For *Y. lipolytica*, the amount of lipid accumulation is dependent on the strain and the carbon source, along with growth conditions. Under optimal growth conditions, some fed-batch cultures of *Y. lipolytica* can store 43% lipids of their cell dry weight (CDW) in continuous fermentations using industrial glycerol and may store up to 54% lipids of their CDW in batch cultures on a stearin-based medium. In these examples, most of the lipids accumulating in *Y. lipolytica* are triacylglycerols rather than free fatty acids (FFA), with C16 and C18 compounds being the most abundant, with other fatty acids present in trace amounts.

The trace fatty acids of *Y. lipolytica* can include pentadecanoic acid (C15:0) and heptadecenoic acid (C17:1 n-8) (e.g., at <0.3% TFA). The trace fatty acids, including these two identified fatty acids, are typically ignored in the lipid profile reports for these organisms. Odd-chain fatty acids (OCFAs), including pentadecanoic acid and heptadecenoic acid (C17:1 n-8) are fatty acids that contain an odd number of carbon atoms in the structure. OCFAs are typically related to bacterial activity (e.g., propionic acid bacteria), and are less likely to be present in other microbes, such as yeast/fungi and microalgae, or plants.

The presence of trace amounts of OCFA in yeast/fungi suggests that the pathway responsible for the synthesis of OCFA may be present in yeast/fungi. Because of the composition of their fatty acid profile, and yeast/fungi ability to be grown rapidly, yeast/fungi such as *Y. lipolytica* may provide an attractive source of OCFA. Such microorganisms may be able to generate OCFA in a more rapid and concentrated manner than other known natural sources, such as milk fat (e.g., providing a more cost effective and efficient source of OCFAs). Yeast/fungi may also provide alternative OCFA, such as heptadecenoic acid (17:1 n-8), which may not be found in other food sources. Further, for example, yeast can produce OCFAs without highly unsaturated fatty acids, which can help mitigate undesirable flavors often associated with this type of oil. As an example, a benefit of using yeast/fungi in place of butter and other ruminant fat is the higher concentration of OCFA found in these types of yeast/fungi. In addition, as another example, benefit, yeast/fungi oil lacks residues of phytol or phytanic acid that are often present in ruminant fat. Consumption of phytol or phytanic acid can lead to health concerns in some individuals.

In one aspect, techniques can be devised that provide for an increased production of naturally occurring odd-chain fatty acids from yeast/fungi than might be generated from typical yeast/fungi. The resulting cultivated yeast/fungi and/or resulting isolated composition may be used individually as products or as an ingredient in a variety of products. As an example, yeast/fungi such as *Y. lipolytica* can be cultivated and produce a desirable fatty acid profile comprising OCFAs, which may be isolated through various extraction processes. In this example, the isolated oil containing the OCFAs may comprise a composition rich in OCFAs, such as pentadecanoic acid (C15:0) and heptadecenoic acid (C17:1 n-8). In one implementation, in this aspect, the yeast/fungi may be cultivated using an improved method that includes the presence of a complex media, which can promote increased production of the OCFAs. As one example, the cultivation media may comprise propionate. Propionate is a conjugate base of propionic acid and is a short-chain fatty acid often produced by gut flora in some animals.

In one implementation, *Y. lipolytica* can be cultivated with propionate to increase the amount of OCFA production. The following describes example implementations:

Example 7—Production of OCFA in *Yarrowia lipolytica*

Methods

Culture conditions. In one implementation, *Yarrowia lipolytica* ATCC18944 can be cultivated in triplicates (n=3) in a medium containing (g/L): glycerol (80), monosodium glutamate (5), yeast extract (1), NaCl (12.5), $MgSO_4$ (7), $H_2O$ (2.5), KCl (0.5), CaCl2 (0.1), $KH_2PO_4$ (0.5), trace metal solution (5 mL) and vitamin solution (1 mL). The trace element solution may contain (g/L): EDTA di-sodium salt (6), $FeCl_3$ $6H_2O$ (0.29), $H_3BO_3$ (6.84), $MnCl_2$ $4H_2O$ (0.86), $ZnCl_2$ (0.06), $CoCl_2$ $6H_2O$ (0.026), $NiSO_4$ $6H_2O$ (0.052), $CuSO_4$ $5H_2O$ (0.002), $Na_2MoO_4$ $2H_2O$ (0.005). The vitamin solution can be filter-sterilized (e.g., using 0.2 μm pore size filter) containing (mg L-1): thiamine (100), biotin (0.5) and cyanocobalamin (0.5) unless otherwise stated. In some implementations cyanocobalamin might be added to or subtracted from the medium formulation to change or impact propionic acid deposition in OCFA. In some implementations cobalt can be reduced or eliminated from the media to avoid synthesis of cyanocobalamin that could compromise propionic acid deposition. In one implementation, a concentration of the cyanocobalamin and/or cobalt in the culture medium can be below 0.4 µM.

*Y. lipolytica* cultures can be inoculated at 1% v/v in a 250 mL baffled Erlenmeyer flask containing 100 mL of the above-mentioned media. The flasks can be incubated in the dark in an orbital shaker at 180 rpm, 27° C. In this implementation, sodium propionate is fed batch every day according to respective treatments. As an example, treatment 0+0+2+2+2+2, is fed 2 g/L propionic acid at 48, 72, 96 and 120 hours, while treatment 0 is not fed any propionate at all.

Analyses. Cell dry weights can be obtained by drying samples that are previously vacuum filtrated (e.g., using 0.2 µm pore size filters). Residual propionate is analyzed directly by high performance liquid chromatography (HPLC). Lipids and total fatty acids are analyzed using a direct extraction, transesterification followed by gas chromatography (GC) and detection by flame ionization (FID). The different fatty acids are identified and quantified using appropriate internal and external standards.

Propionic acid deposition rate. Propionate consumption can be calculated based on the residual propionate on day 0 and subtracting the final residual propionate, to find the consumption amount. The total propionate deposited in the biomass is calculated based on the final cell dry weight, multiplied by the total fatty acid (TFA) ratio in biomass, multiplied by the OCFA ratio in TFA, and multiplied by the molar factor of propionate in odd chain fatty acid, averaged at 0.3. The propionate deposition rate can be calculated by dividing the propionate deposited by the propionate consumed and expressed as percent.

Results & Discussion

In this implementation, it is desirable to determine the capacity of *Yarrowia lipolytica* ATCC18944 to produce odd chain fatty acids (OCFAs) though the incorporation of propionate in the media. For example, propionate could be either incorporated in the lipids as OCFAs or oxidized through either the methylmalonate or methylcitrate pathways. Testing showed that the incorporation of medium propionic acid into *Y. lipolytica* fatty acids (i.e., OCFAs) may not be affected by the presence or absence of cyanocobalamin (see Table 11 below). Cyanocobalamin is cofactor on the methylmalonate pathway, thus the results indicate that this pathway might not be active in *Y. lipolytica*.

TABLE 11

Impact of cyanocobalamin in propionic acid deposition in *Yarrowia lipolytica* ATCC18944.

| | Cyanocobalamin (µM) | |
| --- | --- | --- |
| | 0.00037 | 0 |
| Daily propionate (g/L d) | 0 + 0 + 2 + 2 + 2 + 2 | 0 + 0 + 2 + 2 + 2 + 2 |
| Cell dry weight (g/L) | 5.3 | 6.0 |
| Consumed propionate (g/L) | 1.7 | 2.6 |
| Odd chain fatty acids (% DW) | 0.9 | 1.4 |
| Odd chain fatty acids (g/L) | 0.05 | 0.1 |

TABLE 11-continued

Impact of cyanocobalamin in propionic acid deposition in *Yarrowia lipolytica* ATCC18944.

| | Cyanocobalamin (µM) | |
| --- | --- | --- |
| | 0.00037 | 0 |
| Propionate (MW)/OCFA (MW) | 0.3 | 0.3 |
| Propionate deposition (%) | 0.83 | 0.99 |

Figure 25:
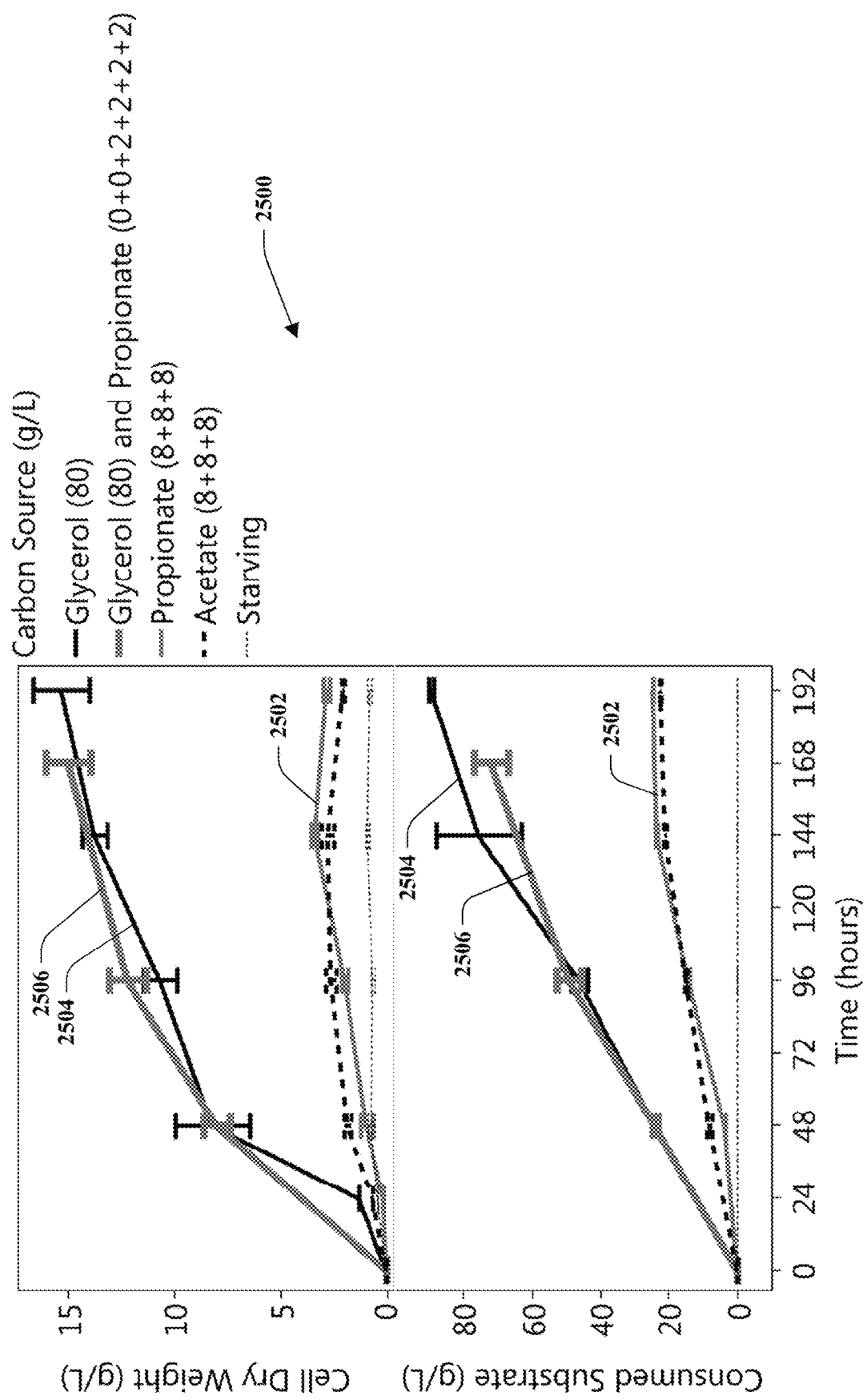
FIG. 25 is a graphical representation of results of growth and substrate consumption of *Yarrowia lipolytica* ATCC18944 using different carbon sources.

In this aspect, for example, the methylcitrate pathway is the only known anaplerotic pathway involved in propionic acid catabolism. FIG. 25 is a graphical representation 2500 of results of growth and substrate consumption of *Yarrowia lipolytica* ATCC18944 using different carbon sources. As illustrated in FIG. 25, *Y. lipolytica* may be able to grow on propionate 2502 as sole carbon source. Therefore, as an example, because anaplerosis is used to sustain the growth on propionate as a sole carbon source, these results suggest that propionate is primarily oxidized through the methylcitrate pathway. *Yarrowia lipolytica* growth on propionate 2502 is shown to be much lower than on glucose 2504, but this trend was corrected when both substrates 2506 (propionate and glycerol) were fed simultaneously.

In some implementations, fed batch propionate in the presence of glycerol may be used to increase cell growth rates and OCFAs production. As one example, as illustrated in Tables 12 and 13, below, for *Y. lipolytica*, propionic acid deposition rates in OCFAs may be relatively low (e.g., <3% TFA), which indicates that methylcitrate may readily oxidize propionic acid. In one implementation, in order to mitigate the propionic acid oxidative loss, the total amount of propionate fed batch can be increased gradually from 0.3 to 8 g/L, which can result in 13.3±1.3% TFA, 2.2±0.2% DW and 0.33 g/L OCFAs (see Table 13 below). The main OCFAs produced by *Yarrowia lipolytica* were the Omega-8 heptadecenoic acid (C17:1 n-8) and pentadecanoic acid (C15:0).

TABLE 12

Lipid and fatty acid analyses of *Yarrowia lipolytica* ATCC18944 fed increasing daily propionate concentrations

| | Time (hrs) | | | |
| --- | --- | --- | --- | --- |
| | 0 h | 168 | 168 | 168 |
| | | Daily propionate (g/L) | | |
| | Initial | 0 | 0.3 + 0.3 | 0 + 0.6 |
| Total Lipids (% DW) | | 24.7 ± 0.6 | 23.7 ± 3.5 | 21.7 ± 3.2 |
| Total Fatty Acids (% DW) | 10.6 | 24.0 ± 1.5 | 21.7 ± 2.5 | 21.3 ± 2.8 |
| Fatty Acid Profile (% TFA) | | | | |
| 15:0 | 0.00 | 0.3 ± 0.0 | 0.3 ± 0.0 | 0.4 ± 0.1 |
| 16:0 | 11.10 | 10.8 ± 0.1 | 11.6 ± 0.6 | 12.3 ± 0.8 |
| 16:1 | 15.16 | 14.1 ± 0.1 | 14.2 ± 0.4 | 14.4 ± 0.3 |
| 17:1 | 0.00 | 1.1 ± 0.0 | 1.9 ± 0.3 | 2.1 ± 0.5 |
| 18:0 | 4.75 | 4.8 ± 0.1 | 5.0 ± 0.3 | 5.3 ± 0.4 |
| 18:1 (n-9) | 56.59 | 54.9 ± 0.3 | 54.2 ± 1.4 | 52.0 ± 2.4 |
| 18:2 (n-6) | 0.00 | 12.0 ± 0.4 | 10.8 ± 0.7 | 11.3 ± 0.5 |
| Other FA | 12.40 | 1.4 ± 0.1 | 1.5 ± 0.2 | 1.6 ± 0.3 |
| OCFA (% DW) | 0 | 0.3 ± 0.03 | 0.5 ± 0.02 | 0.5 ± 0.09 |
| OCFA (% TFA) | 0 | 1.4 ± 0.04 | 2.3 ± 0.30 | 2.6 ± 0.83 |

TABLE 13

Lipid and fatty acid analyses of *Yarrowia lipolytica* ATCC18944 fed increasing daily propionate concentrations

|  | Time (h) | | | |
|---|---|---|---|---|
|  |  | 0 h | 168 h | 168 h | 168 h |
|  |  | | Daily Propionate (g/L) | | |
|  | Initial | 0 | 0 + 0 + 1 + 1 + 1 + 1 | 0 + 0 + 2 + 2 + 2 + 2 |
| Total Lipids (% DW) | 10.00 | 22.7 ± 1.2 | 19.0 ± 0.0 | 18.3 ± 0.6 |
| Total Fatty Acids (% DW) | 7.9 | 22.0 ± 1.8 | 17.3 ± 1.6 | 16.2 ± 0.5 |
| Fatty Acid Profile (% TFA) | | | | |
| 15:0 | 0.0 | 0.3 ± 0.0 | 1.3 ± 0.0 | 1.4 ± 0.1 |
| 16:0 | 14.0 | 12.4 ± 0.5 | 13.2 ± 1.0 | 13.8 ± 1.6 |
| 16:1 | 15.7 | 13.8 ± 0.4 | 12.2 ± 0.1 | 12.0 ± 1.1 |
| 17:1 | 0.0 | 1.1 ± 0.0 | 10.0 ± 0.7 | 10.0 ± 1.2 |
| 18:0 | 6.4 | 5.2 ± 0.3 | 6.3 ± 0.7 | 6.9 ± 1.4 |
| 18:1 (n-9) | 49.5 | 52.0 ± 0.5 | 40.0 ± 0.0 | 38.8 ± 0.4 |
| 18:2 (n-6) | 14.4 | 13.9 ± 0.2 | 14.2 ± 0.7 | 13.1 ± 0.6 |
| Other FA | 0.0 | 61.3 ± 0.8 | 2.7 ± 0.5 | 54.0 ± 3.0 |
| OCFA (% FA) | 0 | 1.4 ± 0.1 | 13.1 ± 0.6 | 13.3 ± 1.3 |
| OCFA (% DW) | 0.0 | 0.3 ± 0.0 | 2.3 ± 0.3 | 2.2 ± 0.2 |

Figure 26:
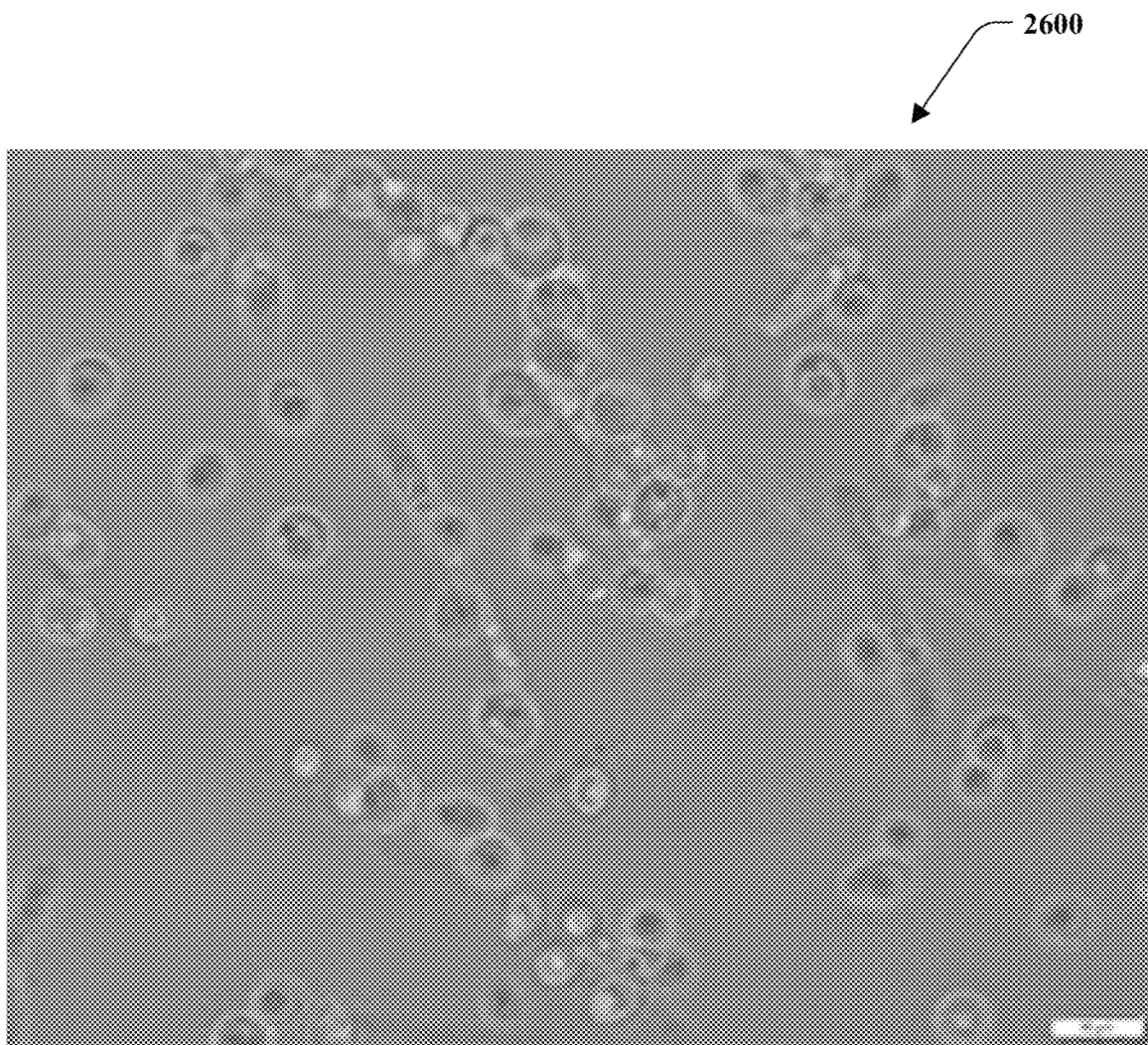
FIG. 26 is a micrograph illustrating the filamentous and yeast morphology of *Yarrowia lipolytica* while producing OCFAs.

As an example, unlike *A. acetophilum* HS399, *Yarrowia lipolytica* can accumulate OCFA without accumulating Docosahexaenoic acid (DHA), which might be beneficial for certain formulations when long chain polyunsaturated fatty acids (e.g., like DHA) are not desired. As illustrated in FIG. 26, in one implementation, *Y. lipolytica* can produce OCFAs in polymorphic cultures 2600, which are combinations of filamentous molds and yeast morphology. As an example, these results suggest that, in addition to production in algae (e.g., *Aurantiochytrium*), OCFAs may also be produced by fungi, regardless of their yeast or filamentous morphology.

Figure 27:
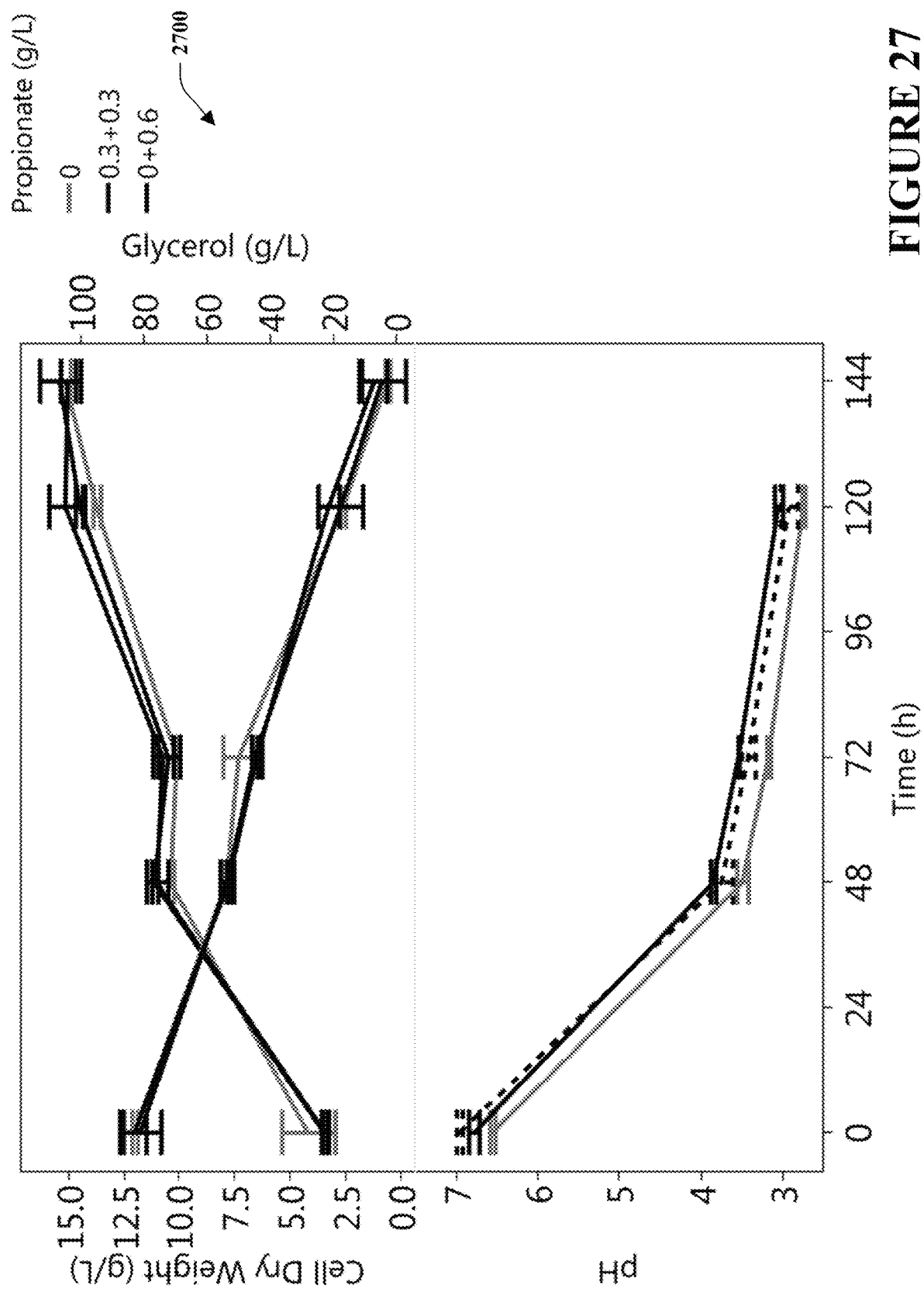
FIGS. 27 and 28 are graphical representations of cell dry weight, residual glycerol, and pH where *Y. lipolytica* is cultivated with increasing daily propionate concentrations.
Figure 28:
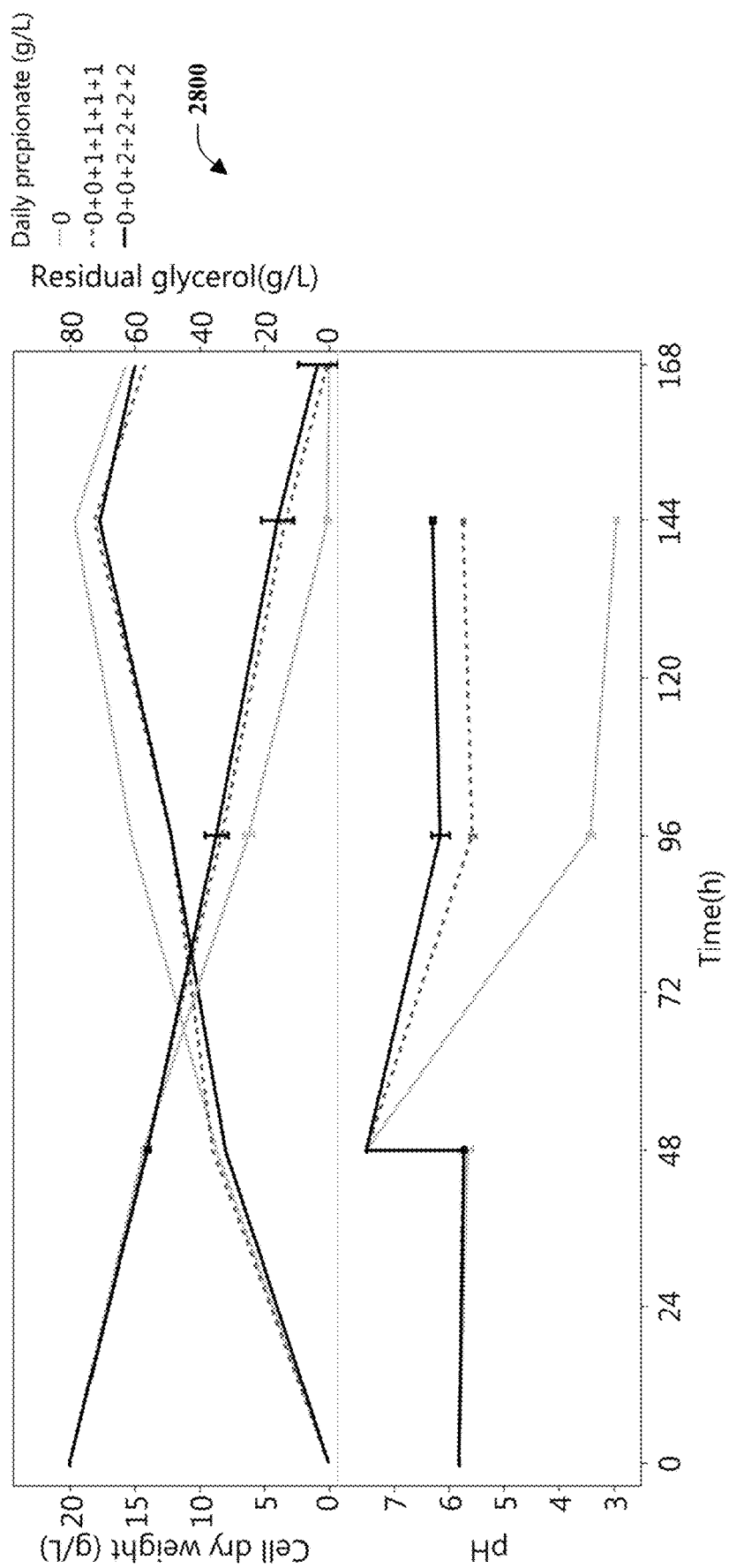

FIGS. 27 and 28 are graphical representations of implementations where *Y. lipolytica* is cultivated with increasing daily propionate concentrations 2700, 2800. In these implementations, the results illustrate that growth of the *Y. lipolytica* may not be affected by up to 2 g/L d propionic fed despite the low pH (3) present. As illustrated, under these conditions the accumulation of cytoplasmic propionate equates to 328 g/L, which indicates how this strain can have a high tolerance to propionic acid toxicity.

Figure 29:
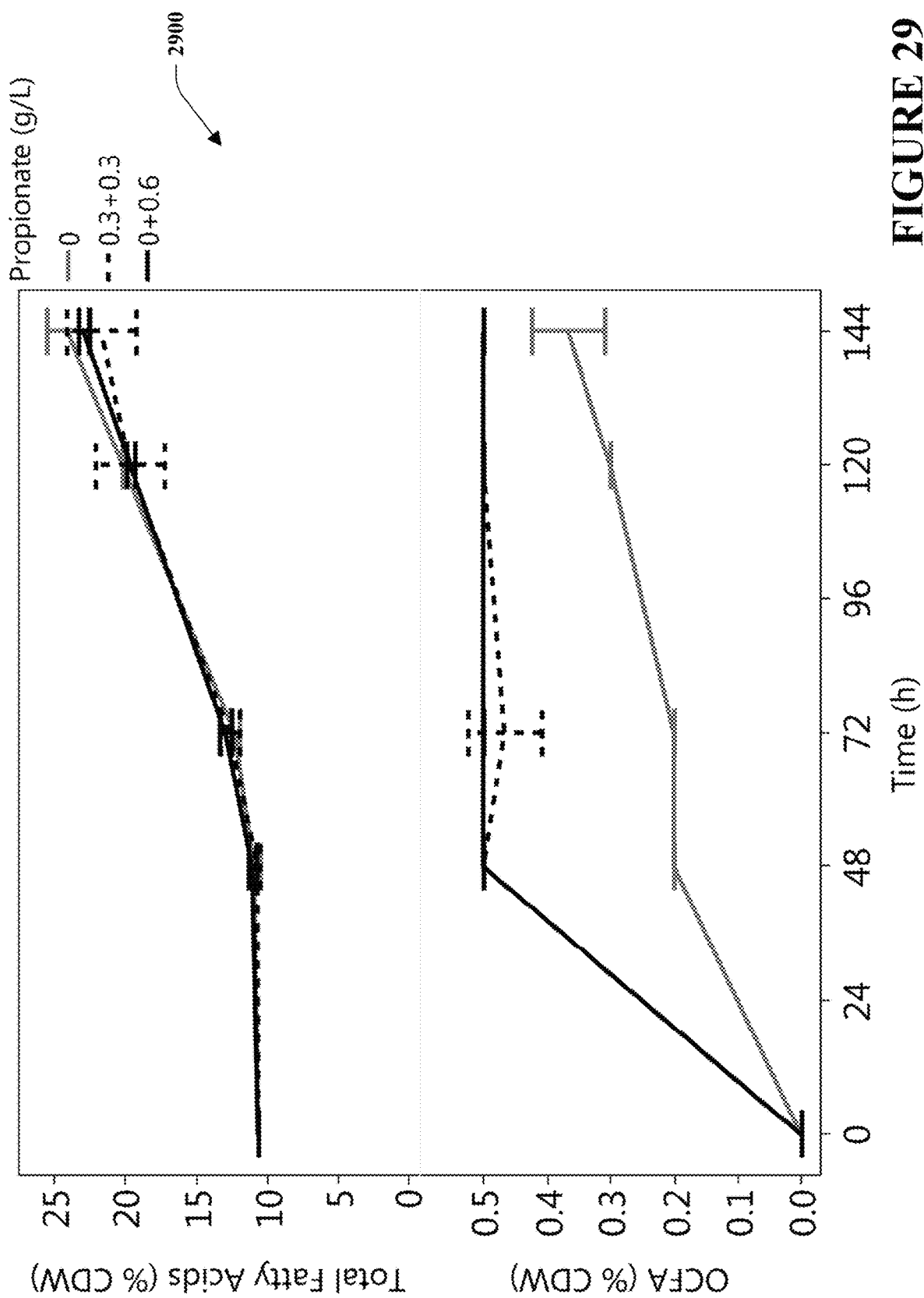
FIGS. 29 and 30, are graphical representations of odd chain fatty acid % dry weight and total fatty acid % dry weight where *Y. lipolytica* is cultivated with increasing daily propionate concentrations.
Figure 30:
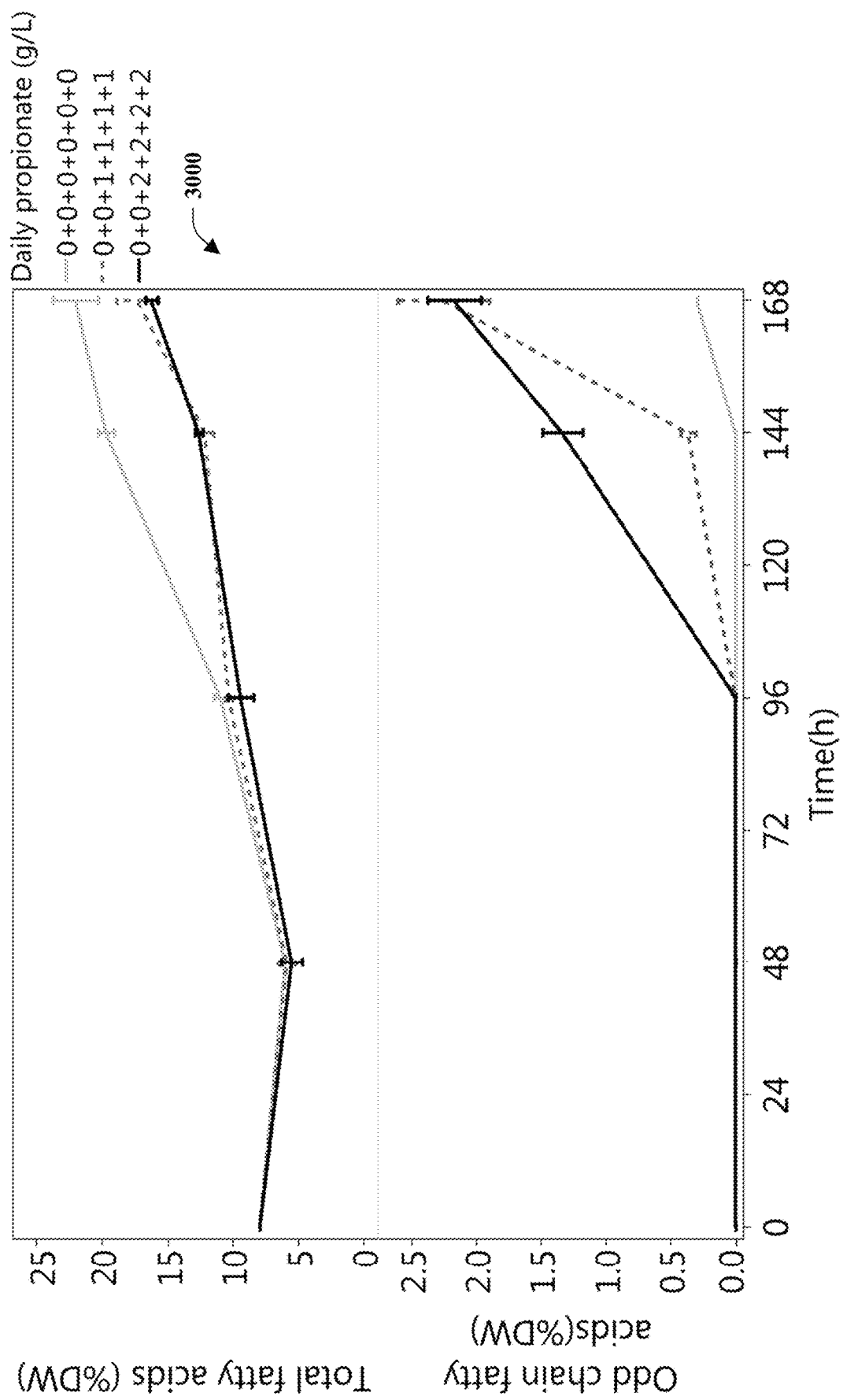

Further, FIGS. 29 and 30, are graphical representations of implementations where *Y. lipolytica* is cultivated with increasing daily propionate concentrations 2900, 3000. In these examples, the results illustrate that the *Y. lipolytica* cells can accumulate lipids above 20% DW, with OCFA concentrations above 10% of TFA. As an example, the relatively low OCFAs levels produced by *Y. lipolytica* may be associated with the catabolic loss of propionate through the methylcitrate pathway. In one implementation, to address this issue, and to increase the propionic acid incorporation in OCFAs, certain supplements may be added to the media during propagation to mitigate the flow of the propionate though the methylcitrate pathway, which can help mitigate propionic acid oxidative loss. As an example, itaconic acid can be used as a potential inhibitor of the methyl isocitrate enzyme. Table 14, below indicates that itaconic acid may not always provide for mitigation of the propionic acid depositions. One or more alternative inhibitor, such as 3-Nitropropionate, 3-bromo pyruvate and V-13-009920, may provide improved mitigation of the loss of propionate to the methylcitrate pathway.

TABLE 14

Propionic acid deposition in the presence of itaconic acid

|  | | Itaconic acid (g/L)/Propionate (g/L) | |
|---|---|---|---|
| Time (h) 192 | | 0/6 | 0.5/6 |
| Cell dry weight (g/L) | | 8.3 ± 1.2 | 7.9 ± 1.1 |
| Consumed propionate (g/L) | | 5.1 ± 1.5 | 5.0 ± 1.6 |
| Propionate (MW)/OCFA (MW) | | 0.3 | 0.3 |
| Odd chain fatty acids (% DW) | | 1.3 ± 0.5 | 1.1 ± 0.6 |
| Propionic acid deposition (%) | | 0.6 ± 0.1 | 0.5 ± 0.2 |

In summary, in this implementation, *Yarrowia lipolytica* could be used to produce oils rich in OCFAs. The OCFA concentration in the resulting oil, and the productivity, may be below that obtained with the microalgae *A. acetophilum* HS399. However, *Y. lipolytica* provides advantages because the main OCFA is C17:1 n-8, and *Y. lipolytica* does not produce highly unsaturated fatty acids like may be found with *A. acetophilum* HS399, which might be preferred in certain applications.

Example 8—Propionate Induced Growth Inhibition

In another aspect, techniques may be devised to determine intracellular propionate accumulation in microbials. In this aspect, a potentially lethal concentration of propionate may be identified for desired cultures of OCFA producing biologicals that are utilizing propionate to increase OCFA production. In this way, for example, a high threshold amount of propionate may be identified for desired biologicals that produce desired OCFA accumulation while maintaining a desired growth rate for the target biologicals.

In one implementation, the model used to determine intracellular propionate accumulation, using Henderson and Hasselbach equations, can be calibrated by establishing the lethal concentration threshold of intracellular propionate that *A. acetophilum* (HS399) could tolerate. The calibration can be further verified using two different approaches, propionate concentration and pH-driven propionic acid toxicity.

In a first implementation, an Erlenmeyer flask can be inoculated with 0, 10, 20, and 30 g/L initial treatments of propionate, at a substantially constant pH of 6.4. In this implementation, observation indicates that the treatments containing 20 and 30 g/L will not survive. This model can be used to translate the extracellular pH and propionic acid concentration to intracellular propionate concentrations, a metric that could be interpreted across different pH values and propionate concentrations scenarios. Table 15 below illustrates that initial propionate treatment of propionate at 20 g/L results in lethality of the culture. Further, the cytosolic (the cytoplasmic matrix is the liquid found inside cells) propionate concentration is identified to be 97.7 g/L using the model.

TABLE 15

Propionic acid toxicity lethal threshold measured according to two different approaches

| Toxicity Applied | pH Drift | Initial Propionate |
|---|---|---|
| Toxicity Type | Acute | Chronic |
| Metric Used | OUR | CDW |
| pH | 5.3 | 6.4 |

TABLE 15-continued

Propionic acid toxicity lethal threshold measured according to two different approaches

| Toxicity Applied | pH Drift | Initial Propionate |
|---|---|---|
| Propionate Treatment (g/L) | 2.3 ± 0.1 | 20 |
| Cytosolic Propionate (g/L) | 107.5 ± 3.5 | 97.7 |

Figure 31:
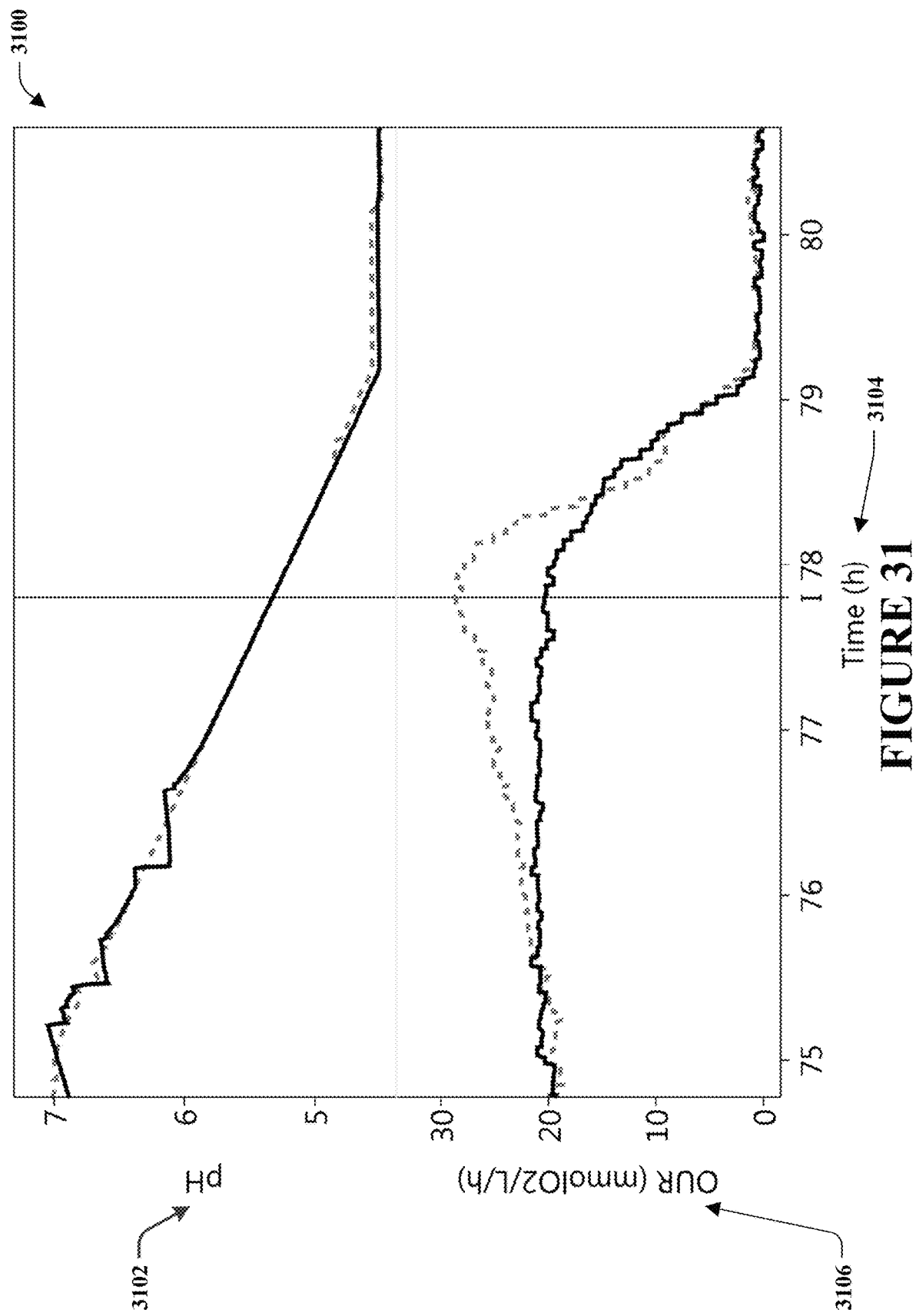
FIG. 31 is a graphical representation of the *A. acetophilum* HS399 oxygen uptake (OUR) in response to pH driven propionate toxicity.

In a second implementation, the evolution of the oxygen uptake rate (OUR) is measured for two cultures where the decreasing pH set point is controlled with propionic acid. FIG. 31 is a graphical representation of an example 3100 where, in this implementation, the pH 3102 can be steadily decreased from 7 down to 4 at a rate of 0.7 pH units per hour 3104. In this example 3100, during the four hours of pH ramp, residual propionate concentration in the media is maintained relatively constant (e.g., 2.3-2.4 g/L). In this implementation, the OUR remains relatively constant until the pH reached 5.3, and the OUR 3106 measurement dropped in response to propionate toxicity. In FIG. 31, the example 3100 shows monitoring of *A. acetophilum* HS399 oxygen uptake rate (OUR) in response to pH driven propionate toxicity. In this example, the results illustrate that cell respiration was not substantially affected until the pH reached 5.3 (vertical line I), which suggest this may be the tolerance limit for propionate by *A. acetophilum* HS399.

As illustrated in Table 15, above, the model illustrated in the example 3100 of FIG. 31 can be used to translate the extracellular pH and propionic acid concentration to intracellular propionate concentrations. For example, this can be confirmed as a substantial equivalent to the concentration obtained with the "initial propionate" approach (107.5 vs 97.7 g/L). The results demonstrate that intracellular propionate concentration may be a valid metric for propionic acid toxicity and used as a metric that can be interpreted across different pH values and propionate concentrations scenarios (see Table 15).

Figure 32:
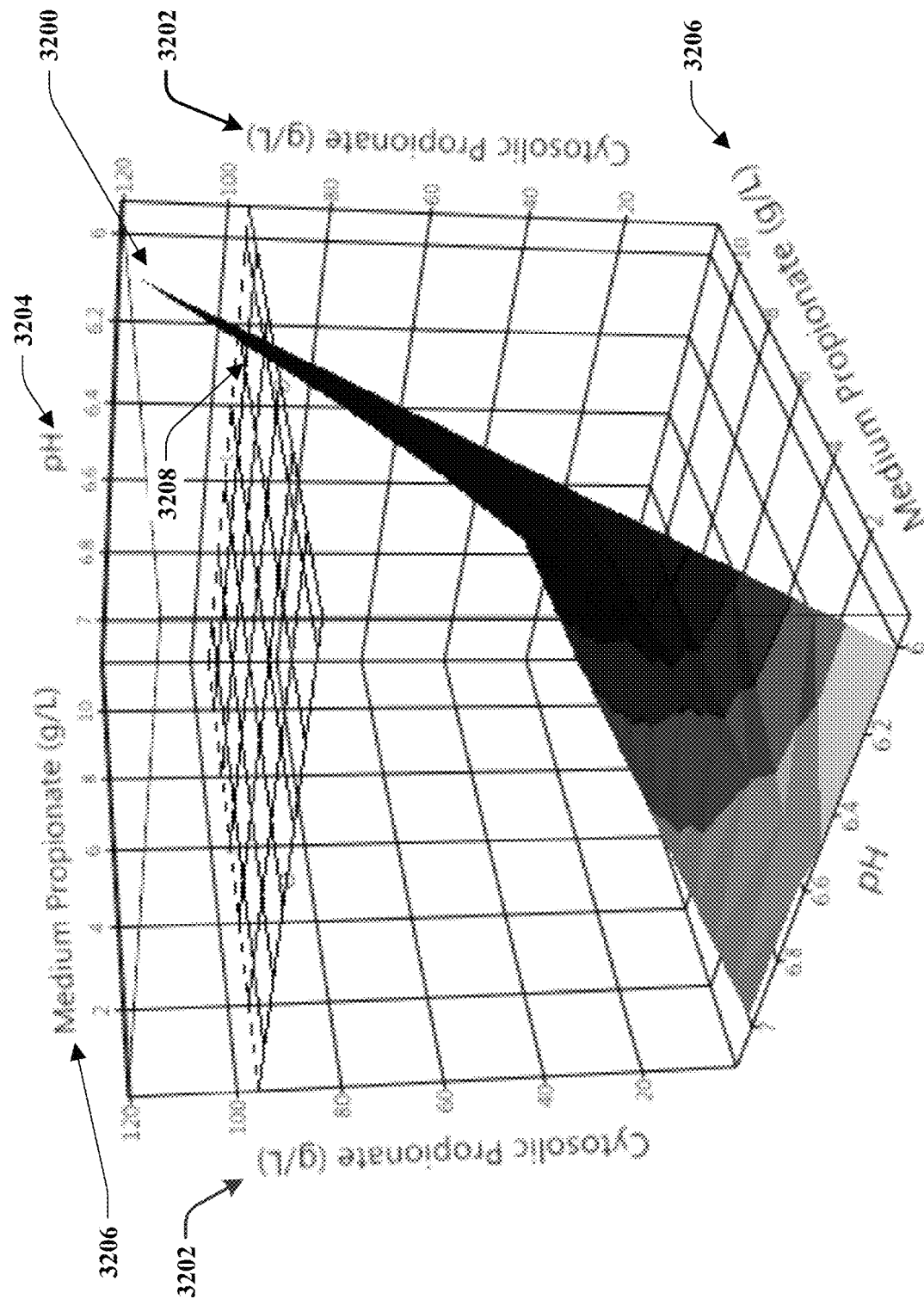
FIG. 32 is a 3D graphical representation of the propionic acid toxicity as cytosolic propionate is controlled by the extracellular pH and propionate concentration.

FIG. 32 is a 3D graphical representation of an example expression of the propionic acid toxicity 3200. In this example, the propionic acid toxicity 3200 is expressed against a grid that defines the threshold toxicity 3208 limit for different pH 3204 and extracellular propionate combinations 3206. As an example, the graphing of the propionate toxicity model can be a very useful tool for the design of the odd chain fatty acid production process. In this example, the propionic acid toxicity 3200 represented as cytosolic propionate 3202 is controlled by the extracellular pH 3204 and propionate concentration 3206. In one implementation, the 3D graph can be built through the integration of Henderson and Hasselbalch equation. The grid intersection line 3208 represents the lethal toxicity threshold validated experimentally according to two different approaches.

In one implementation, a lower level of propionic toxicity may be determined, as described in the following example techniques:

Identify Lower Propionic Toxicity: Batch Vs. Fed-Batch

Figure 33:
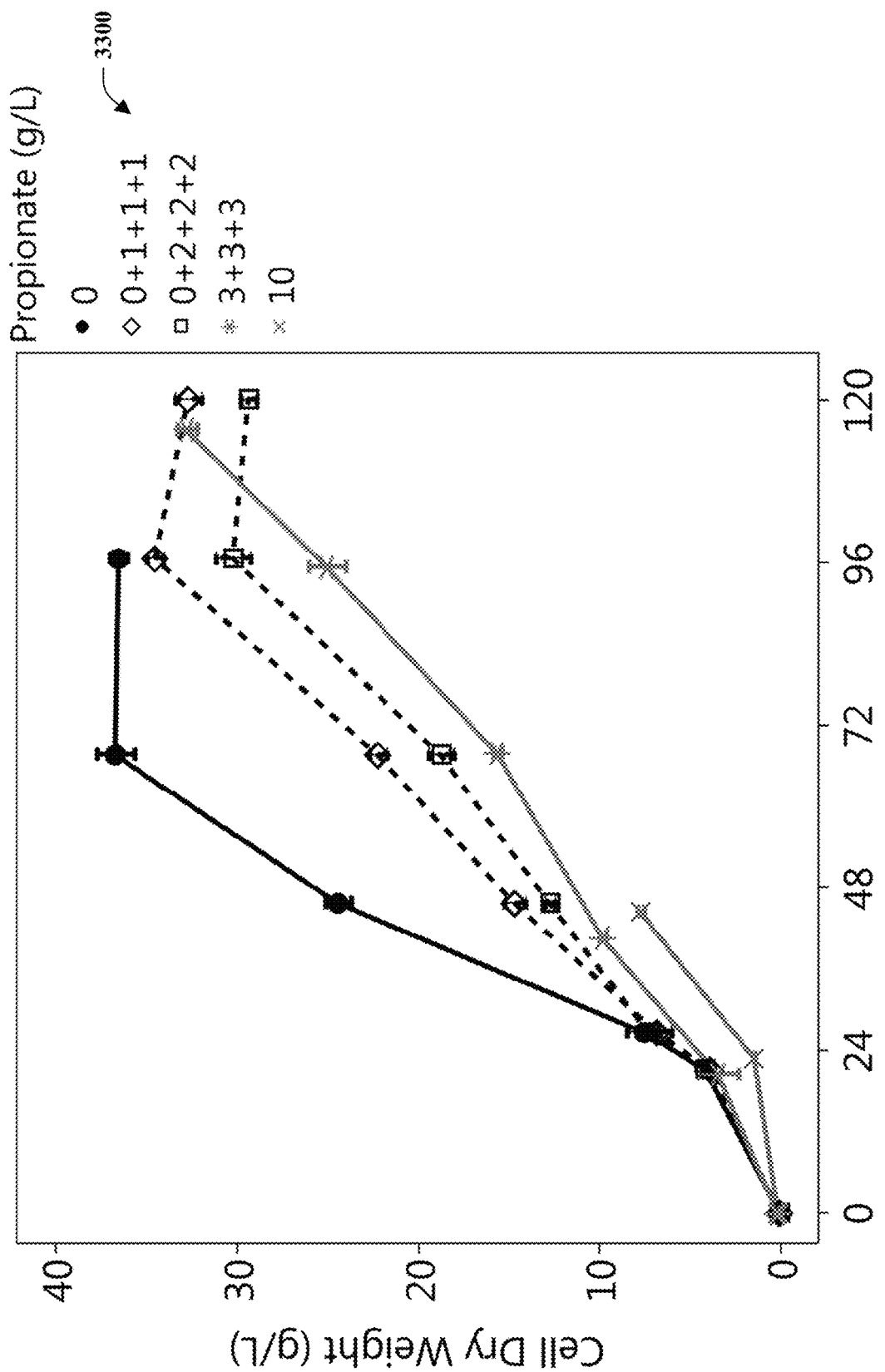
FIG. 33 is a graphical representation of *A. acetophilum* HS399 in the presence of batched or fed batch propionate at different daily concentrations.

In one implementation, a 250 mL Erlenmeyer flask can be used to cultivate *A. acetophilum* HS399. In this example, sodium propionate can either be batched or fed batch different propionate concentrations each day. FIG. 33 is a graphical representation illustrating an example 3300 where cell dry weight is measured each day to evaluate the impact of the propionate feeding strategy in *A. acetophilum* HS399 growth. This example illustrates treatment of 3+3+3 (e.g., over respective days), where 3 g/L propionate is fed at 0, 24 and 48 hrs (9 g/L in total). This treatment appears to provide better growth than a treatment fed 10 g/L propionate at 0 hr. These results illustrate that fed-batching may be a better strategy to lower propionic acid toxicity than batching all the propionate at initial inoculation. Further, as illustrated in this example 3300, growth is decreased in a dose response manner with the daily amount of propionate fed. In this example, the best growth is achieved with the lowest propionate dose (1 g/L d), but this treatment still shows growth inhibition when compared against the non-propionate control treatment (0 g/L d).

Identify Lower Propionic Toxicity: Growth Vs. Lipid Phase

In one implementation, a 250 mL Erlenmeyer flask can be used to cultivate *A. acetophilum* HS399. In this example, 3 g/L of propionic acid can be fed during growth phase (3+0) or during lipid phase (0+3). Growth phase treatment is fed propionate at inoculation (0 hr), while lipid phase treatment can be fed propionate upon depletion of the ammonia from the media (~24 hrs). Cell dry weights may be analyzed using a filtration method. Ammonia can be measured using a Cedex bio-analyzer (Roche). Further, propionic acid can be measured using high performance liquid chromatography. The fatty acid profile of the biomass can be analyzed using gas chromatography.

In this implementation, total propionate consumed by the cell can be calculated based on the residual propionate on day 0 and subtracting the final residual propionate. The total propionate deposited in the biomass can be calculated based on the final cell dry weight, multiplied by the total fatty acid (TFA) ratio in biomass, multiplied by the OCFA ratio in TFA, and multiplied by the molar factor of propionate in odd chain fatty acid, which averages at about 0.3. The propionate deposition can be calculated by dividing the propionate deposited by the propionate consumed and expressed as percent.

Figure 34:
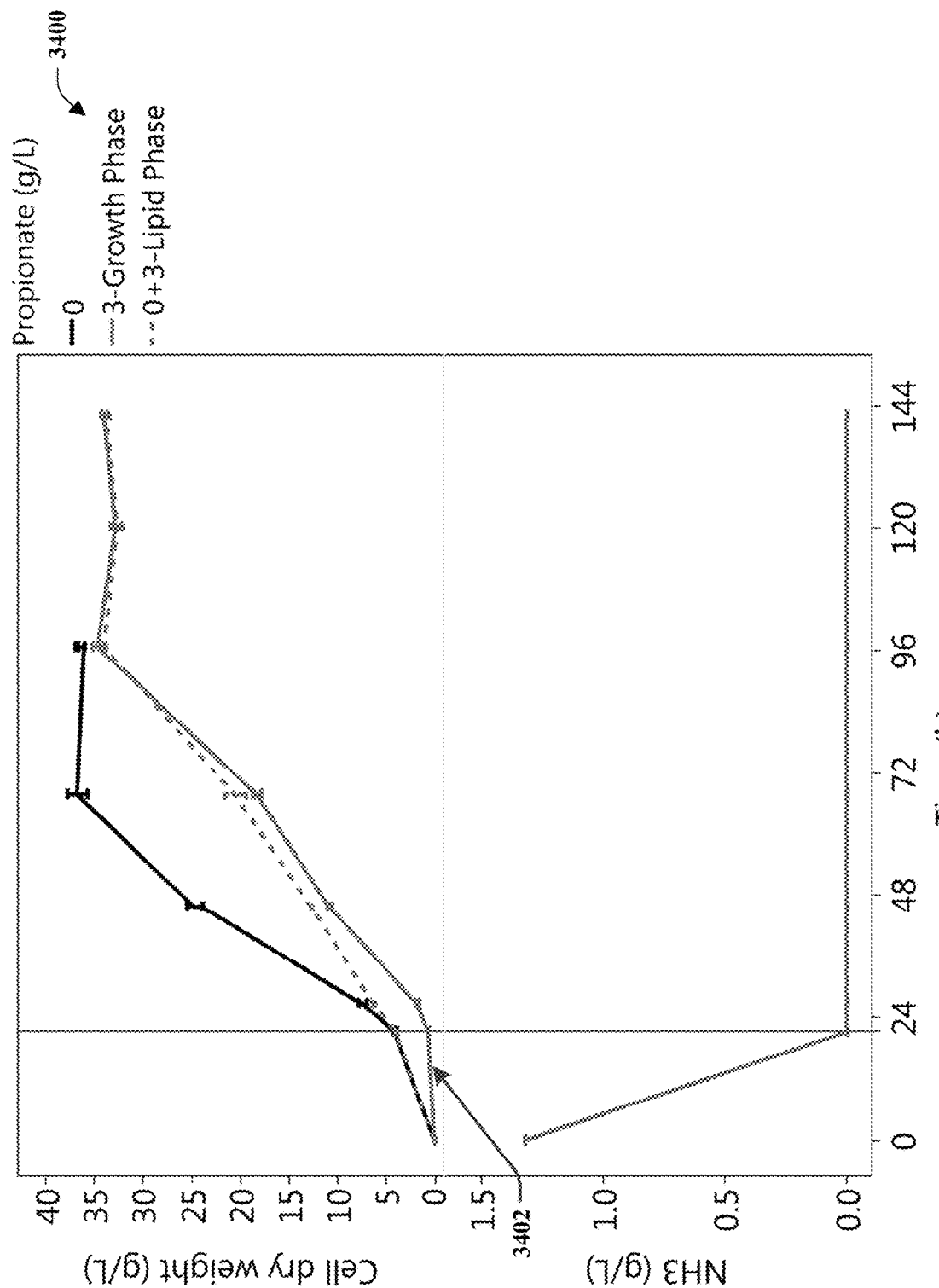
FIG. 34 is a graphical representation illustrating results of growth of *Aurantiochytrium acetophilum* HS399 and residual ammonia when propionate was fed in growth or lipid phase.

FIG. 34 is a graphical representation illustrating results 3400 of growth of *A. acetophilum* HS399 and residual ammonia when propionate was fed in growth or lipid phases. As illustrated, the results 3400 identify that propionic acid (0+3) is fed during the lipid phase, once the ammonia was depleted from the media. As illustrated, this treatment during the lipid phase did not appear to provide a lag phase 3402 that was present when propionate was fed during the growth phase. Additionally, the propionic acid deposition is slightly improved when propionate is fed during the lipid phase than when propionate was fed in the growth phase. These results 3400 illustrate that feeding propionate during lipid phase may be preferred over feeding during the growth phase because of the lack of lag 3402 during the lipid phase, and an increases of lipid deposition from 53 to 58.8%, as illustrated in Table 16 below.

TABLE 16

Propionic acid deposition into *Aurantiochytrium acetophilum* HS399 according to the stage in which propionate was fed

| Propionate (g/L) | Propionate Deposition (%) |
|---|---|
| 0 (control) | 0.0 ± 0.0 |
| 3 (growth) | 53.0 ± 1.0 |
| 0 + 3 (lipid) | 58.8 ± 1.9 |

Example 9—Pathway Elucidation: *A. acetophilum* HS399 May not Use Propionic Acid as Sole Carbon Source In one aspect, propionic acid may be either incorporated into *A. acetophilum* HS399 lipids or catabolized into the citric acid cycle. In this aspect, the propionate deposition may be controlled by both the rate of lipid synthesis and the rate of propionate catabolism. For example, there are two main catabolic pathways that are responsible for propionate oxidation into the citric acid cycle. The methyl-malonate pathway converts propionate into succinyl-CoA which enters the citric acid cycle. Alternatively, the methyl-citrate pathway, converts propionate into succinate and pyruvate, both of which enter the citric acid cycle.

As identified by one or more the techniques described herein, the methyl-citrate pathway is anaplerotic because it releases two intermediates of the citric acid cycle. Because propionate is not an anaplerotic substrate, growth on propionate (e.g., as a sole carbon source) may be sustained by an anaplerotic pathway such as the methyl-citrate. Non anaplerotic pathways, such as methyl-malonate pathway, which releases only one citric acid intermediate (succinyl-CoA intermediate), may not sustain growth on propionate as sole carbon source.

Figure 35:
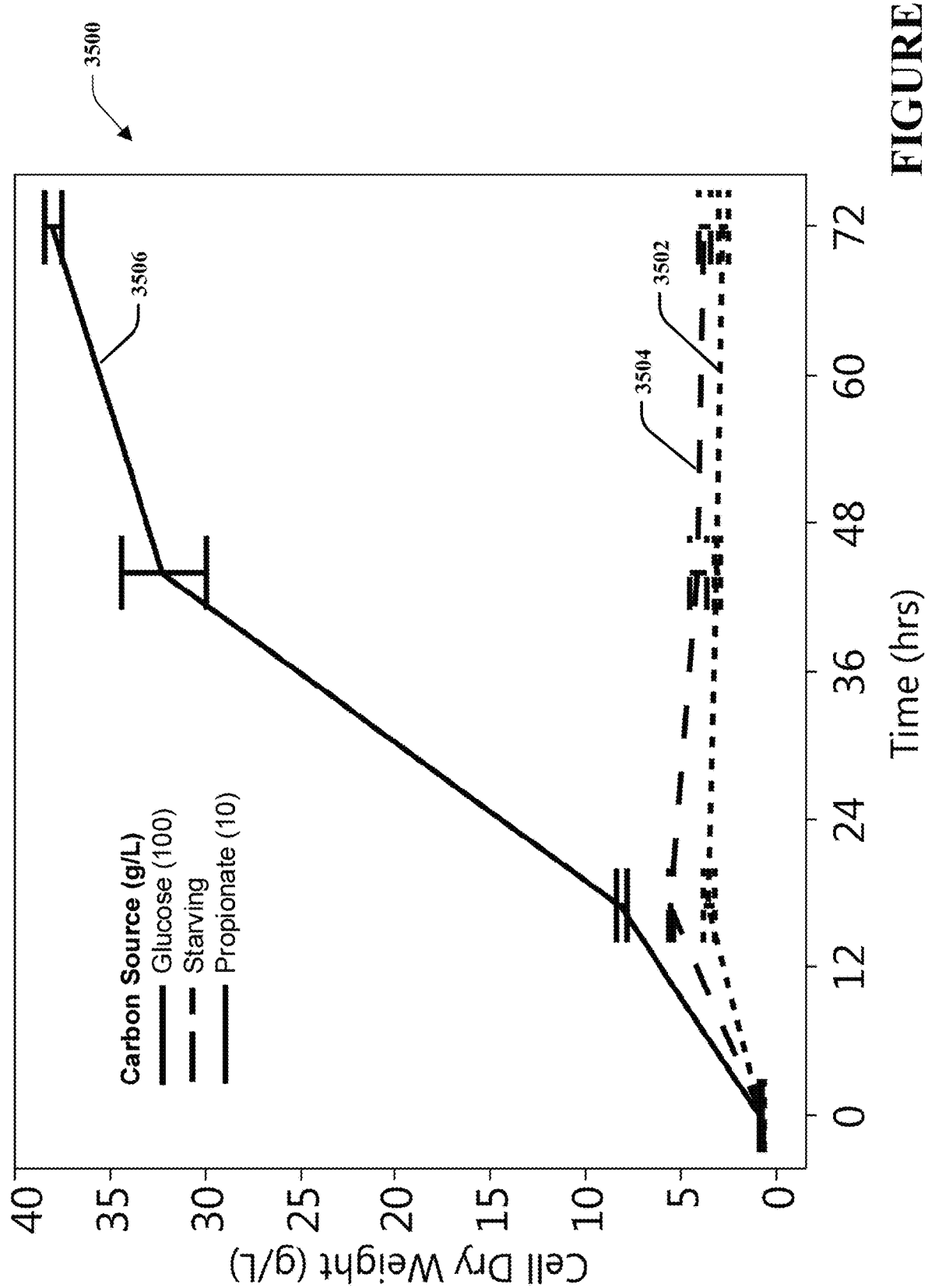
FIG. 35 is a graphical representation illustrating the growth of *A. acetophilum* HS399 with different carbon sources.

In one implementation, the capacity of *A. acetophilum* HS399 to grow on propionate as sole carbon can be determined to help identify the catabolic pathway for propionate catabolism. In this implementation, an Erlenmeyer flask (250 ml) can be inoculated (1% v/v) in triplicates at a pH of 7. One treatment can be fed with non-lethal concentrations of propionate (e.g., 10 g/L), and other treatments can be fed glucose as a positive control, or no carbon substrate as a negative control. FIG. 35 is a graphical representation of one implementation that illustrates results 3500 of growth of *A. acetophilum* HS399 with different carbon sources. As illustrated, the results 3500 illustrate that the propionic acid treatment 3502 did not support growth above that of the starved treatment (negative control) 3504; while the glucose treatment 3506, as expected, supported high growth.

Figure 36:
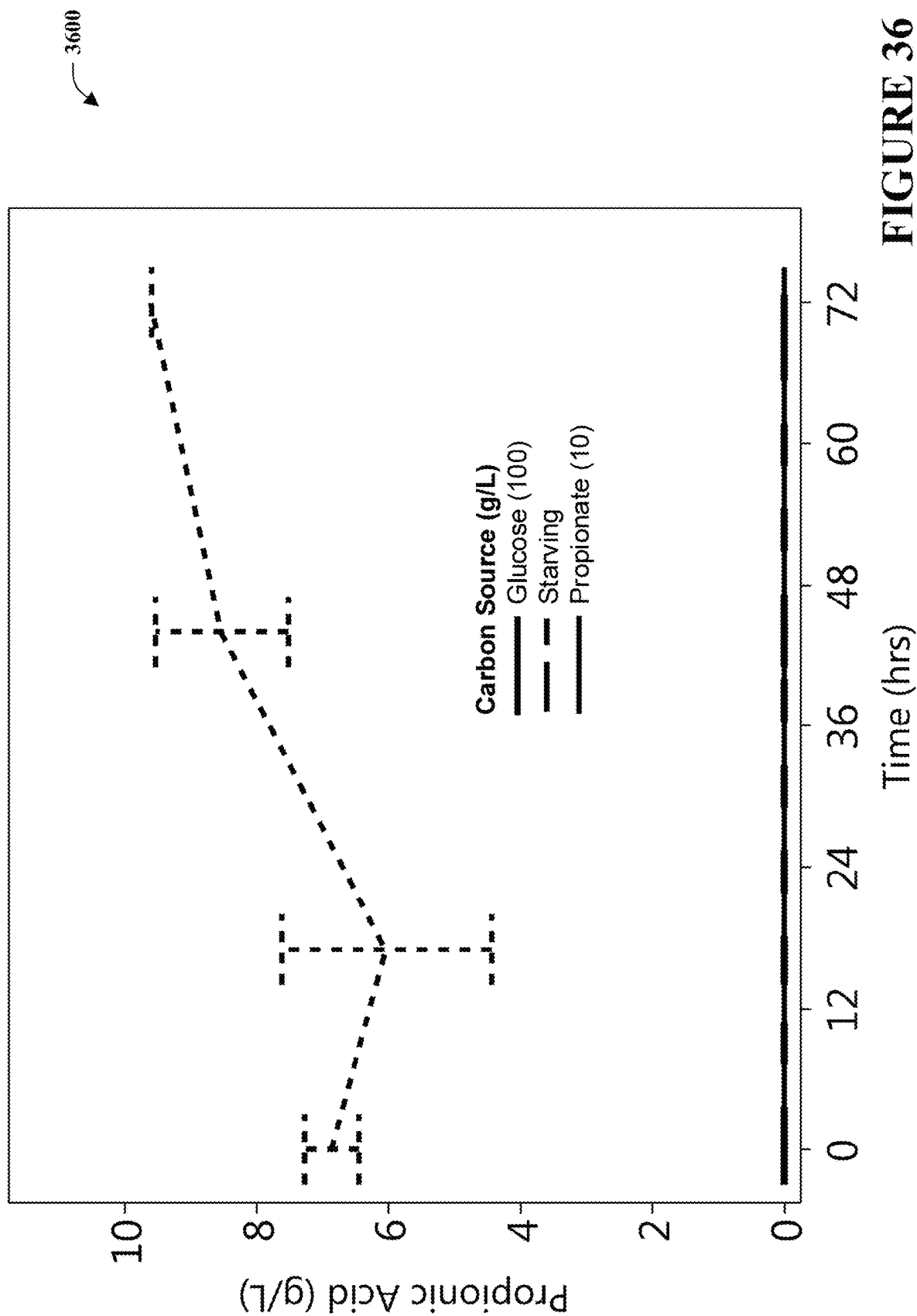
FIG. 36 is a graphical representation illustrating the residual propionate cultures of *A. acetophilum* HS399 fed different carbon sources.

Further, as illustrated in FIG. 36, shows example results 3600 of residual propionate cultures of *A. acetophilum* HS399 fed different carbon sources. The results 3600 illustrate that the residual propionate does not decrease in response to cell uptake. These results 3500, 3600, suggest that the methyl-citrate cycle may not be active in *A. acetophilum* HS399. Therefore, propionic acid is most likely catabolized via a non anaplerotic methylmalonate pathway.

Example 10—Metabolic Intervention: Cyanocobalamin Regulating Propionate Catabolism in Microbials As described above, methyl-malonate is likely the main propionate catabolic pathway in *A. acetophilum* HS399. The enzyme methylmalonyl-CoA mutase converts a methylmalonyl-CoA into succinyl-CoA, in a reaction that utilizes cyanocobalamin (vitamin B12) as a cofactor.

Figure 37:
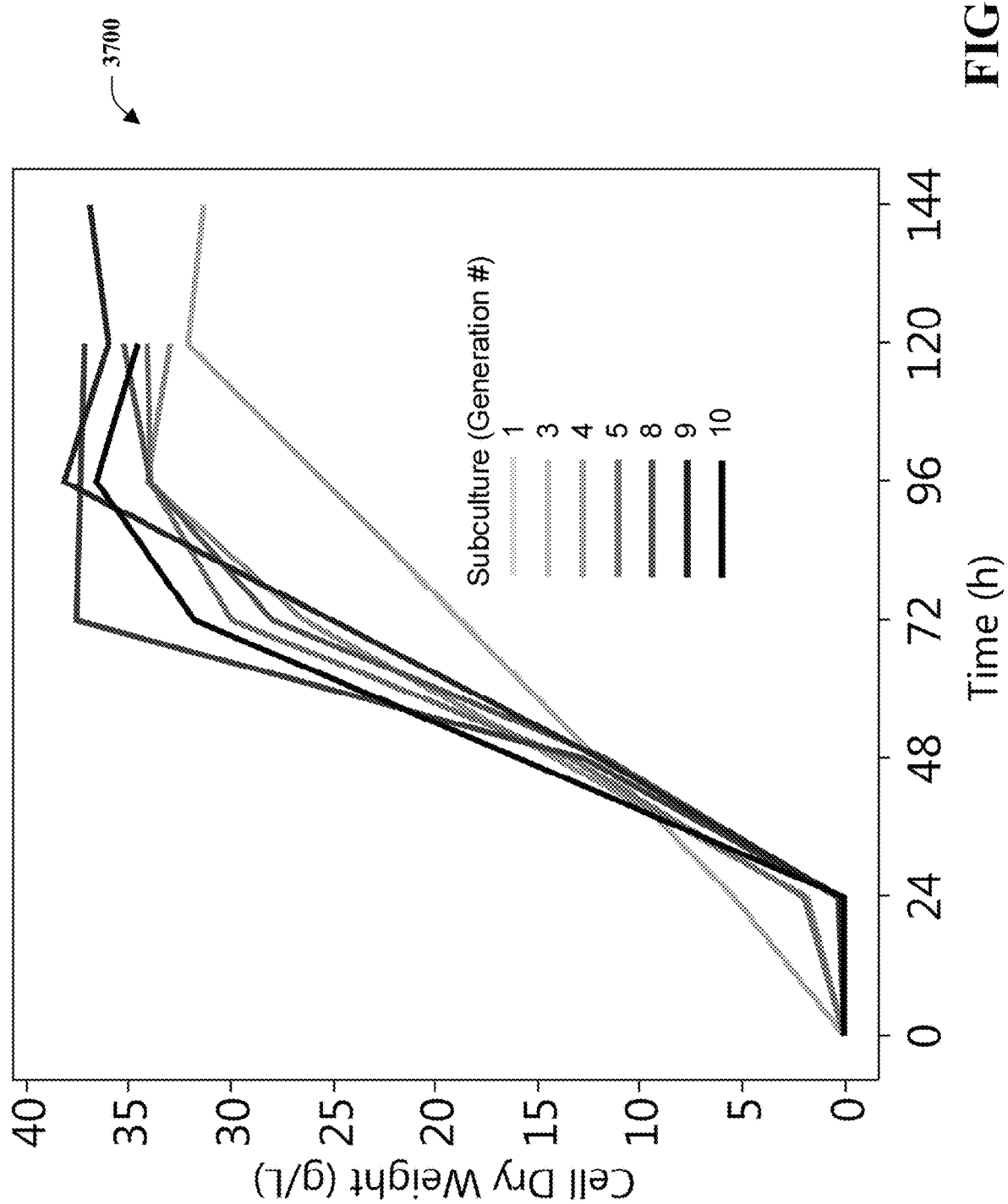
FIG. 37 is a graphical representation of example results of sub-culturing *A. acetophilum* HS399 in a cyanocobalamin deprived media for over 10-generations.

In one implementation, *A. acetophilum* HS399 can be sub-cultured in a cyanocobalamin deprived media for at least 10-generations. FIG. 37 is a graphical representation of example results 3700 of sub-culturing *A. acetophilum* HS399 in a cyanocobalamin deprived media for over 10-generations. The results 3700 illustrate that there is substantially no impact on growth of *A. acetophilum* HS399 between generations. In this example, the numerous generations help dilute the possibility of potential cell reserves of cyanocobalamin and demonstrate that cyanocobalamin (Vitamin B12) is not likely essential. These results 3700 also provide adequate evidence that *A. acetophilum* HS399 is not a cyanocobalamin auxotroph.

In one implementation, the impact of methionine supplementation in the growth of A, acetophilum HS399 can be illustrated. In this implementation, methionine synthetase can use cyanocobalamin as a cofactor to generate methionine from homocysteine. In this implementation, a growth media can be supplemented with 0 and 0.5 g/L methionine and the growth can be measured under the presence and absence of cyanocobalamin (0.00037 µM). The methionine supplementation does not appear to have an impact in growth of *A. acetophilum* HS399 (FIG. 38), regardless of the presence or absence of cyanocobalamin. As an example, this may be consistent with *A. acetophilum* not being a cyanocobalamin auxotroph.

In one implementation, a cyanocobalamin deprived *A. acetophilum* HS399 can be inoculated in triplicates (n=3) in the presence of propionate (3 g/L), using three different concentrations of cyanocobalamin (0.37, 0.00037, 0 µM). The propionic acid deposition by *A. acetophilum* HS399 can be analyzed according to the method described above regarding Propionic Acid Deposition Rate. As illustrated in Table 17 below, a dose response increase in propionate deposition is identified, with decreasing concentration of cyanocobalamin in the media. Of note, a cyanocobalamin deprived media (0 µM) can result into 99.5% of the propionate being incorporated into *A. acetophilum* HS399 lipids as OCFAs. For example, this may suggest that almost no propionate is oxidized, presumably due to the lack of methyl-malonyl-CoA mutase cofactor (e.g., cyanocobalamin) blocking the pathway. The results shown in Table 17 are consistent with the methyl citrate pathway not being active (as described above), and methyl-malonate may be the primary catabolic pathway for propionic acid oxidation. A benefit associated with increasing propionate deposition is decreasing the propionate used for the production of OCFAs.

TABLE 17

Propionic acid deposition in response to cyanocobalamin (vitamin B12) concentration

| | Cyanocobalamin-Vit $B_{12}$ (µM) | | |
|---|---|---|---|
| | 0.37 | 0.00037 | 0 |
| Cell dry weight (g/L) | 37.0 ± 1.4 | 32.0 ± 0.7 | 35.0 ± 1.2 |
| OCFA (% DW) | 2.7 ± 0.2 | 14.7 ± 0.2 | 25.0 ± 0.3 |
| Initial propionate (g/L) | 3 | 3 | 3 |
| Final Propionate (g/L) | 0.06 | 0.1 | 0.36 |
| OCFA (g/L) | 1.0 ± 0.1 | 4.7 ± 0.1 | 8.7 ± 0.4 |
| Propionate (MW)/ OCFA (MW) | 0.3 | 0.3 | 0.3 |
| Propionate deposition (% fed) | 10.3 ± 1.0 | 47.0 ± 0.9 | 99.9 ± 5.8 |

Example 11—Metabolic Intervention: Cyanocobalamin May not Impact Propionic Acid Toxicity In one implementation, in can be determined whether an increase of propionate deposition, through cyanocobalamin deficiency, has a negative impact in *A. acetophilum* HS399 growth and productivity. For example, a testing can show if propionic acid toxicity is affected by the cyanocobalamin concentration, because, as identified above, cyanocobalamin may not be essential for *A. acetophilum* HS399, at least in the absence of propionate.

Figure 38:
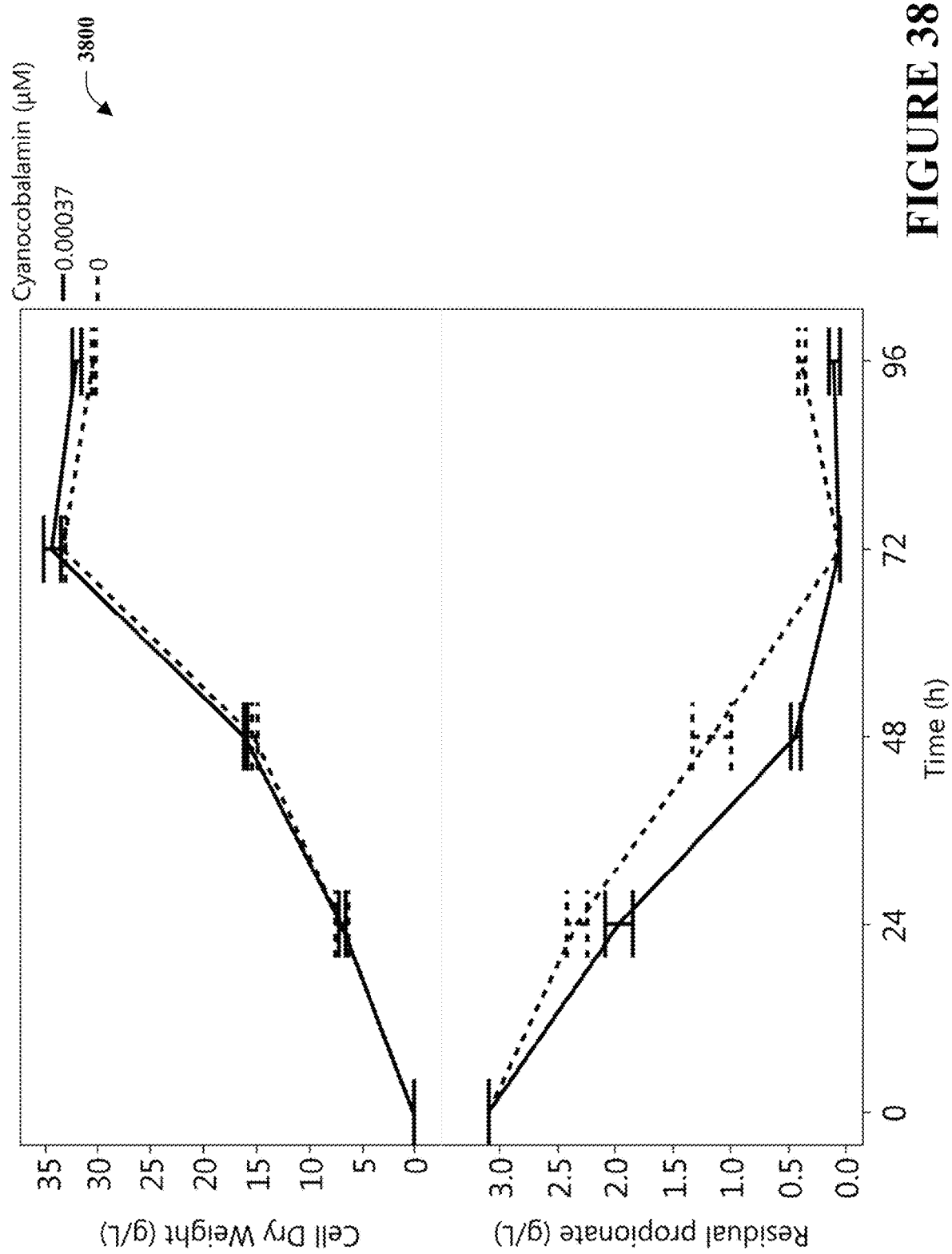
FIG. 38 is a graphical representation of one implementation illustrating example results of cell dry weight and residual propionate where the culture was initially fed 3 g/L propionate.

FIG. 38 is a graphical representation of one implementation illustrating example results 3800 of cell dry weight and residual propionate, 3 g/L propionate. In this implementation, *A. acetophilum* HS399 can be inoculated at different concentrations of cyanocobalamin (0.00037, 0 µM) in triplicates (n=3). In this implementation, the pH can be maintained at 7±1 in respective treatments. The initial 3 g/L propionate fed to the cultures is consumed within 72 hrs, during which insignificant differences are shown in growth due to the cyanocobalamin concentrations, as illustrated by the results 3800. These results suggest that propionic acid catabolism may not be necessarily a protection mechanism for propionic acid toxicity, for example, growth can be inhibited as long as propionic acid is still present, as shown in the lower half of the graph.

Figure 39:
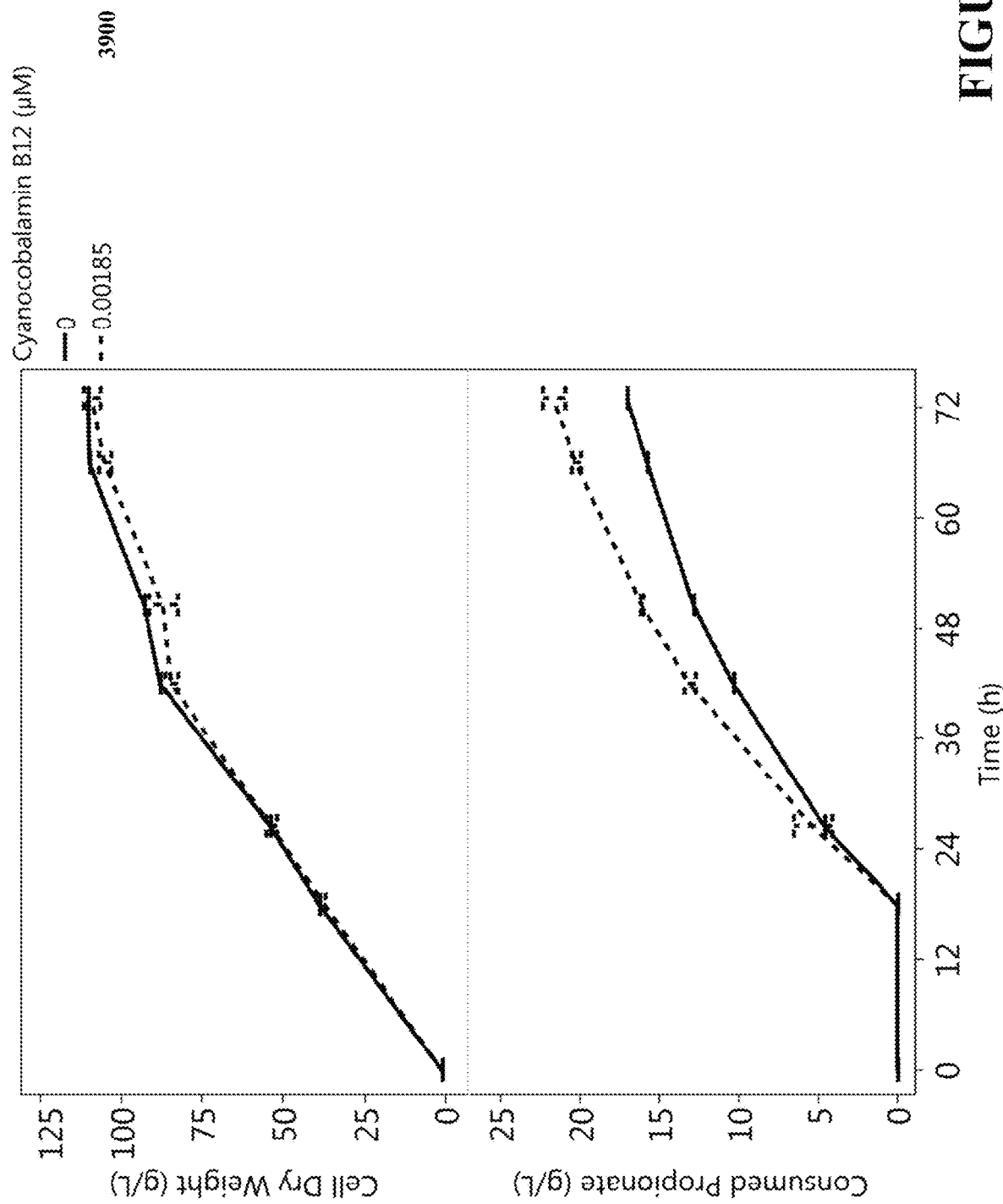
FIG. 39 is a graphical representation of the impact of cyanocobalamin in *A. acetophilum* HS399 growth and propionic acid consumption in 10 L fermenters.

In one implementation, fermenters may be used to culture *A. acetophilum* HS399. In this implementation, propionic acid can be fed-batch in a pH-auxostat mode (e.g., propionic acid used as pH titrant) 24 hrs after inoculation. The fed batch system can appropriately control propionic acid toxicity by maintaining residual propionate concentration at 2.0±0.1 g/L and the pH at 7±0.1. FIG. 39 is a graphical representation showing results 3900 of the impact of cyanocobalamin in *A. acetophilum* HS399 growth and propionic acid consumption in 10 L Bioflo320 fermenters. In this implementation, two treatments using different cyanocobalamin concentrations (0.00185, 0 µM) are compared in duplicates. As illustrated by the results 3900, the growth of both treatments is substantially equivalent, but the treatment without cyanocobalamin consumed 30% less propionic acid. As shown in Table 18 below, the OCFA production may not be substantially affected by the cyanocobalamin concentration, for example, as long as propionic acid is fed on demand. However, as shown in Table 19 below, the propionate deposition is elevated in the treatment without cyanocobalamin. In other words, as an example, cyanocobalamin deficiency may produce the same OCFAs with a much smaller portion of the propionic acid. Further, for example, Cyanocobalamin may not have any impact in propionic acid toxicity and therefore it may be freely manipulated to improve deposition rates.

TABLE 18

Impact of cyanocobalamin in the fatty acid profile of *Aurantiochytrium acetophilum* HS399 cultures grown in a 10 L Bioflo320 fermenters

| | Cyanocobalamin (µM) | | |
|---|---|---|---|
| Time (h) | —<br>0 | 0.37<br>73 | 0<br>73 |
| Total Fatty Acids (% DW) | 26.7 | 54.7 ± 0.5 | 56.9 |
| Fatty Acid Profile (% TFA) | | | |
| 13:0 | 0.0 | 1.4 ± 0.2 | 1.5 |
| 14:0 | 3.8 | 1.4 ± 0.0 | 1.3 |
| 15:0 | 1.1 | 42.6 ± 0.9 | 42.3 |
| 16:0 | 45.2 | 11.7 ± 1.6 | 10.8 |
| 17:0 | 0.4 | 8.6 ± 0.6 | 8.2 |
| 18:0 | 1.6 | 0.3 ± 0.0 | 0.3 |
| 22:5 (n-6) | 7.7 | 3.6 ± 0.1 | 3.8 |
| 22:6 (n-3) | 36.4 | 28.0 ± 1.0 | 29.1 |
| Other FA | 3.8 | 2.5 ± 0.3 | 2.7 |
| DHA (% DW) | 9.7 | 15.3 ± 0.4 | 16.6 |
| OCFA (% TFA) | 1.5 | 52.6 ± 0.5 | 52.0 |

TABLE 19

Propionate deposition.

| Cyanocobalamin (µM) | $g_{propionate}/g_{biomass}$ | Propionate deposition |
|---|---|---|
| 0.37 | 0.18 ± 0.01 | 49.9% |
| 0 | 0.14 | 65.7% |

Example 12—Mitigate Propionic Toxicity: Single Vs. Two-Stage Fermentation

In one implementation, the impact of propionate in two different growth modes can be illustrated, using a two-stage and a single-stage growth mode, utilizing 10 L Bioflo fermenters, for example. In this implementation, a two-stage mode can comprise a first growth stage (0-24 hrs), followed by a lipid phase (24-80 hrs), where nitrogen is not present. Thus, for example, in the two-stage mode substantially all of the nitrogen (5 g/L NH₃) can be fed during growth phase, which is then depleted as it enters a lipid phase. Further, in this implementation, during the lipid phase, no additional nitrogen is fed, and the cell accumulated the lipids. In the single stage mode, half of the nitrogen (2.5 g/L NH₃) can be batch fed, while the other half (2.5 g/L NH₃) can be fed along with the glucose until the end of the fermentation. In this implementation, both treatments receive substantially the same nutrients; however, the single stage mode grows and accumulates lipids in a coordinated way throughout the fermentation. The single stage system can be characterized by an early lipid accumulation.

Embodiments of the single stage system are described in detail in Application No. PCT/US2018/29602 (Ganuza et al.), entitled SINGLE-STAGE FERMENTATION METHODS OF CULTURING MICROORGANISMS, filed on Apr. 26, 2018 by the Applicant herein, which is incorporated herein in full by reference. The cultures can achieve higher lipid contents (~32 hrs) sooner than the two-stage system (~48 hrs) in the batch.

Figure 40:
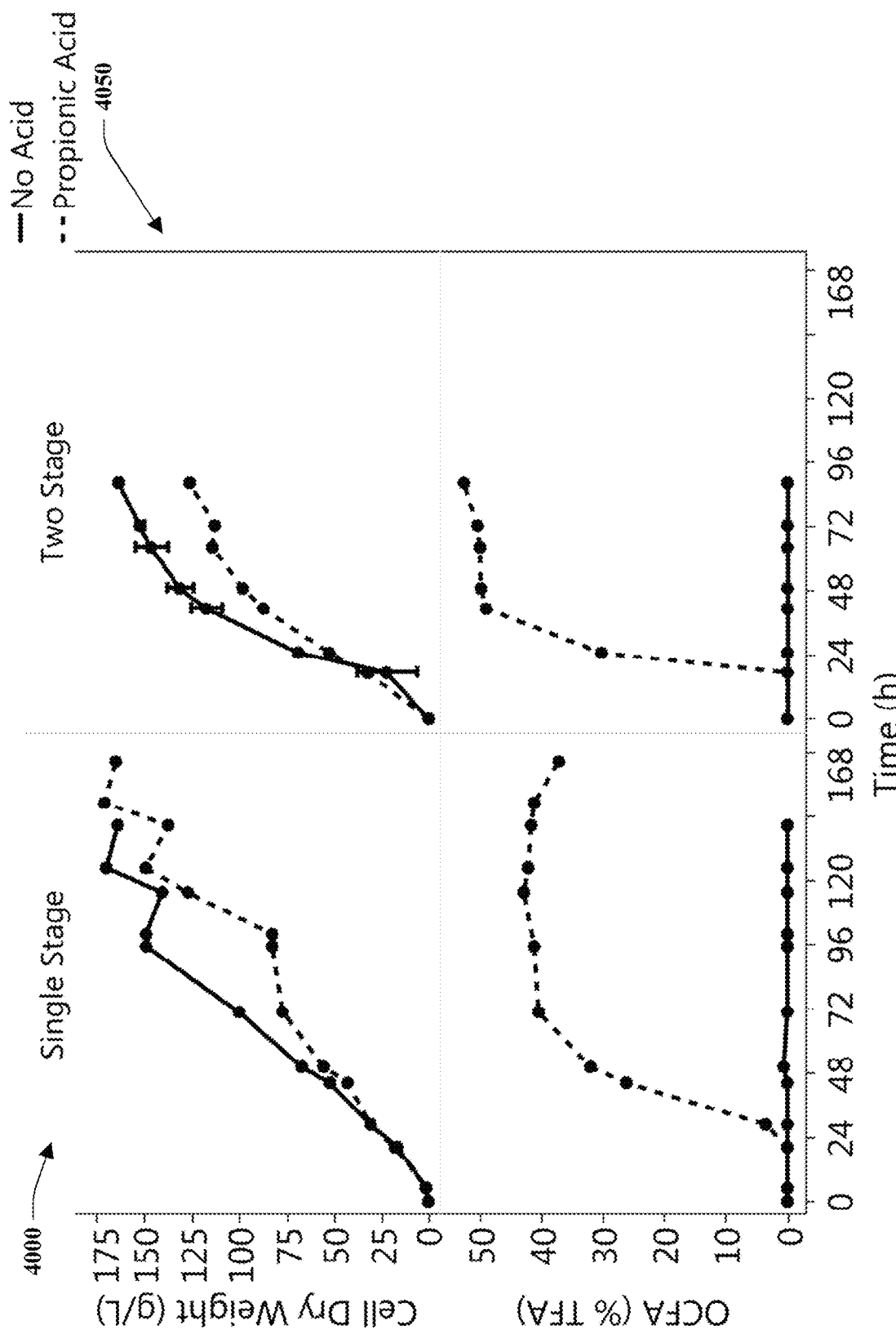
FIG. 40 is a graphical representation showing the impact of propionic acid exposure on *A. acetophilum* HS399 growth and odd chain fatty acid production in 10 L fermenters under two different growth modes.

FIG. 40 is a graphical representation of two results 4000, 4050 of the impact of propionic acid exposure to *A. acetophilum* HS399 growth and odd chain fatty acid production in 10 L Bioflo320 fermenters under single 4000 or two-stage mode 4050. In this implementation, propionic acid can be fed fed-batch in a pH-auxostat mode (e.g., propionic acid can also be used as the pH titrant) 24 hrs after inoculation to experimental treatments in order to illustrate the impact of the growth mode in propionic acid toxicity. Each of the four treatments can be cultured in duplicate (n=2) fermenters. As illustrated in Table 20 below, the growth rate can be determined, along with the amount of propionic acid fed throughout the culture. As illustrated, propionic acid slows down the growth on both systems, but the two-stage system provides a better growth rate than the single stage system in the presence of propionate. Additionally, the accumulation of OCFA in lipids (% TFA) is improves when propionic acid is fed in a two-stage process, for example, because no lipids (e.g., consisting of even chain fatty acids) may be produced in the absence of propionate (0-24 h). This implementation illustrates that the traditional two stage approach to lipid accumulation may be preferable to produce OCFAs.

TABLE 20

Impact of propionic acid exposure to *Aurantiochytrium acetophilum* HS399 biomass yield and productivity under single or two-stage mode

| | Single Stage | | Two Stage | |
|---|---|---|---|---|
| | No Acid | Propionic Acid | No Acid | Propionic Acid |
| Batch Time (h) | 96 h | 96 h | 89 h | 89 h |
| Biomass Yield (g/L) | 148.8 | 82.5 | 163.6 | 125.8 |
| Productivity (g/L/d) | 37.4 | 20.7 | 44.3 | 34.1 |

Double Ammonia-Propionic Acid/pH-Auxostat Process:

Based on the results from the implementations described above, in one implementation, a fermentation process can be used to produce OCFAs under a two-stage growth mode, where ammonia is used as a nitrogen source and propionate is used as a promotor of OCFAs. Glucose can also be fed in a $DO_2$ stat mode in response to dissolved oxygen levels rising above 15% saturation. Previously, as illustrated herein, fed-batch may be preferred to batch because it can reduce propionic acid toxicity (e.g., "Mitigate propionic toxicity: Batch vs. fed-batch"). Further, as illustrated herein, propionic acid toxicity can be modulated with the propionate concentration and the pH of the media (e.g., "Establishing propionic acid toxicity limit"). Therefore, a pH-auxostat system can be used to maintain low residual concentrations of those nutrients in a fed-batch mode, while controlling their toxicity through the pH set point.

Molar $NH_3$/NaOH Ratio of the Fed

Figure 41:
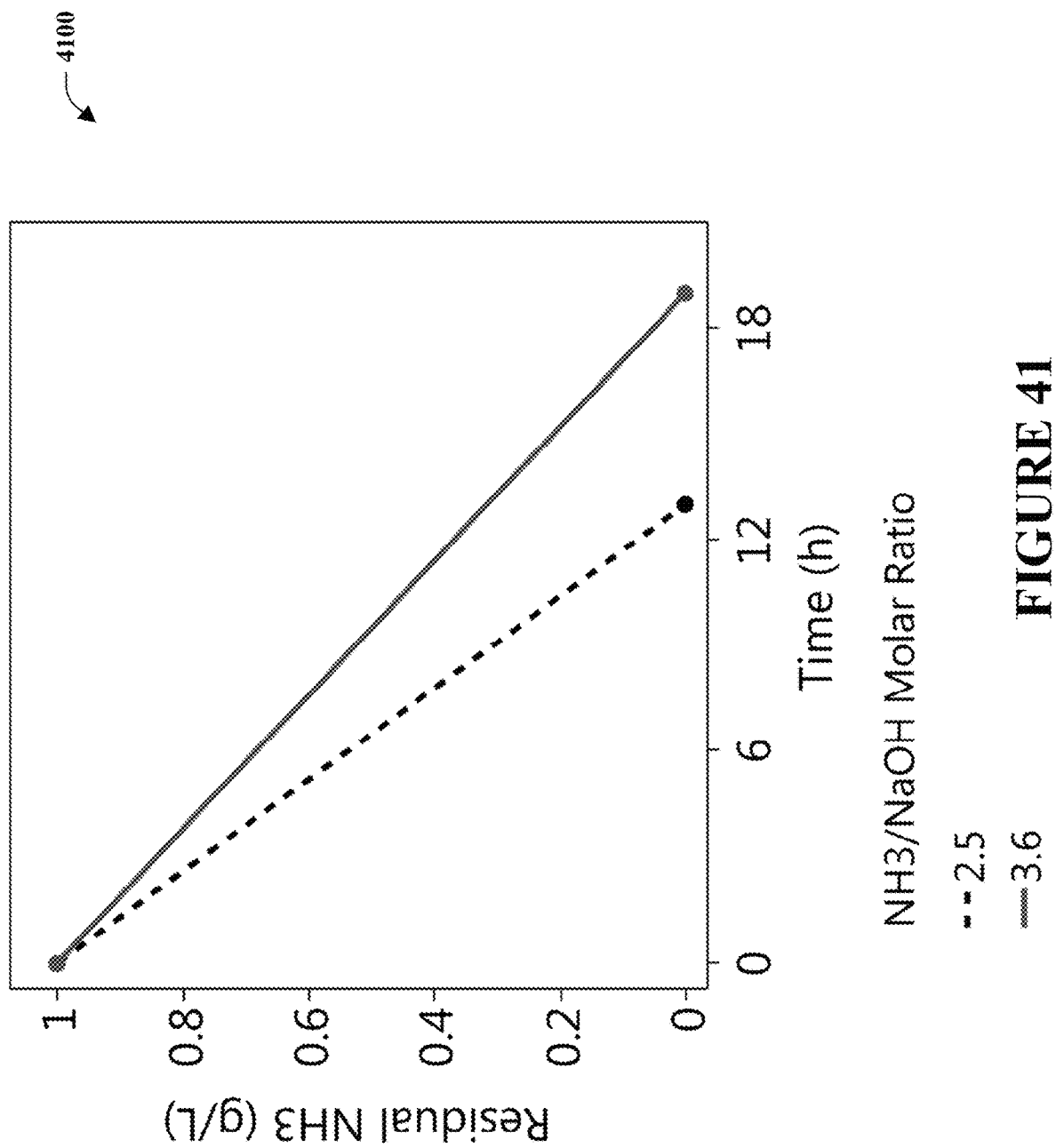
FIG. 41 is a graphical representation illustrating results of one implementation, where, much like the two-stage growth mode described above, ammonia can be fed merely during the growth phase.

FIG. 41 is a graphical representation illustrating results 4100 of one implementation, where, much like the two-stage growth mode described above, ammonia can be fed merely during the growth phase. In this implementation, the results 4100 illustrate the impact of ammonia to sodium hydroxide ratio of the fed in the residual ammonia concentration of a double auxostat culture of *A. acetophilum* HS399. In this implementation, ammonia can be gradually displaced from the media as the sodium hydroxide from the feed interferes with the titration of the ammonia/pH-auxostat. The feeding of propionic acid can be postponed until the lipid phase (~15-25 hrs) based on the results obtained in example "Mitigate propionic toxicity: Growth vs. lipid phase," described above.

As a result, in this implementation, a double ammonia propionic/pH-auxostat can be used, where ammonia is fed on demand during growth phase and propionate is fed on demand during the lipid phase (e.g., a two-stage process). To accommodate both auxostats, a transition can be used that would provide for the absence of ammonia during the lipid phase, which otherwise can interfere with the propionic acid auxostat titration. In this implementation, an inert base (e.g., sodium hydroxide) can be blended with the ammonia feed in a specific ratio. The sodium hydroxide titrates the pH irreversibly, gradually displacing the residual ammonia in the medium until it is completely depleted, as shown by the results 4100. As illustrated, ammonia depletion can stop the auxostat feed, which indicates the end of the growth phase and the beginning of the lipid phase. The rate of ammonia depletion, and therefore the total ammonia fed, for example, can increase with decreasing ammonia-sodium hydroxide ratio.

Figure 42:
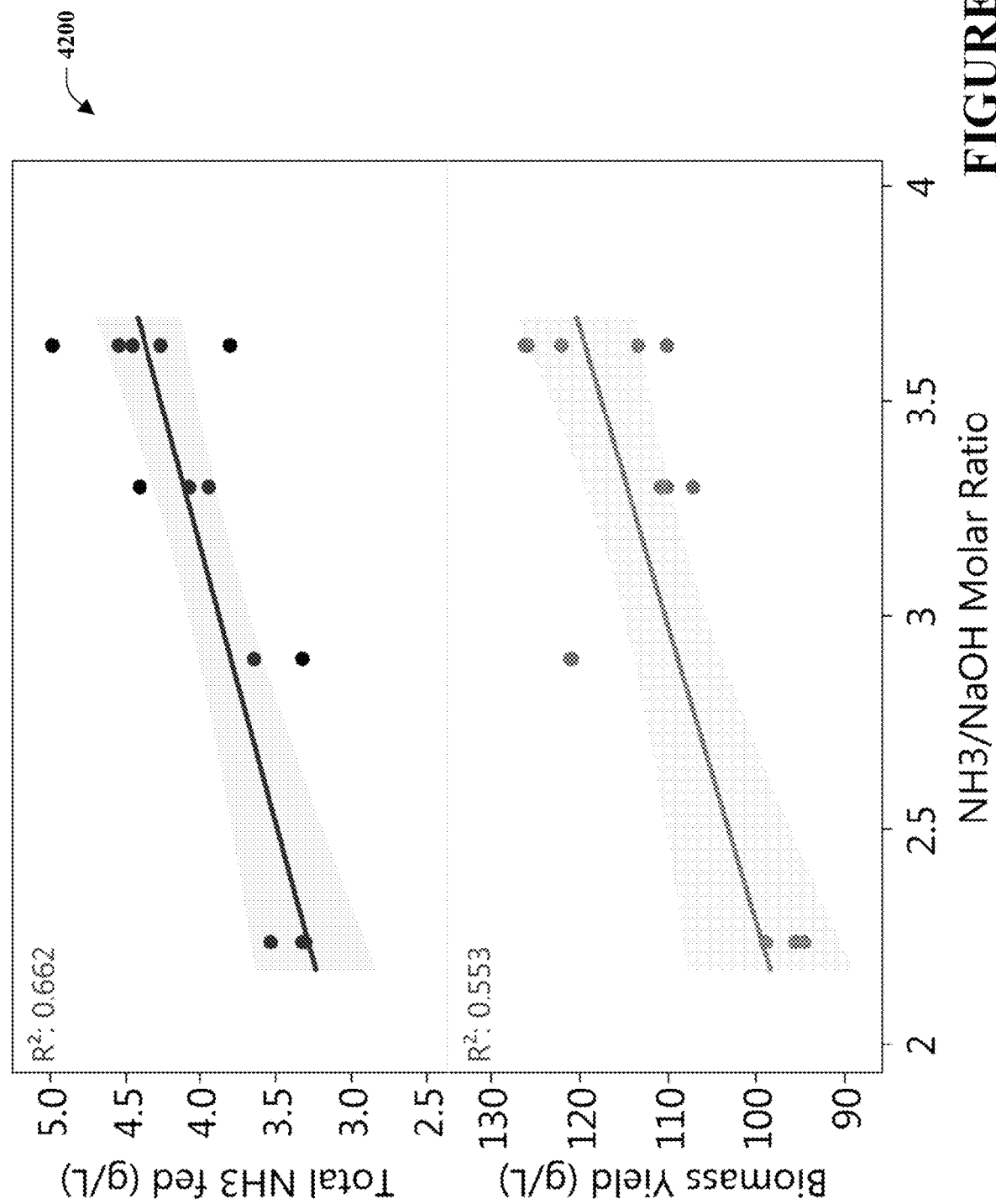
FIG. 42 is a graphical representation illustrating results of one implementation, applying the impact of ammonia to sodium hydroxide ratio of the feed in the total ammonia fed and biomass yields of a double auxostat culture of *Aurantiochytrium acetophilum* HS399.

FIG. 42 is a graphical representation illustrating results 4200 of one implementation, applying the impact of ammonia to sodium hydroxide ratio of the fed in the total ammonia fed and biomass yields of a double auxostat culture of *A. acetophilum* HS399. In this implementation, the results 4200 illustrate the total ammonia fed to the culture and the resulting biomass yields can also be controlled by the ammonia to sodium hydroxide ratio. Further, the results 4200 indicate that the ammonia to sodium hydroxide ratio in the fed is a component for the control and operation of the double auxostat system. For example, this control may also be applied with a different inert base, such us potassium hydroxide or calcium hydroxide.

Toxicity Control Through a pH Ramp

Figure 43:
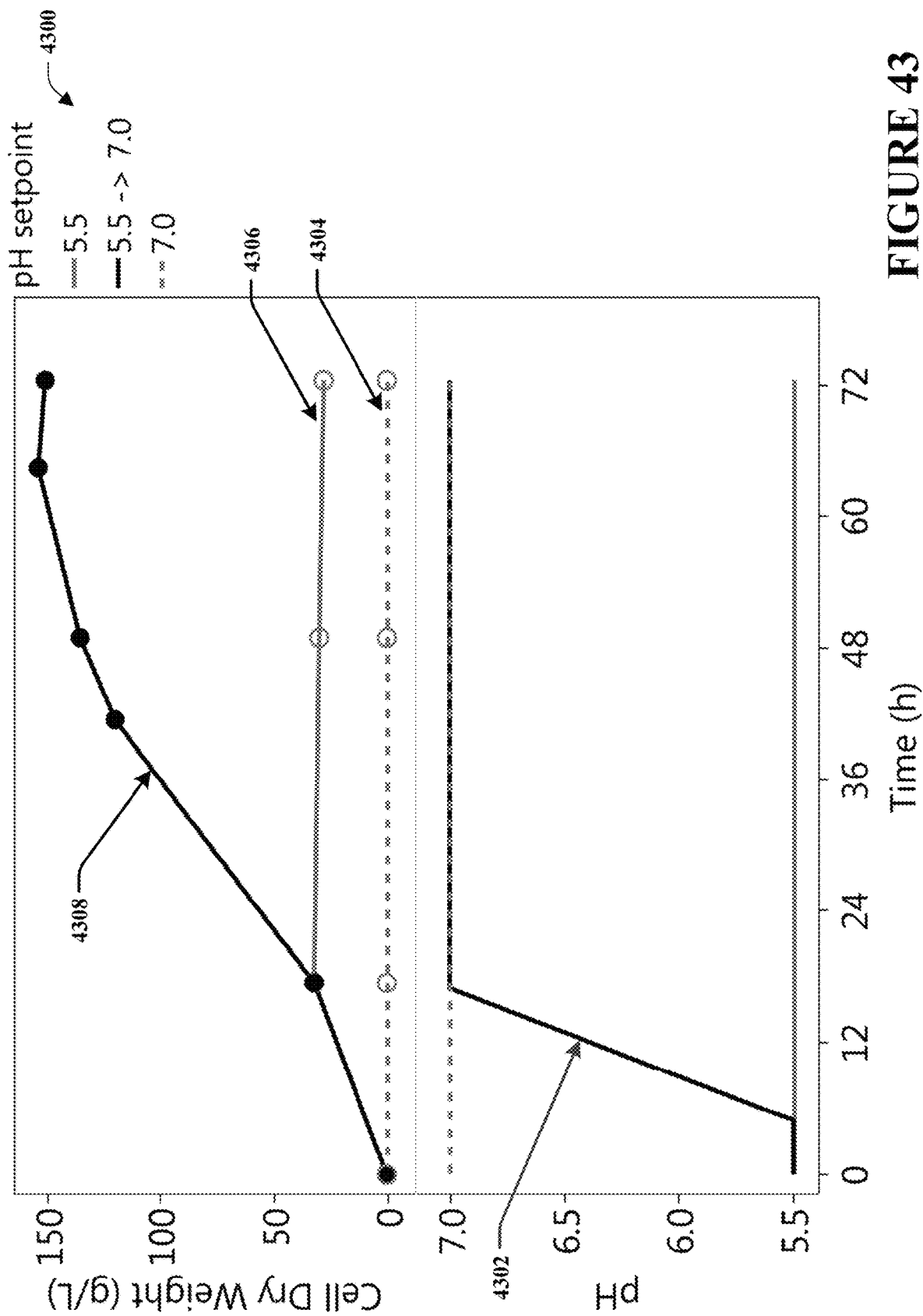
FIG. 43 is a graphical representation illustrating results of one implementation, describing the impact of pH set-point control in the transition of ammonia to propionic acid pH auxostat culture of *Aurantiochytrium acetophilum* HS399.

In one implementation, using the model described above in "Establishing propionic acid toxicity limit" a pH to provide a desired balance of the toxicity of both propionic acid and ammonia can be determined. For example, using this method, there may not be a specific pH that can accommodate the toxicity of both nutrients. FIG. 43 is a graphical representation illustrating results 4300 of one implementation, describing the impact of pH set-point control in the transition of ammonia to propionic acid pH auxostat culture of *A. acetophilum* HS399. As illustrated, the pH ramp 4302 is used to sustain the growth of HS399. As illustrated, when *A. acetophilum* HS399 is grown in a double pH-auxostat at a pH set-point of 7.0 4304, ammonia toxicity can inhibit its growth. Further, when *A. acetophilum* HS399 is grown at a pH of 5.5 4306 the ammonia toxicity can be greatly reduced, but the cells can be inhibited by propionate at the beginning of the lipid phase. Additionally, a ramp 4302 can be applied where pH set-point can be steadily increased from 5.5 to 7 between hour 5 to hour 17 of fermentation, which can coincide with the end of the growth phase when residual ammonia was at a low point. In this example, the pH ramp can mitigate the toxicity of both nutrients and improve the growth rate for the culture through the two-stage process 4308.

Activating and Maintaining the Propionic Acid pH Auxostat

Figure 44:
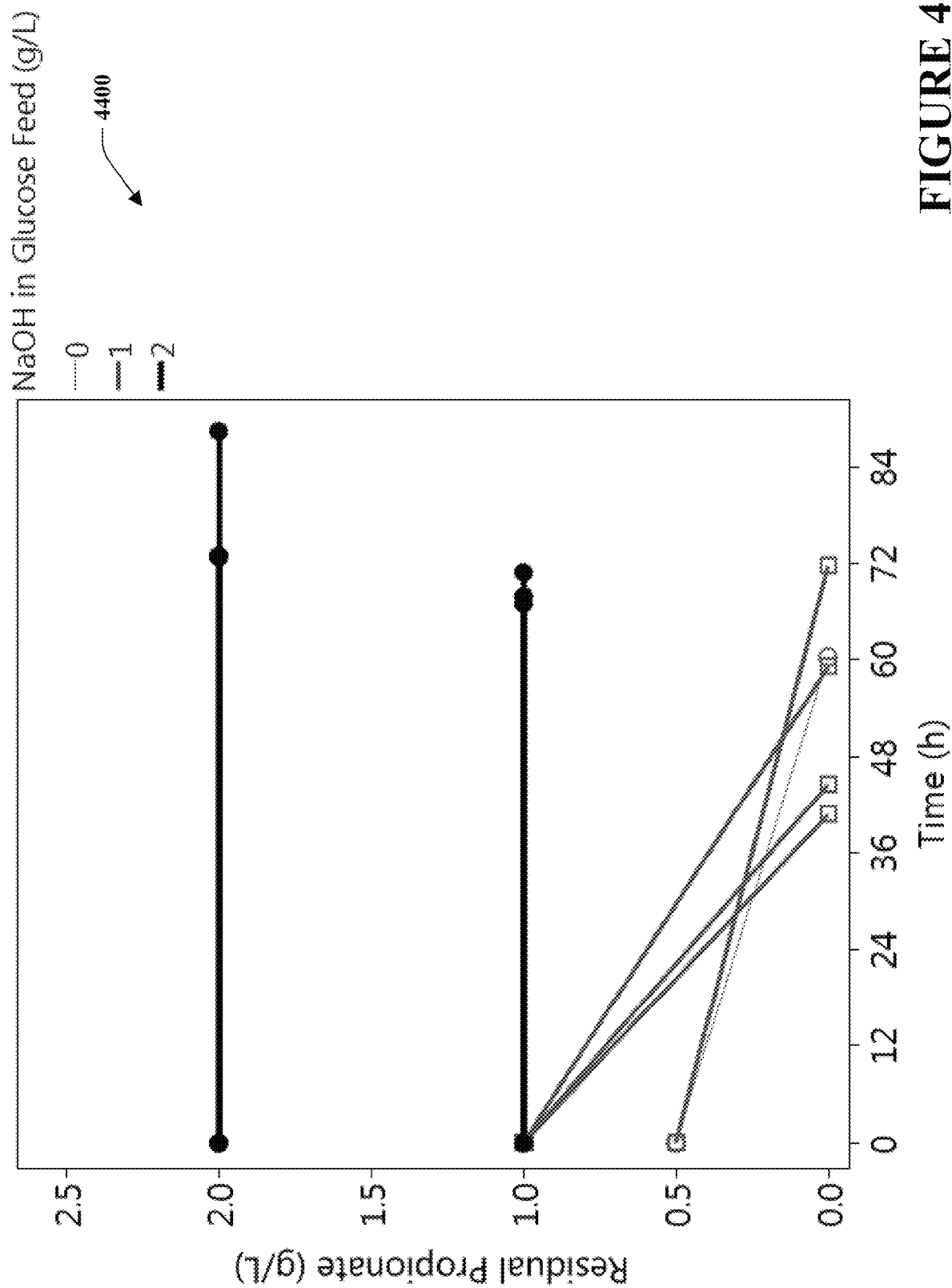
FIG. 44 is a graphical representation illustrating results for *Aurantiochytrium acetophilum* HS399 double pH-auxostat cultures, showing the impact of sodium hydroxide supplementation into the glucose fed in the residual propionic acid control in a pH-auxostat.

FIG. 44 is a graphical representation illustrating results 4400 for *A. acetophilum* HS399 double pH-auxostat cultures, showing the impact of sodium hydroxide supplementation into the glucose fed in the residual propionic acid control in a pH-auxostat. In this implementation, the propionic acid pH-auxostat can be implemented throughout the lipid phase to improve the synthesis of OCFAs in *A. acetophilum* HS399. The lipid phase can begin when the ammonia feed naturally stops the addition. At this point, 1-3 g/L of residual propionate can be added into the culture. The propionate can be added as a salt (e.g., sodium propionate) or as an acid, in response to the simultaneous titration of sodium hydroxide that is slowly (pH 7±0.2) introduced in the reactor. In this implementation, as soon as *A. acetophilum* HS399 starts consuming the propionate, the pH raises, which provides for more propionate and activation of the auxostat. In one implementation, the auxostat can be maintained to keep the residual propionate levels constant, however, the residual propionate may slowly decrease, which may be due to other cell metabolites interfering with the titration, as shown in FIG. 44. In order to overcome the slow decrease, 1-2 g of sodium hydroxide can be introduced in respective liters of the glucose feed. In this implementation, the alkalization can help maintain the residual propionate constant and avoid the early interruption of propionate fed that may otherwise occur.

Example 13—Propionate Concentration and OCFA Titers

In one implementation, the variation of propionate fed to *Aurantiochytrium acetophilum* HS399 cultures is reflected in the OCFA titers of the final biomass. In this example, five treatments containing different concentrations of propionate: 0, 2, 3, 4, 5 g/L respectively. Respective Erlenmeyer flasks (250 mL) are inoculated (1% v/v) in triplicates with a 24 h old culture of *A. acetophilum* HS399 and incubated in an orbital shaker at 180 rpm and 27° C.

Respective Erlenmeyer flasks contain 100 mL of a medium supplemented with (g/L): dextrose (100), ammonium acetate (4.6), NaCl (12.5), $MgSO_4$ $7H_2O$ (2.5), $KH_2PO_4$ (0.5), KCl (0.5) and $CaCl_2$ (0.1). This medium also contains trace element solution (5 ml/L) and vitamin solution (1 ml/L). The trace element solution contains (g/L): EDTA di-sodium salt (6), $FeCl_3$ $6H_2O$ (0.29), $H_2BO_3$ (6.84), MnCl$_2$ 4H$_2$O (0.86), ZnCl$_2$ (0.06), NiSO$_4$ 6H$_2$O (0.052), CuSO$_4$ 5H$_2$O (0.002), Na$_2$MoO$_4$H$_2$O (0.005). The vitamin solution contains (mg/L): thiamine (100) and biotin (0.5).

In this example, respective culture materials are autoclaved (e.g., 121° C., 15 min) and the media is filter sterilized before use. A propionic acid stock solution (200 g/L) can be used as the fed propionic acid. Daily samples are collected to analyze the cell dry weight, residual glucose, culture pH and lipid and fatty acid composition of the cultures. Cell dry weights are analyzed by filtration (e.g., 0.2 μm filter media) using a vacuum and washed with a solution of ammonium bicarbonate. Residual glucose is analyzed using a colorimetric method based on glucose peroxidase activity. Biomass for lipid analysis is centrifuged and washed using purified water. The washed biomass is freeze dried. Total lipids are analyzed using Folch method (AOAC 996.06) and the FAMEs are analyzed by gas chromatography and flame ionization detection using nonadecanoic (C19:0) acid as an internal standard.

As shown in Table 21, the results illustrate that the different propionate concentrations yield different odd chain fatty acid concentration. The results show that a wide range of OCFA concentration in the oil can be produced by varying the propionate concentration in the culture.

In this implementation, the glucose solution can be fed in a ramp from 0 to 0.2 mL/min L initially (e.g., from 8 to 20 h elapsed fermentation time), and from 20 h onwards the DO$_2$-stat triggered glucose feed can pulse 102 min at 0.3 mL/min L. The pH can be controlled with the ammonia fed at 5.5 during growth phase and propionic acid at 7.0 during lipid phase. The pH can be raised from 5.5 to 7.0 gradually between 5 and 17 h when residual ammonia is at a low point. Upon the ammonia running out of the culture (e.g., nitrogen feeding stopped), 1 g/L of NaOH can be slowly added while correcting the pH (7.0±0.5) with propionic acid (glacial). In this example, after this point, the pH can be controlled with the propionic feed. As one example, foam can be controlled (e.g., manually or automatically) using less than 1 mL/L of HODAG K-60 defoamer.

In this implementation, the 1000 L pilot fermenter can be filled with 400 L of batch media and fed with another 400 L of glucose feed media, and 40 L of ammonia fed, which may result in a final working volume of ~850 L. The example compositions of respective media are illustrated in in Table 22, and the trace metal solution is shown in Table 23, below, along with vitamin mix contained 100 mg of thiamin and 0.5 mg/L of biotin. The medium chemicals can be dissolved in the order listed on the tables, for example,

TABLE 21

Total lipids and fatty acid profile at time of harvest (96 h)

| Propionate (g/L) | 0 | 2 | 3 | 4 | 5 |
|---|---|---|---|---|---|
| Total Fatty Acids (% DW) | 62.7 ± 0.8 | 54.8 ± 5.6 | 56.2 ± 0.6 | 39.2 ± 12.4 | 41.0 ± 3.4 |
| Fatty Acid Profile (% TFA) | | | | | |
| 13:0 | 0.0 ± 0.0 | 1.6 ± 0.1 | 2.6 ± 0.1 | 4.2 ± 0.4 | 5.1 ± 0.7 |
| 14:0 | 3.7 ± 0.0 | 3.0 ± 0.2 | 2.4 ± 0.1 | 1.8 ± 0.3 | 1.9 ± 0.2 |
| 15:0 | 0.7 ± 0.0 | 25.2 ± 1.5 | 41.6 ± 0.9 | 51.6 ± 2.6 | 53.0 ± 0.4 |
| 16:0 | 51.5 ± 0.4 | 31.7 ± 1.3 | 17.0 ± 1.1 | 6.4 ± 0.5 | 5.7 ± 0.5 |
| 17:0 | 0.3 ± 0.0 | 3.9 ± 0.4 | 6.7 ± 0.3 | 7.2 ± 0.3 | 6.6 ± 0.7 |
| 18:0 | 1.9 ± 0.3 | 0.9 ± 0.0 | 0.5 ± 0.0 | 0.1 ± 0.1 | 0.1 ± 0.1 |
| 22:5 (n-6) | 7.4 ± 0.1 | 5.1 ± 0.2 | 4.0 ± 0.2 | 2.7 ± 0.4 | 2.8 ± 0.1 |
| 22:6 (n-3) | 33.0 ± 0.5 | 26.6 ± 0.6 | 23.4 ± 0.4 | 22.8 ± 1.9 | 21.9 ± 0.6 |
| Other FA | 1.4 ± 0.3 | 1.6 ± 0.0 | 1.7 ± 0.0 | 2.7 ± 1.2 | 2.2 ± 0.3 |
| OCFA (% TFA) | 0.9 ± 0.0 | 30.7 ± 1.8 | 50.8 ± 1.1 | 63.0 ± 2.5 | 64.6 ± 0.3 |

Example 14—Anaplerotic Process in 1000 L Pilot Fermenter

In one implementation, the processes described herein can be scaled up into a larger pilot facility, such as a 1000 L pilot facility, in duplicates fermenters (n=2). For example, the pilot facility may be reflective of the production in larger reactors of up to 180,000 L. In this implementation, the seed cultures can be scaled up from a 1 mL cryovial, into a 100 ml Flask, a 7 L wave bag, a 79 L fermenter, and the pilot fermenter with 800 L running volume. Thus, as an example, the cultures can be inoculated at 5% v/v, although 1% v/v inoculation may also be utilized. In this implementation, the fermenter cultures can be aerated at 1.3 vvm (volume of air per volume of culture per min) and agitated with Rushton impellers, for example, at 60 rpm in a dissolved oxygen (DO$_2$) cascade control. As one example, rpm may increase, but not be decreased, in response to DO$_2$, at levels below 10% saturation. In this implementation, the temperature can be controlled at 27±1° C. Further, the pressure can be controlled at (0.7-2 kg/cm$^2$), for example, in response to excessive foaming or rpm at its high limit. Additionally, corn syrup 95DE can be fed in a DO$_2$-stat mode at 800 g/L glucose in response to DO$_2$ levels rising above 15%.

and the pH of the media can be adjusted to 5.5 using NaOH. The volume of the culture can be raised up to 345 L, accounting for another 35 L of condensation during a steam sterilization process (121° C.×30 min). In this implementation, the batch media ingredients can be filter sterilized, except for the vitamin mix, which can be filter sterilized into the reactor. Glucose fed can be pre-heated through the jackets to mitigate excessive condensation during subsequent steam sterilization (121° C.×30 min). The sodium hydroxide can be added without sterilization once the sterilized tanks have cooled down to ~40° C. The ammonia feed can also be prepared without sterilization.

TABLE 22

Medium formulation for production of OCFAs by *Aurantiochytrium acetophilum* HS399 in double pH-auxostat system

| Chemicals | Units | Batch media | NH3-Feed Media | Glucose-Feed Media |
|---|---|---|---|---|
| Ammonium sulfate (NH$_4$)$_2$SO$_4$ | g/L | 3.89 | 81.55 | 0 |
| Potassium phosphate KH$_2$PO$_4$ | g/L | 5.0 | 0 | 0 |

TABLE 22-continued

Medium formulation for production of OCFAs by *Aurantiochytrium acetophilum* HS399 in double pH-auxostat system

| Chemicals | Units | Batch media | NH3-Feed Media | Glucose-Feed Media |
|---|---|---|---|---|
| Magnesium sulfate $MgSO_4\ 7 \cdot H_2O$ | g/L | 2.5 | 0 | 0 |
| Potassium chloride KCl | g/L | 1.0 | 0 | 0 |
| Calcium chloride $CaCl_2$ | g/L | 0.2 | 0 | 0 |
| Vitamin Mix | mL/L | 10 | 0 | 0 |
| Trace Metal Solution* *see table below* | mL/L | 50 | 0 | 0 |
| Corn syrup D95 | g/L | 37.5 | 0 | 1143 |
| Ammonium (29%) | mL/L | 0 | 238 | 0 |
| NaOH | g/L | 0 | 64.2 | 2.0 |

TABLE 23

Formulation of the trace metals solution (TMS)

| Chemicals | Quantity g/L | Required Quantity (g for 1 L) |
|---|---|---|
| EDTA disodium salt | 6 | 6 |
| $FeCl_3 \cdot 6H_2O$ Iron (III) Chloride hexahydrate (cloruro férrico) | 0.29 | 0.29 |
| $H_3BO_3$ Boric acid | 6.84 | 6.84 |
| $MnCl2 \cdot 4H2O$ Manganese chloride tetrahydrate | 0.86 | 0.86 |
| $ZnCl_2$ Zinc chloride | 0.06 | 0.06 |
| $CoCl_2 \cdot 6H_2O$ Cobaltous chloride | 0.026 | 0.026 |
| $NiSO_4 \cdot 6H_2O$ Nickel (II) Sulfate Hexahydrate | 0.052 | 0.052 |
| $CuSO_4 \cdot 5H_2O$ Copper (II) sulfate pentahydrate | 0.002 | 0.002 |
| $Na_2MoO_4 \cdot 2H_2O$ Sodium molybdate dihydrate | 0.005 | 0.005 |

In this implementation, the cultures can be monitored (e.g., periodically or continuously) for $T^a$ pH, DO2, oxygen uptake rate (OUR), rpm, and running volume. In this implementation, samples of cell dry weight, lipids, fatty acids, residual glucose, ammonia and propionate can be collected twice a day, or more.

Figure 45:
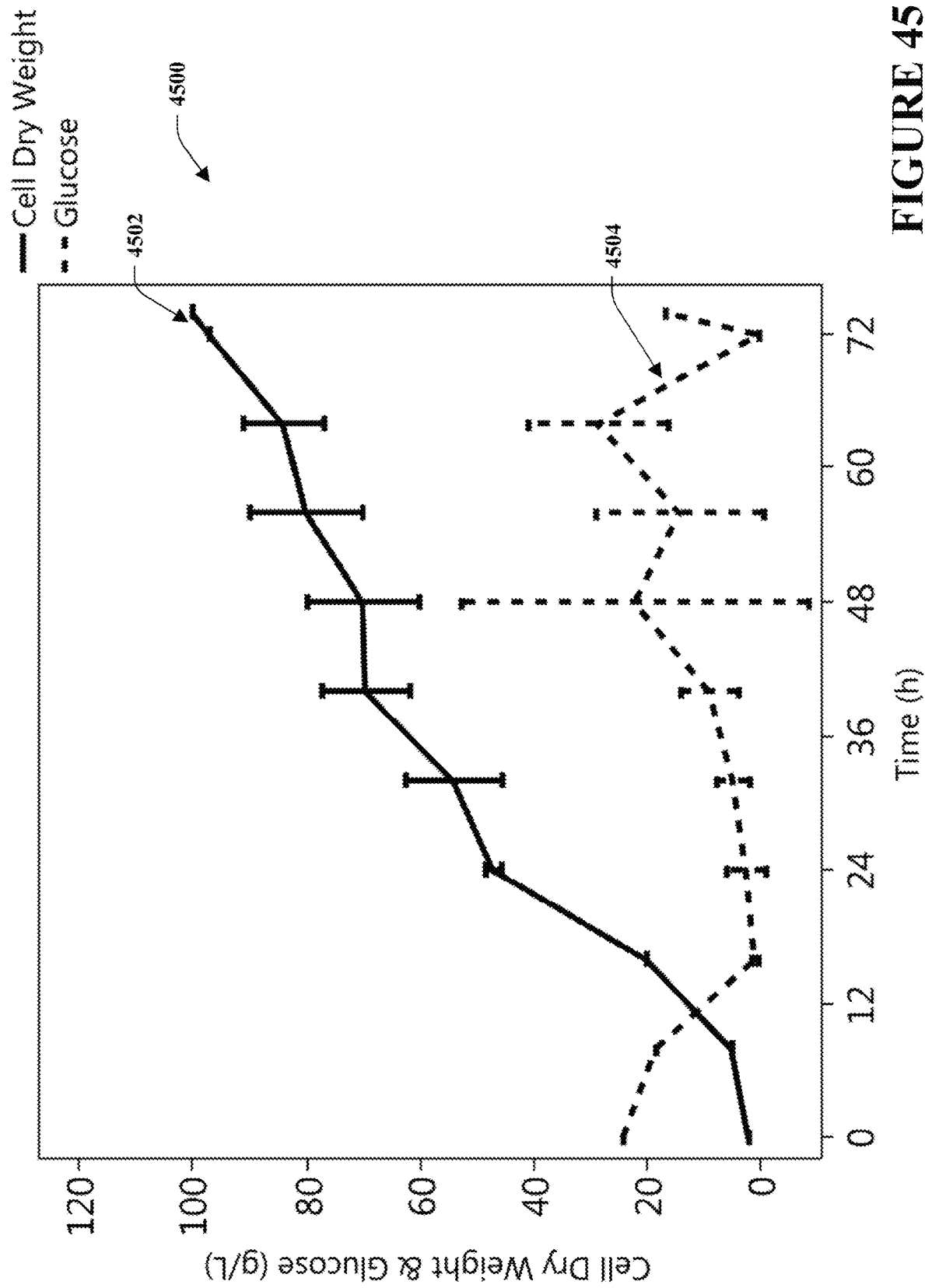
FIG. 45 is a graphical representation showing cell dry weight and residual glucose of *A. acetophilum* HS399 in a 100 L pilot fermenter.
Figure 46:
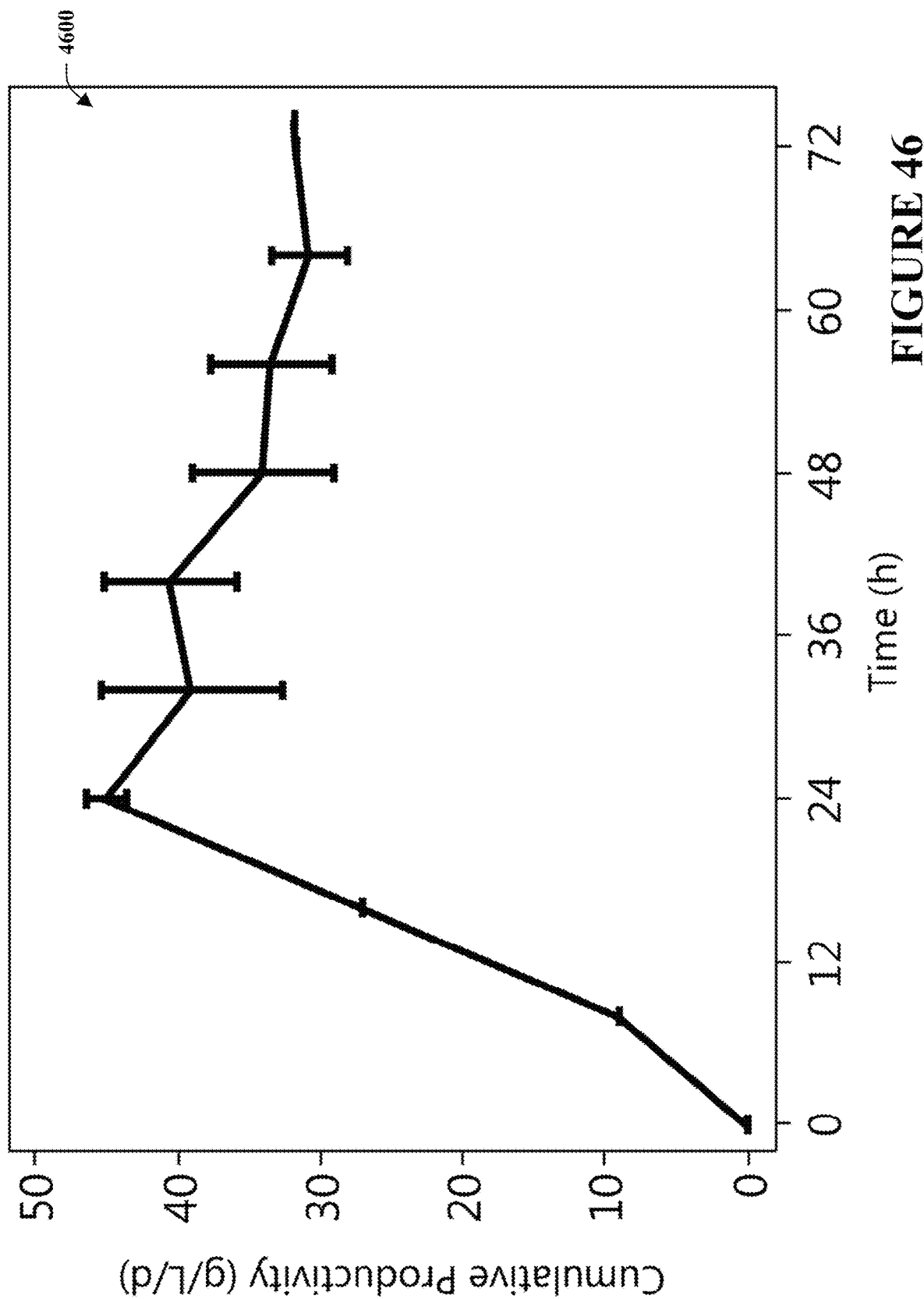
FIG. 46 is a graphical representation of the cumulative productivity of *A. acetophilum* HS399 in a 100 L pilot fermenter.
Figure 47A:
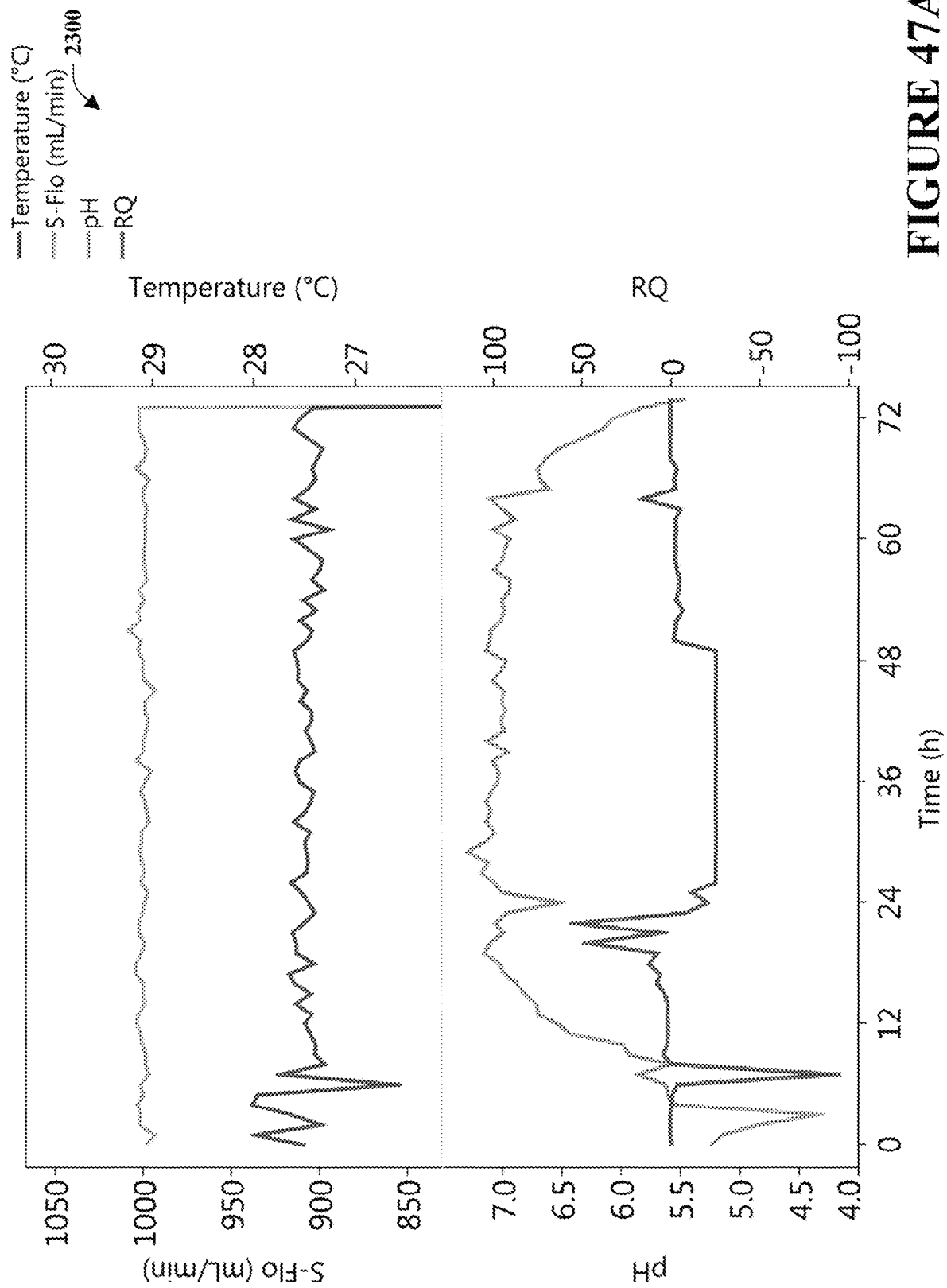
FIGS. 47A, 47B, 47C, 47D are graphical representations of online data readings exhibited by *A. acetophilum* SH399 in a 100 L pilot fermenter.
Figure 47B:
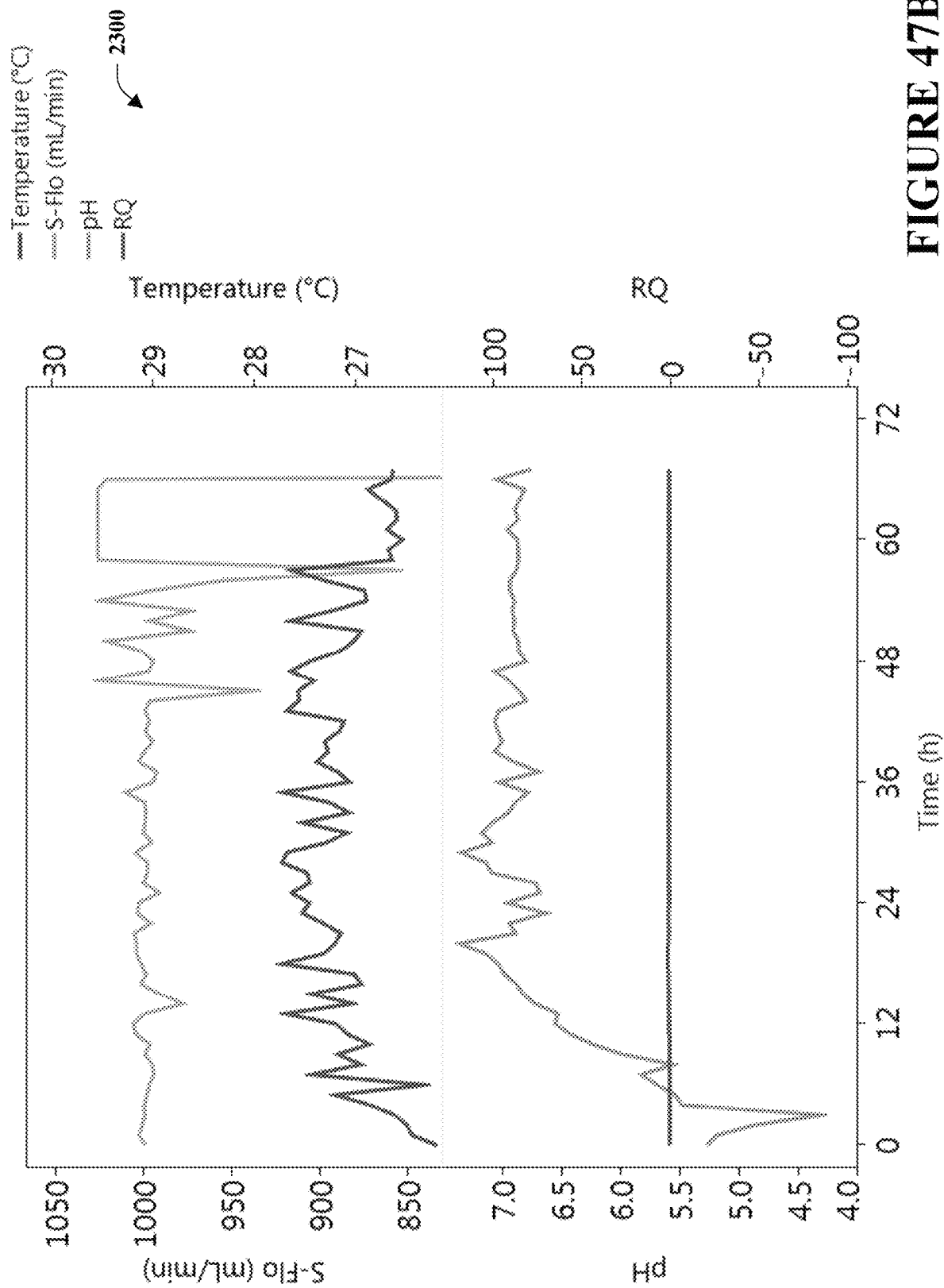
Figure 47C:
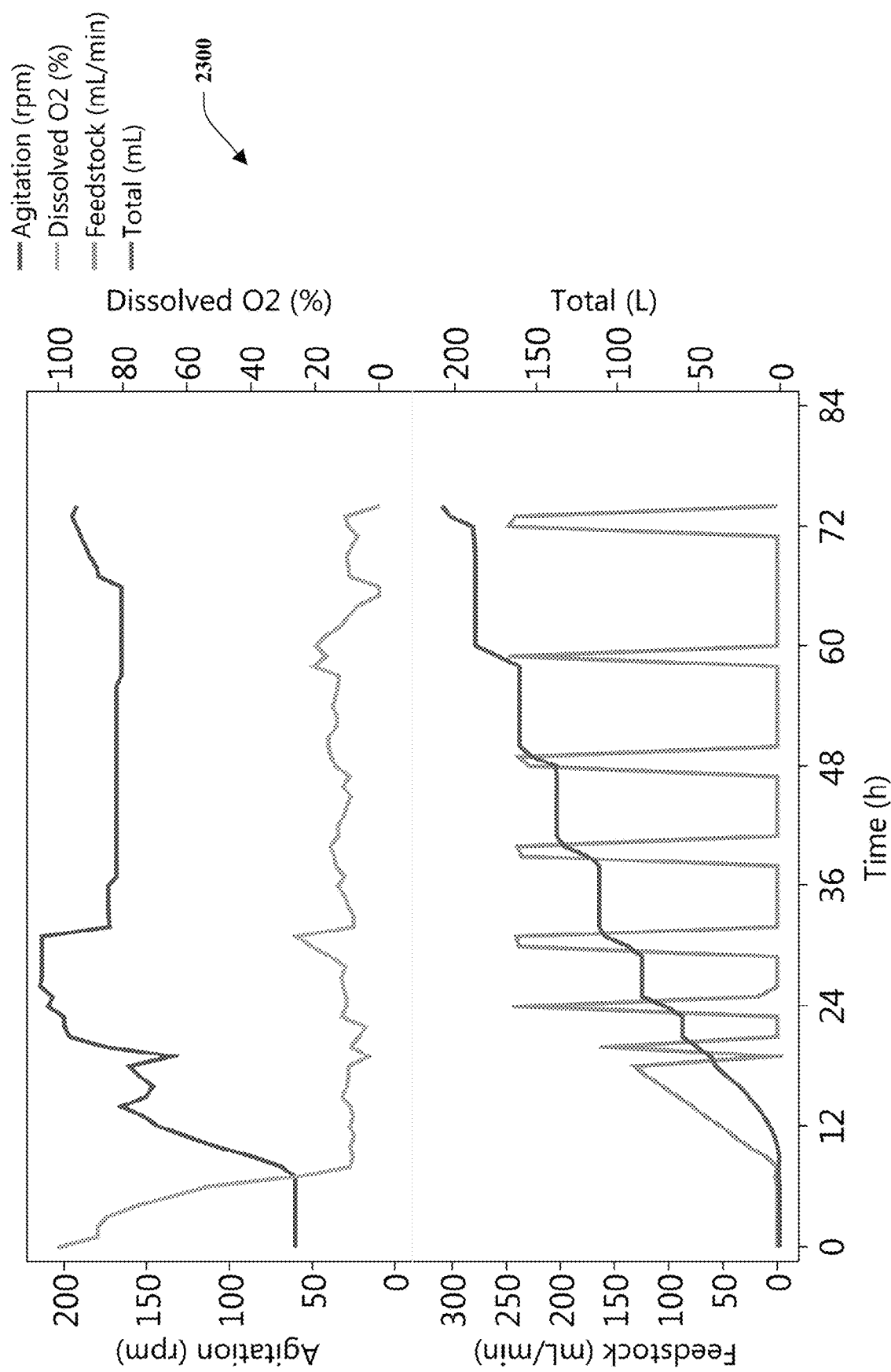
Figure 47D:
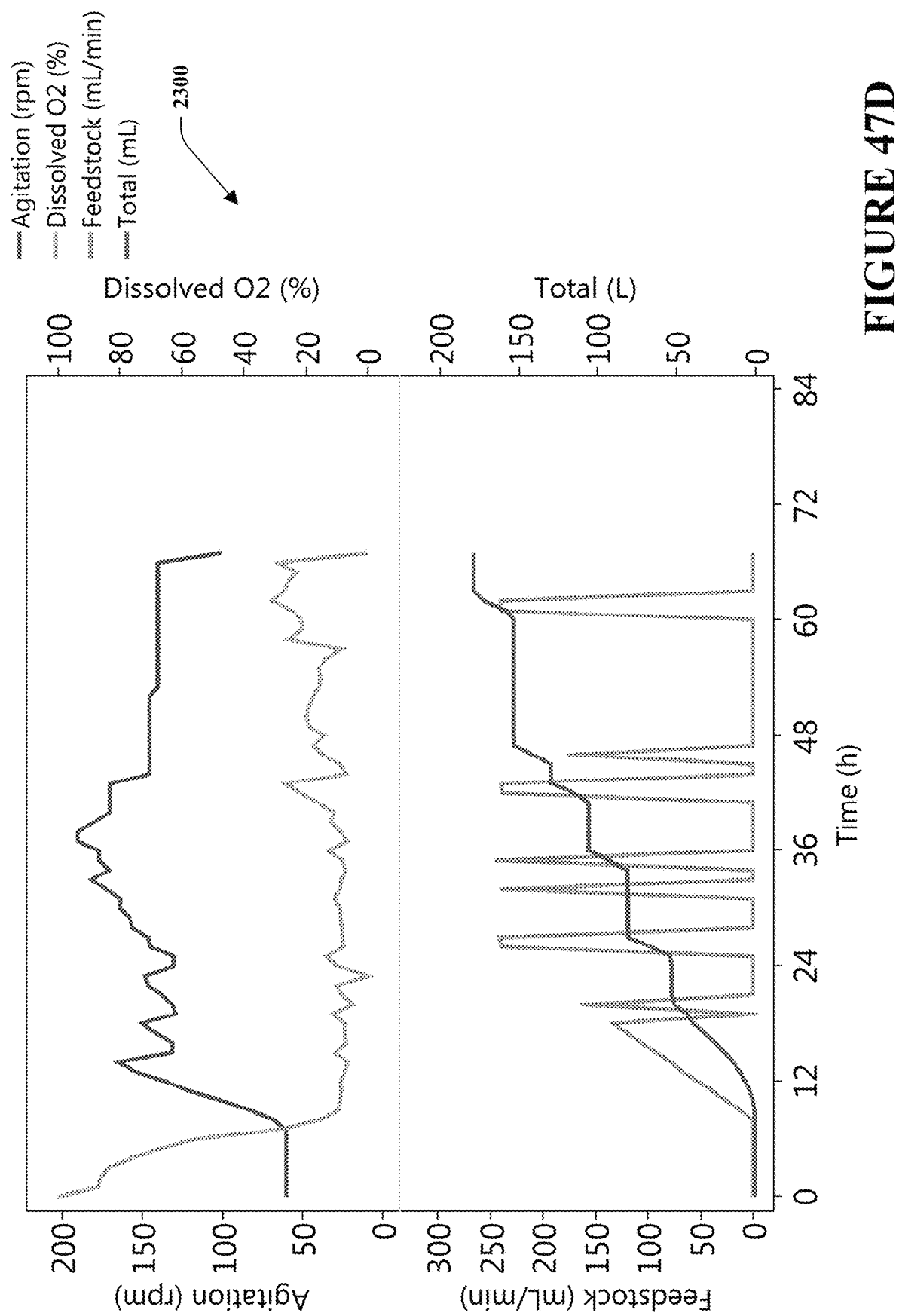
Figure 49A:
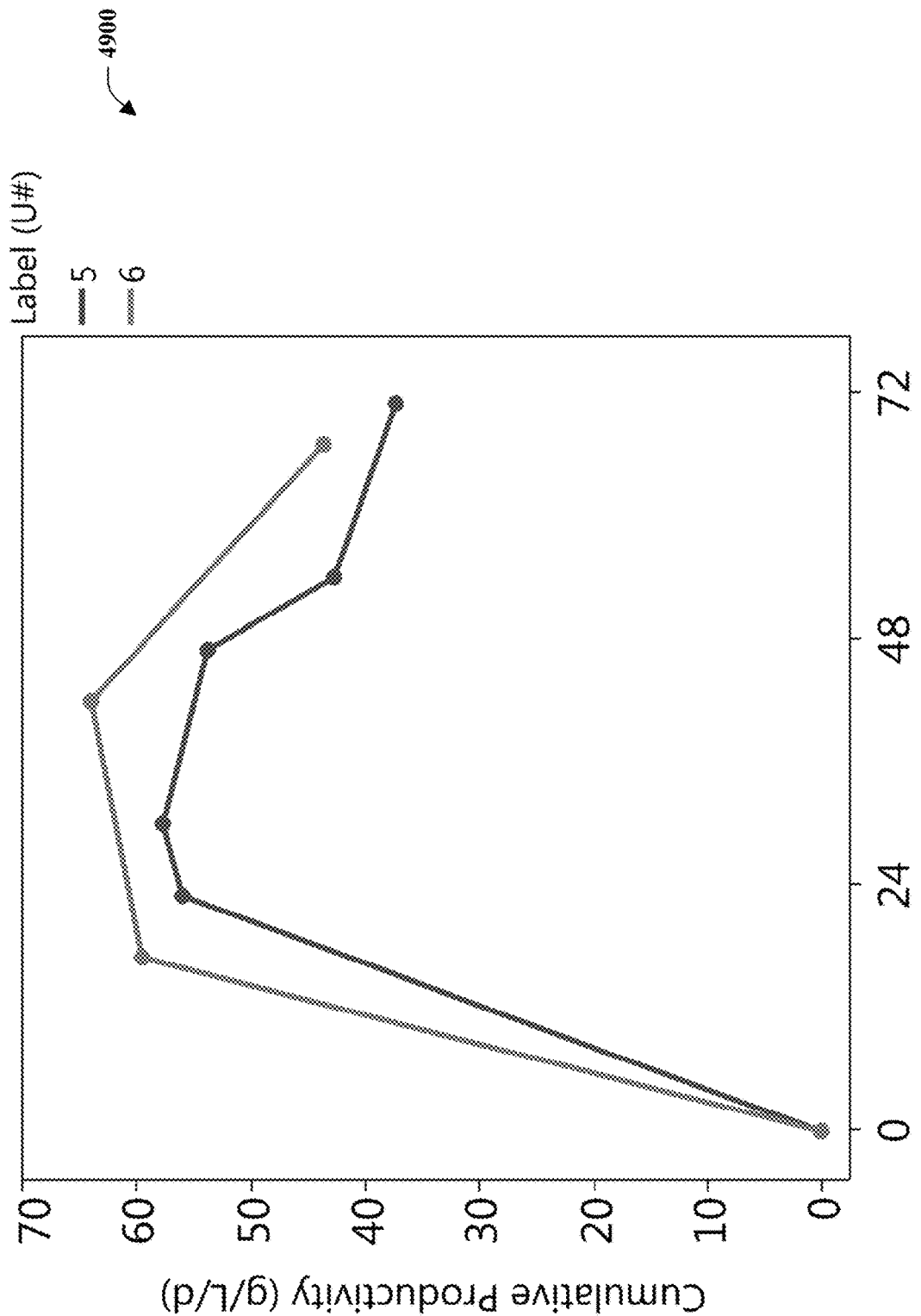
FIGS. 49A, 49B, 49C, 49D are graphical representations of *A. acetophilum* HS399 double pH-auxostat cultures for the production of odd chain fatty acids, growth productivity and lipid accumulation.
Figure 49B:
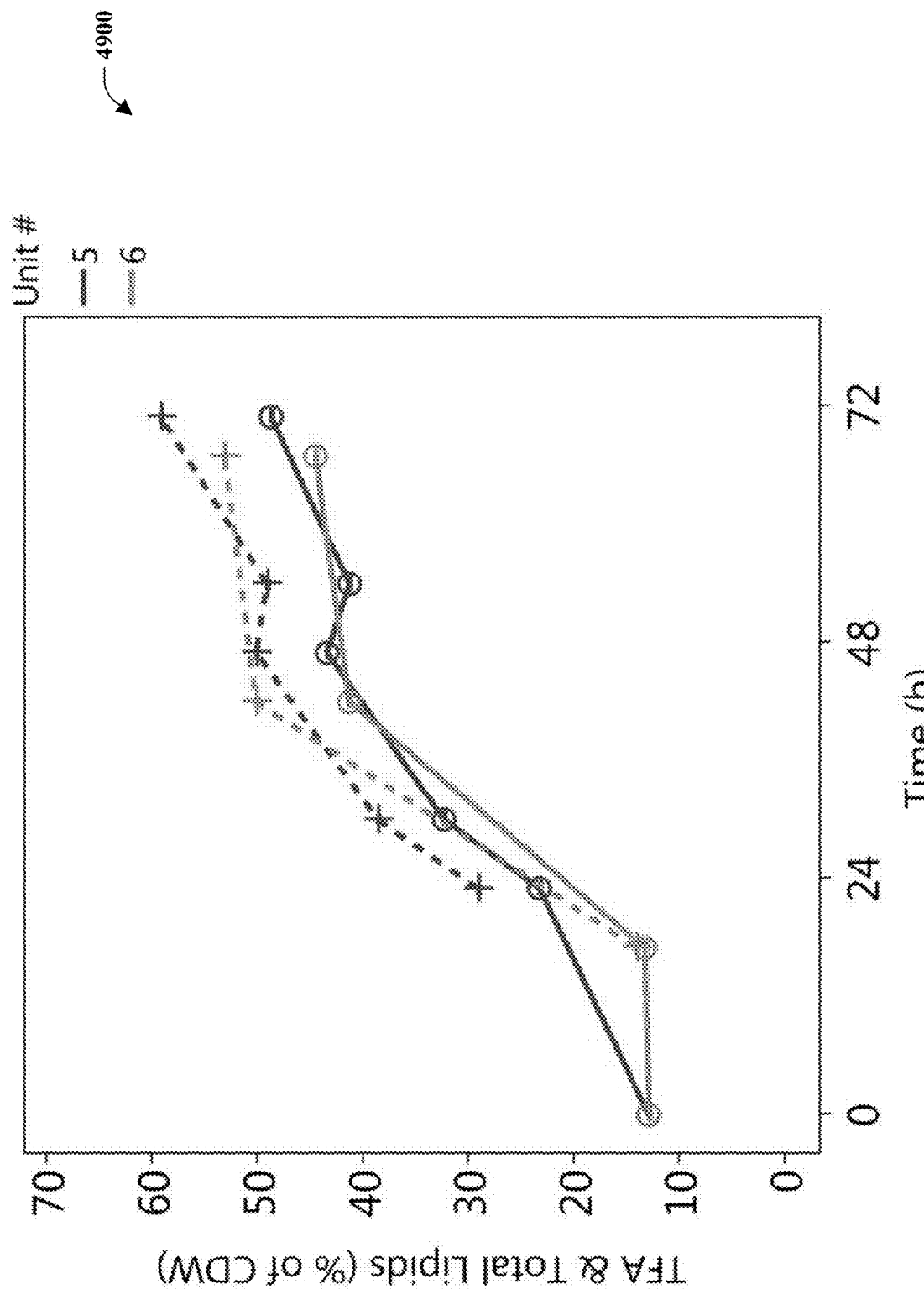
Figure 49C:
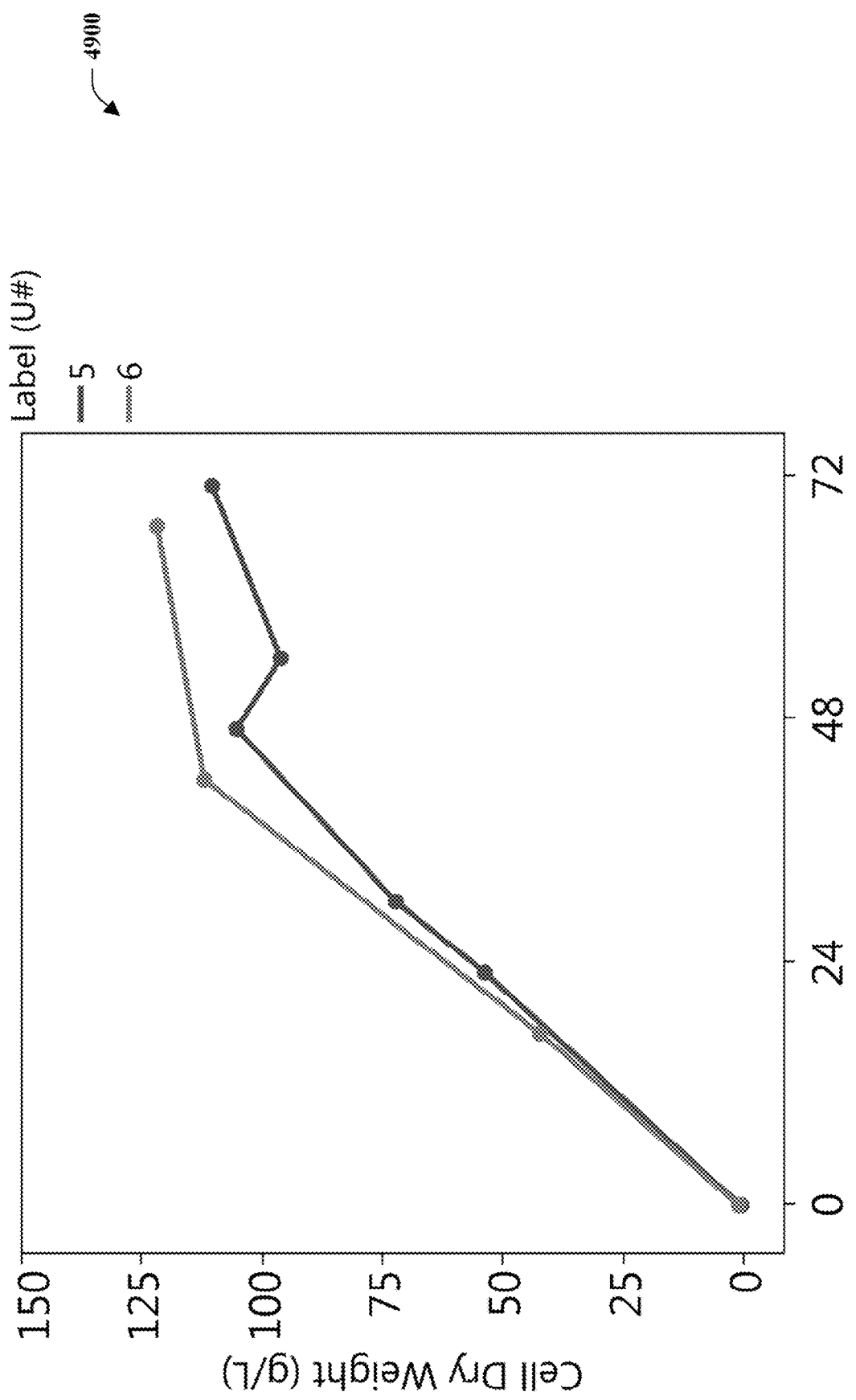
Figure 49D:
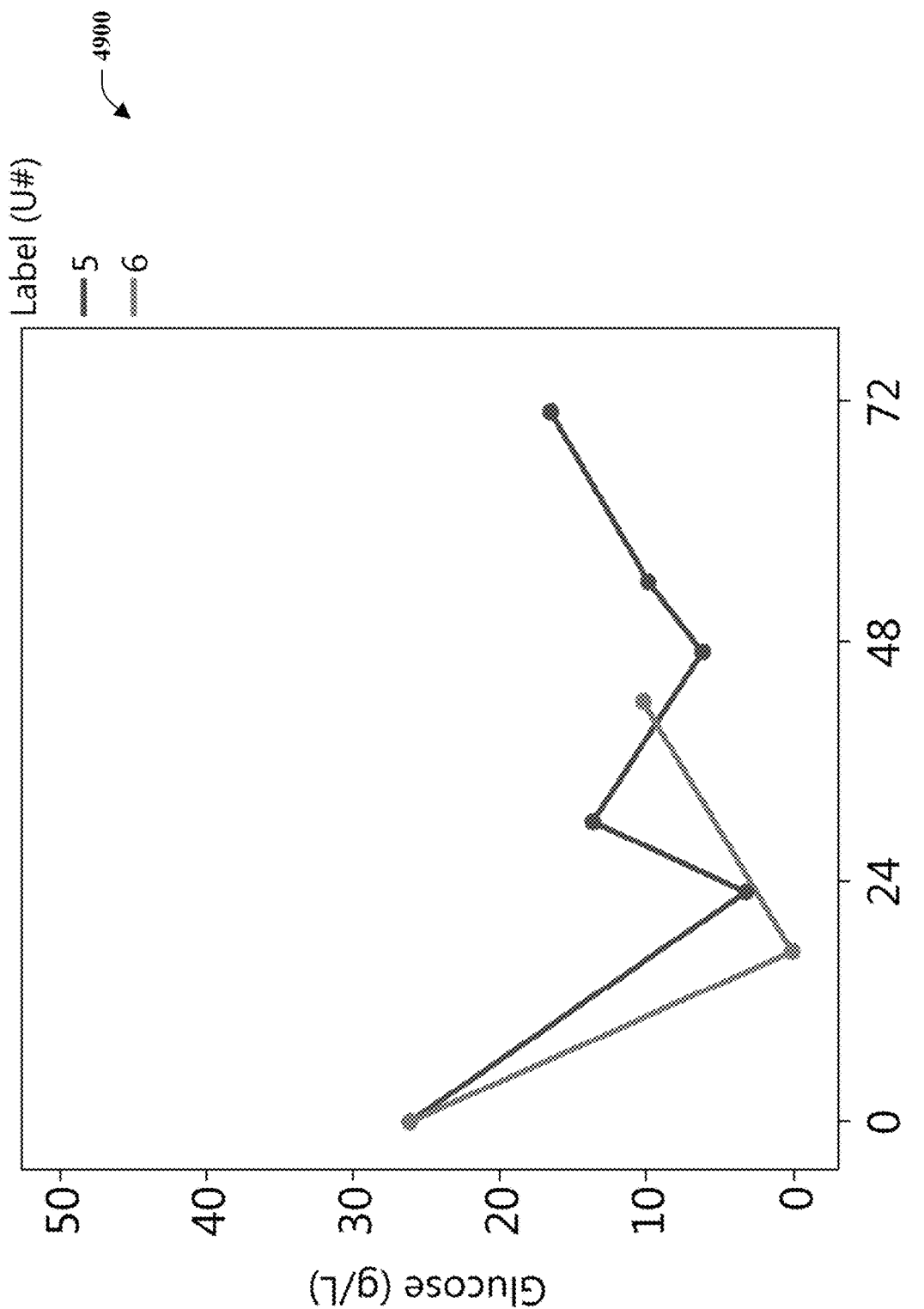

In this implementation, the pilot (1000 L) fermenter may achieve 80 g/L cell dry weight after 72 hrs of fermentation, as illustrated in the example results 4500 of FIG. 45. These results 4500 illustrate cell dry weight 4502 and residual glucose 4504 of *A. acetophilum* HS399 in a 1000 L pilot fermenter. In this implementation, productivities of over 30 g/L per day can be obtained, as illustrated in the results 4600 of FIG. 46, which illustrates the cumulative productivity of *A. acetophilum* HS399 in a 1000 L pilot fermenter.

Example 15

In some implementations, the performance of the reactor may be lower than its 10 L predecessor. This may be due to less than desired control of the cultivation parameters, as illustrated by the results in FIGS. 47A, 47B, 47C, 47D, which illustrate data resulting from substantially continuous monitoring (a.k.a. online data) of *A. acetophilum* HS399 in a 1,000 L pilot fermenter. Further, these results indicate that an oil containing 45% OCFAs could be industrially produced at scale using *Aurantiochytrium* sp. as shown in Table 24 in FIG. 48 using the techniques described herein. That is, for example, data generated by one or more sensors at the reactor or fermenter, such as pH sensor, dissolved oxygen sensor, off-gassing sensor, and others, can be continuously monitored (e.g., or periodically monitored, and automatically or manually recorded). In some implementations, the data may be automatically recorded, and can be communicatively transmitted to a remote location, for example. In this way, the data can be collected, as illustrated in the examples of FIGS. 47A-D and 50 (below).

Figure 50:
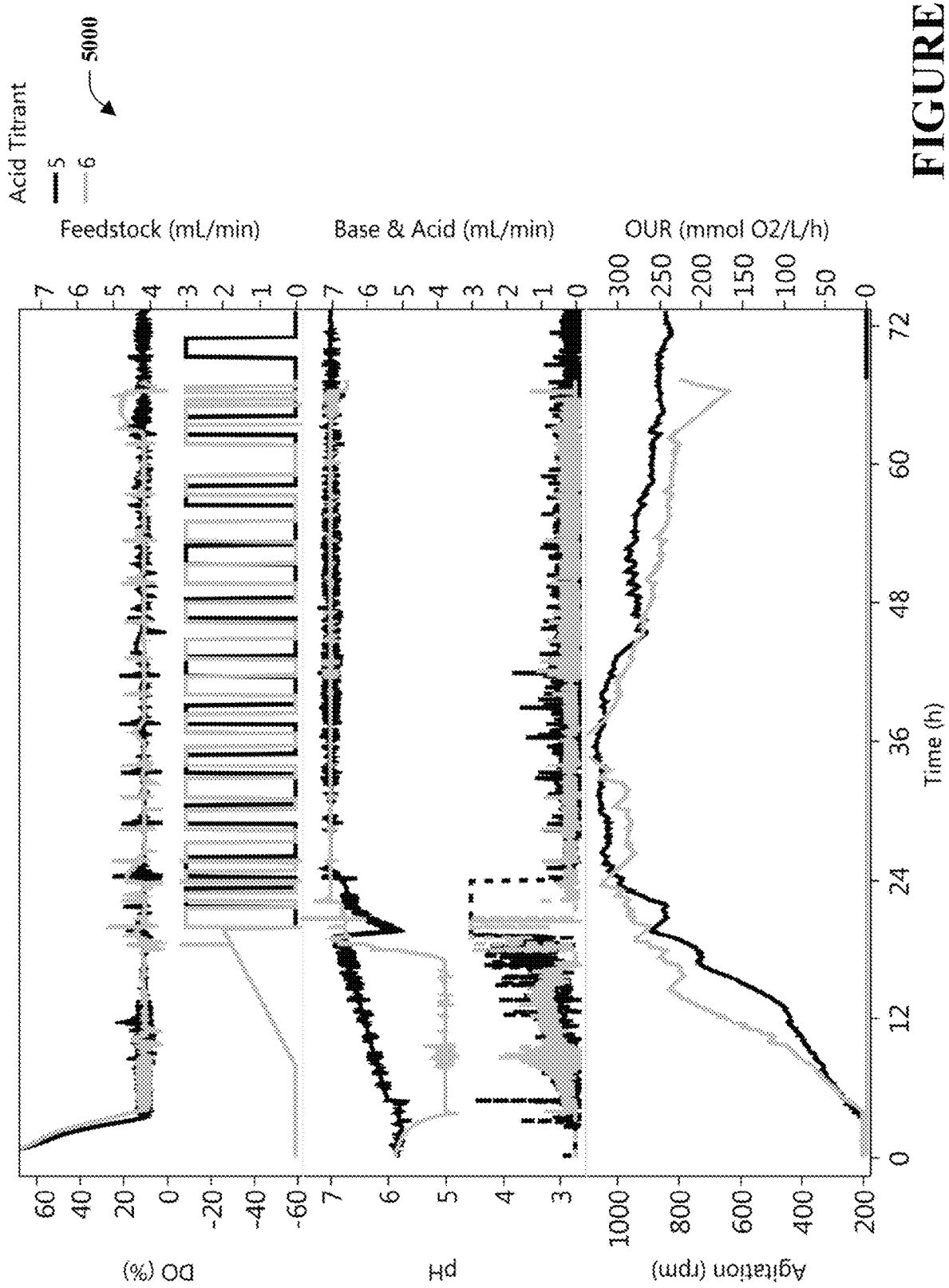
FIG. 50 is a graphical representation of online data readings of *A. acetophilum* HS399 double pH-auxostat cultures.

FIGS. 49A, 49B, 49C, 49D are graphical representations of example results 4900 illustrating *A. acetophilum* HS399 growth in a 10 L BIOFLOW-320 fermenter using double pH-auxostat cultures for the production of odd chain fatty acids, growth productivity and lipid accumulation (n=2). Further, FIG. 50 is a graphical representation of example results 5000 illustrating continuous monitoring of *A. acetophilum* HS399 double pH-auxostat cultures to produce odd chain fatty acids, DO2, glucose fed, pH, titrant addition and agitation (n=2).

Example 16—Anaplerotic Oils & Type 2 Diabetes

In one aspect, epidemiological data shows that odd chain fatty acids (OCFAs) in blood plasma inversely correlate with diabetes type 2 (Forouhi et al. (2014): Lancet Diabetes Endocrinol, 2(10), 810-818.; Santaren et al. (2014). Am. J. Clin. Nutr., 100(1), 1532-1540). In one implementation, *A. acetophilum* HS399 can be used to evaluate if OCFAs have an impact in glucose metabolisms.

Figure 51:
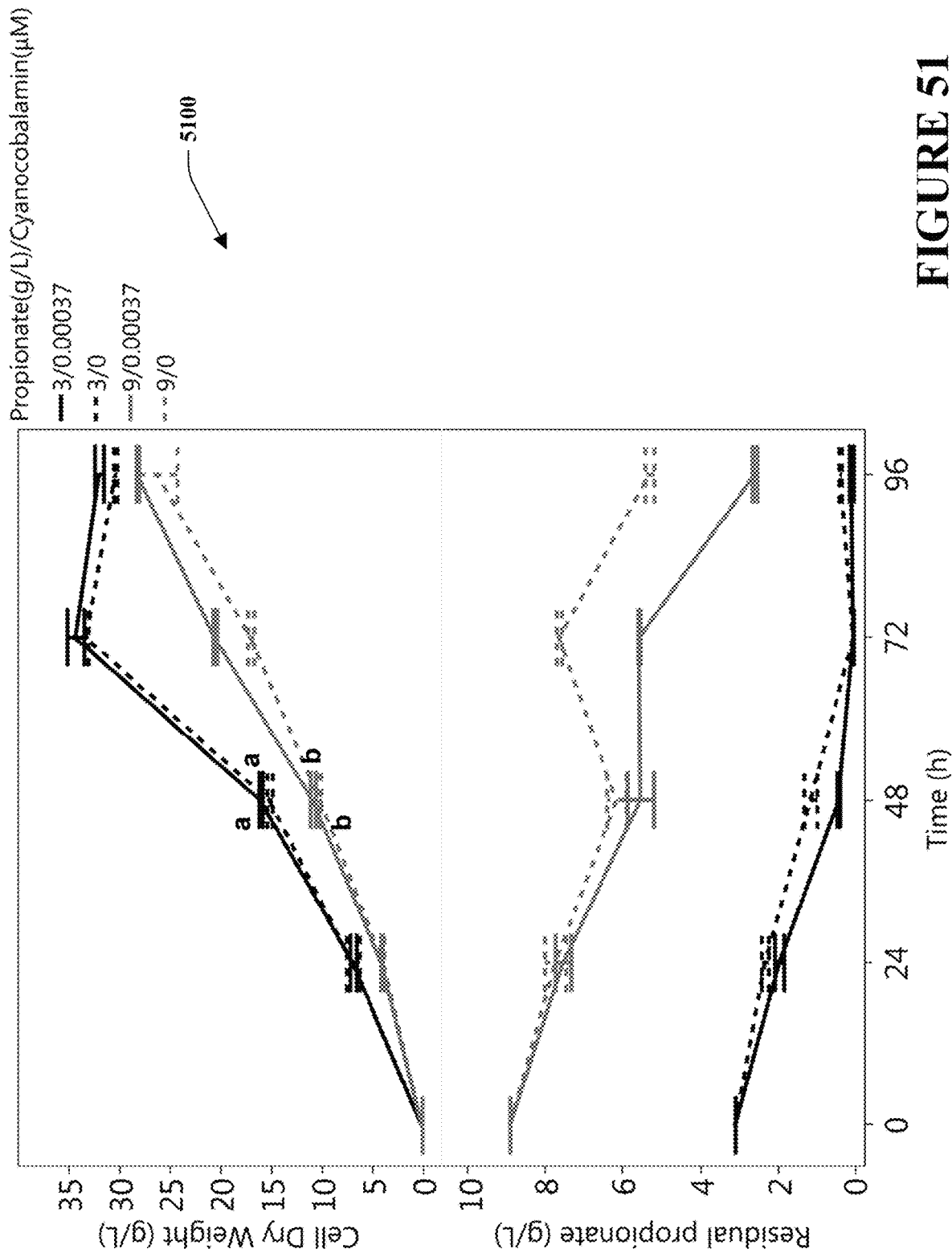
FIG. 51 is a graphical representation of an example result illustrating growth and residual propionate in *A. acetophilum* HS399 cultures that are subject to propionic anaplerosis triggered by cyanocobalamin.
Figure 52:
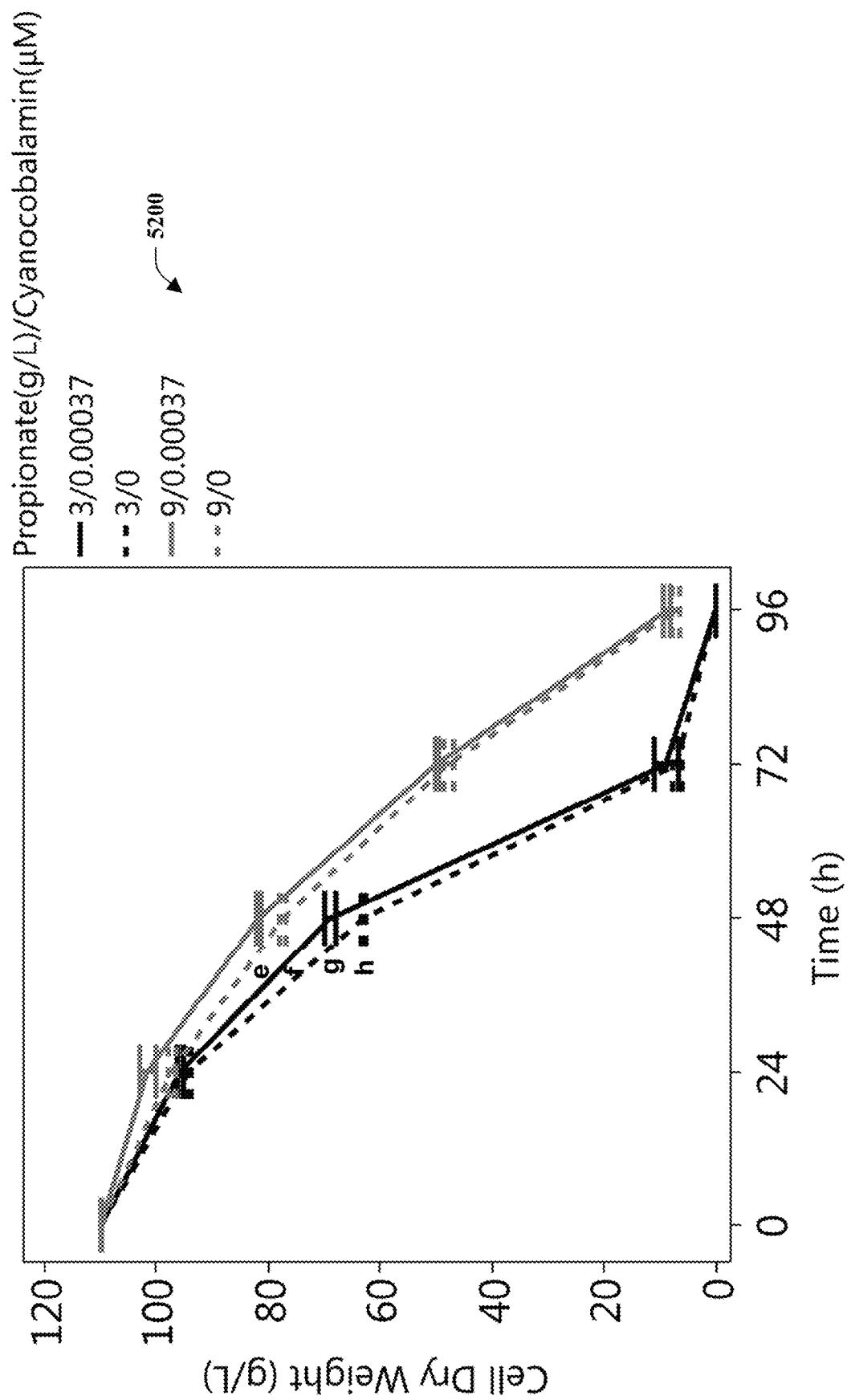
FIG. 52 is a graphical representation of residual glucose in *A. acetophilum* HS399 cultures subject to propionic anaplerosis triggered by cyanocobalamin.

FIG. 51 is a graphical representation of example results 5100 illustrating growth and residual propionate in *A. acetophilum* HS399 cultures that are subject to propionic anaplerosis triggered by cyanocobalamin. In FIG. 51, the different letters (a, b) in respective time points indicate statistically significant differences according to this implementation (p<0.05). FIG. 52 is a graphical representation of example results 5200 illustrating residual glucose in *A. acetophilum* HS399 cultures subject to propionic anaplerosis triggered by cyanocobalamin. In FIG. 52, the different letters (e, f, g, h) in each time point indicate statistically significant differences according to a t-student test (p<0.05).

In this implementation, a culture can be fed 3 and 9 g/L of odd numbered propionic acid that is a product of the oxidation of longer chain fatty acids C15:0 and C17:0 in the presence or absence of cyanocobalamin (0 vs 0.37 μM) in shake flask cultures. As described above, OCFAs anaplerosis can merely take place in the presence of cyanocobalamin. In this implementation, the cell dry weight and residual propionate can be monitored, and residual glucose in the media can be analyzed. As an example, while the growth in the first 48 hrs may not be impacted by the cyanocobalamin, as illustrated by the results 5100 of FIG. 51, the residual glucose data indicates that glucose uptake rate may be significantly (P<0.01 t-student) lower in the cyanocobalamin-anaplerotic treatment, as illustrated in the results 5200 of FIG. 52. For example, these results indicate a link between OCFAs anaplerosis and glucose metabolism, in support of a protective role of odd chain fatty acids (OCFAs) against diabetes type 2.

Example 17—OCFAs Promotors Alternative to Propionic Acid

In another aspect, alternative promoters for OCFA production may be utilized. Several implementations for use of alternative promoters are described below and shown in Table 25 in FIG. 54.

In one implementation, alternative promoters to propionic acid for production of OCFA may be implemented. According to techniques described above, *A. acetophilum* HS399 can accumulate OCFA in presence of propionic acid. Further, it may be beneficial to find alternative promotors to produce OCFA that are less toxic to the model organisms or that are simpler. In this implementation, pentanoate, heptanoate, yeast extract, proteose peptone, methionine, valine and isoleucine are evaluated for their capacity to induce the production of OCFAs. Erlenmeyer flasks can be used and *A. acetophilum* HS399 can be cultured following the protocols described herein.

Figure 53:
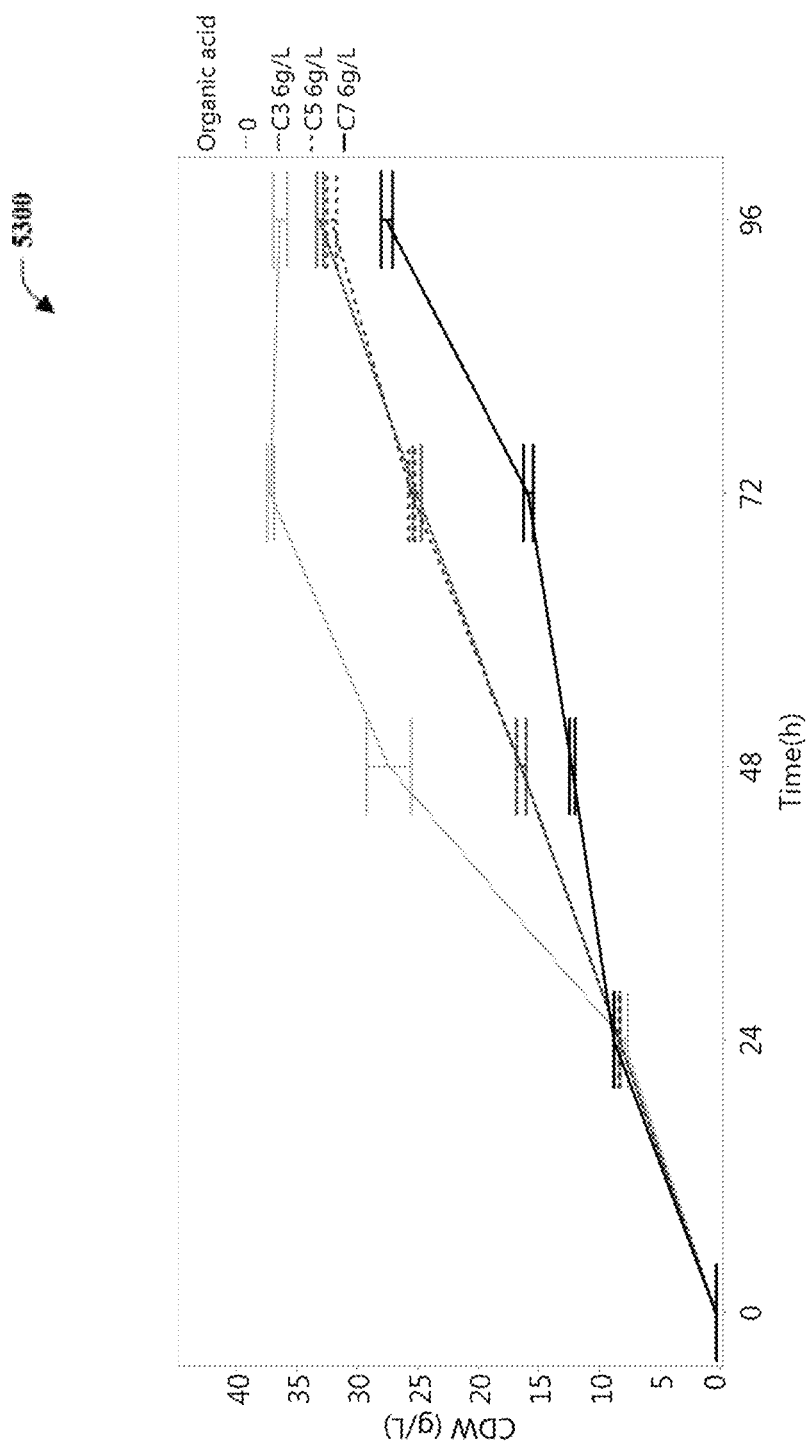
FIG. 53 is a graphical representation showing growth inhibition of *A. acetophilum* HS399 by short chain fatty acids propionic acid (C3:0), pentanoic acid (C5:0) and heptanoic acid (C7:0)

In this implementation, respective flasks can be supplemented with different concentrations of the proposed promoters and the resulting biomass harvested and analyzed for total lipid and fatty acid analyses. In this implementation, valine and isoleucine are identified as a nitrogen and OCFAs source. Yeast extract, but not proteose peptone, is identified as a precursor of OCFAs, presumably because proteose peptone has a smaller proportion of the amino acids present in a free form than yeast extract. As illustrated in FIG. 53, it pentanoate and heptanoate may be able to promote the production of OCFAs, but the toxicity of heptanoic is higher than that of propionic acid (see result 5300).

Example 18—Anaplerotic Oils & Health Benefits

In one aspect, epidemiological data shows that odd chain fatty acids (OCFAs) in blood plasma inversely correlate with diabetes type 2 (Forouhi et al. (2014): Lancet Diabetes Endocrinol, 2(10), 810-818.; Santaren et al. (2014). Am. J. Clin. Nutr., 100(1), 1532-1540). In one implementation, *A. acetophilum* HS399 can be used to evaluate if OCFAs have an impact in glucose metabolisms.

In one aspect, because anaplerotic substrates can be used to restore energy balance in mitochondria, there is a wide range of pathologies to which odd chain fatty acids have shown benefits. Namely, odd chain fatty acids have been experimentally used to treat the following conditions:
Genetic Metabolic disorders
  Glut1 deficiency
  Fatty acid oxidation disorder (FAOD)
  Pyruvate carboxylase deficiency (Mochel et al., 2005)
  Carnitine Palmitoyltransferase II deficiency (Roe et al., 2008)
  Rett syndrome (RTT)
  Phenylketonuria (Roe & Mochel, 2006)
  Adult Polyglucosan Body Disease (APBD) (Roe et al., 2010)
  long-chain fat oxidation disorders (Roe et al., 2002)
Neurodegenerative diseases:
  Epilepsy (Borges and Sonnewald, 2012)
  Alzheimer's disease
  Parkinson
  Autism spectrum disorder (ASD)
Metabolic syndrome diseases
  Diabetes type 2
  Obesity
  Cardiovascular disease Additionally, there is some indication that odd chain fatty acids can help in building muscle and improving athlete metabolism. For example, vigorous physical effort might result in depletion of glucose and glycogen, in which case the main anaplerotic substrate comes from the protein. Based on this process, one may hypothesize that odd chain fatty acids might spare the use of protein catabolism as anaplerotic substrate. Obesity and fat burn conditions may also benefit from use of odd chain fatty acids found in anaplerotic oils. For example, during periods of fat burn, odd chain fatty acid might restore the energy imbalance and help catalyze the energy generation from lipids. For instance, patients recovering from a surgical procedure might benefit from the OCFA anaplerosis.

Table 26, in FIG. 55, illustrates various, commonly available natural vegetable oils. Further, the table shows the concentrations of various fatty acids available in the respective vegetable oils. As illustrated, the OCFA, particularly C15 and C17, are not found, or are found in trace amounts in natural vegetable oils.

Table 27 below compares the features of the two types of concentrated anaplerotic oils, synthetic anaplerotic oils (e.g., tripentanoin) against naturally produced anaplerotic oils from microorganisms. Synthetic oils such as triheptanoin and tripentanoin typically have high concentrations of OCFAs. However, anaplerotic oil produced from microalgae, as described herein, possesses several advantages over the synthetic triheptanoin and tripentanoin. As illustrated, the natural anaplerotic oil produced by algae includes OCFA that are naturally present in our diet (C15:0 and C17:0), while triheptanoin synthetically synthesis OCFA of C5:0 and C7:0, which are not found in naturally occurring food sources.

Further, in this example, the anaplerotic oil produced by algae can contain a substantial amount of DHA, which is a valuable nutraceutical. For example, DHA (docosahexaenoic acid) is a fatty acid that is commonly found in the meat of cold-water fish (e.g., tuna, salmon, cod, etc.). DHA has been found to improve early brain development in infants and may improve the vision and cognitive function development. Further, DHA has been used for treating type 2 diabetes, coronary artery disease (CAD), dementia, depression, and attention deficit-hyperactivity disorder (ADHD), as well as improving vision and cognitive function in adults. Additionally, DHA can be converted into eicosapentaenoic acid (EPA) in the body, which is used in the prevention and reversal of heart disease, stabilizing heart rhythm, asthma, cancer, painful menstrual periods, hay fever, lung diseases, systemic lupus erythematosus (SLE), and certain kidney diseases. Both EPA and DHA have been used in combination to treat high cholesterol, high blood pressure, psoriasis, Raynaud's syndrome, rheumatoid arthritis, bipolar disorder, certain inflammations of the digestive system (ulcerative colitis), and to prevent migraine headaches in teenagers.

TABLE 27

Comparison of synthetic anaplerotic oils with naturally produced anaplerotic oils from microorganisms

| | ANAPLEROTIC OILS | | |
|---|---|---|---|
| | Tripentanoin | Anaplerotic | Dairy Fat |
| Process | Chemical Synthesis | Biosynthesis | Biosynthesis |
| Type of OCFA | Artificial | Natural-Dietary | Natural-Dietary |
| | C5:0; C 7:0 | C15:0; C17:0 | C15:0; C17:0 |
| OCFA (% TFA) | 100 | 60 | 1.5 |
| DHA (% TFA) | 0 | 25 | <1 |

Synthetic Production of Odd Chain Fatty Acid and their Triacylglycerides

In some embodiments, odd chain fatty acids OCFAs and triacylglycerides containing OCFAs may be produced synthetically. As an example, the synthesis of saturated C15 or C17 fatty acids can be accomplished using different chemical reactions/strategies, some of which are summarized in Diagram 1 (A-I). The example methods described below can be used for synthesizing fatty acids esters as well by adopting appropriate protection/de-protection strategies. The fatty acids or esters can then be used to synthesize triglycerides, the reaction can be catalyzed by base or preferably enzymatically to obtain OCFA enriched triglycerides. The synthetic scheme for triglyceride synthesis is described in Diagrams 1A-1I below.

A) Kumada Cross-Coupling

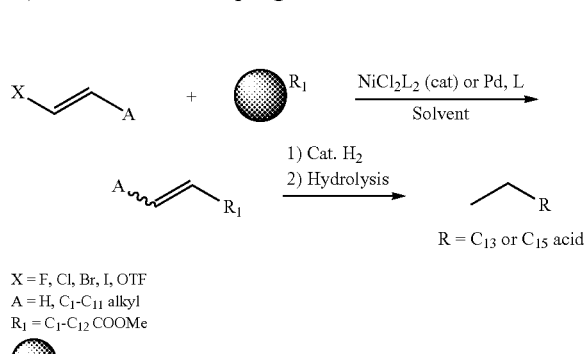

X = F, Cl, Br, I, OTF
A = H, $C_1$-$C_{11}$ alkyl
$R_1$ = $C_1$-$C_{12}$ COOMe

⬤ = MgX; X = Br, I or = Li $L_2$ = dppp, dppe, dppb
L = $PPh_3$

B) Negishi Cross-Coupling

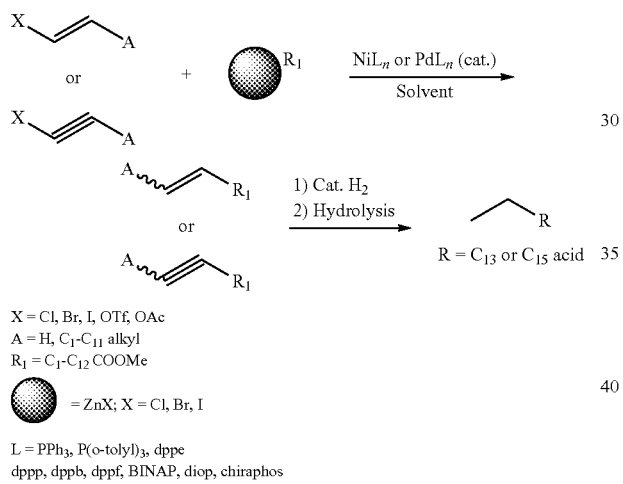

X = Cl, Br, I, OTf, OAc
A = H, $C_1$-$C_{11}$ alkyl
$R_1$ = $C_1$-$C_{12}$ COOMe ⬤ = ZnX; X = Cl, Br, I L = $PPh_3$, P(o-tolyl)$_3$, dppe
dppp, dppb, dppf, BINAP, diop, chiraphos C) Sonogashira Cross-Coupling

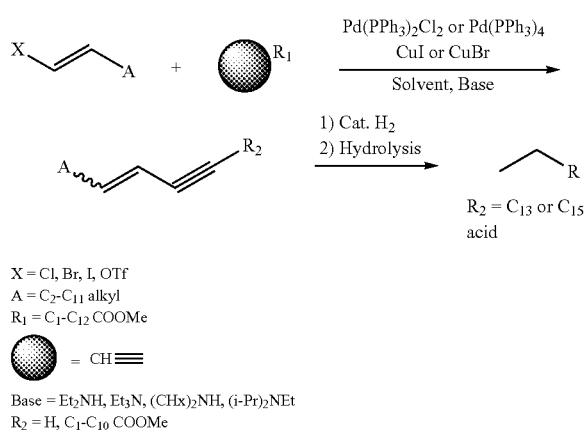

X = Cl, Br, I, OTf
A = $C_2$-$C_{11}$ alkyl
$R_1$ = $C_1$-$C_{12}$ COOMe

⬤ = CH≡

Base = $Et_2NH$, $Et_3N$, $(CHx)_2NH$, $(i-Pr)_2NEt$
$R_2$ = H, $C_1$-$C_{10}$ COOMe D) Stille Cross-Coupling

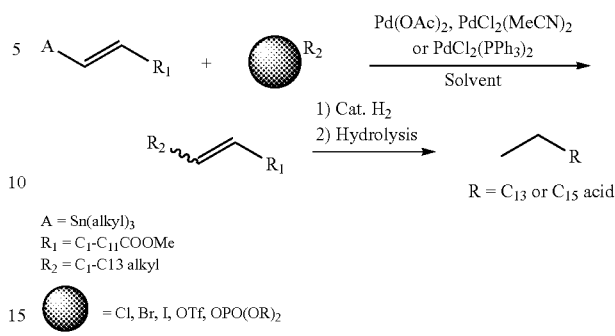

A = Sn(alkyl)$_3$
$R_1$ = $C_1$-$C_{11}$COOMe
$R_2$ = $C_1$-C13 alkyl

⬤ = Cl, Br, I, OTf, OPO(OR)$_2$

E) Suzuki Cross-Coupling

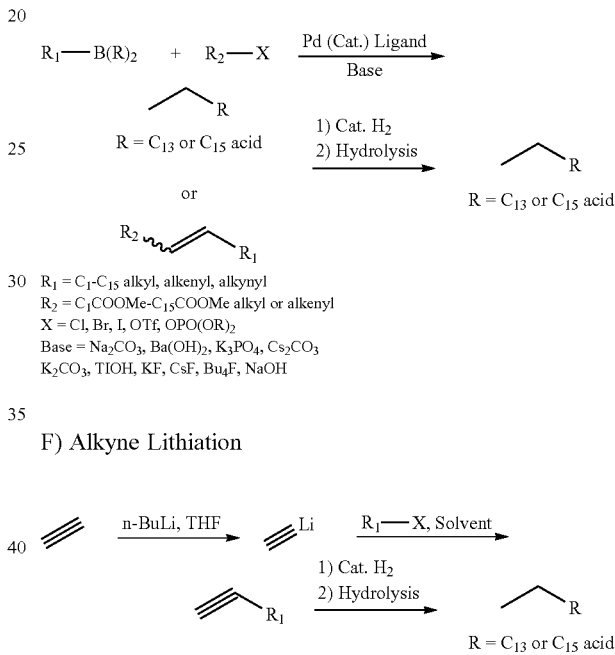

$R_1$ = $C_1$-$C_{15}$ alkyl, alkenyl, alkynyl
$R_2$ = $C_1$COOMe-$C_{15}$COOMe alkyl or alkenyl
X = Cl, Br, I, OTf, OPO(OR)$_2$
Base = $Na_2CO_3$, $Ba(OH)_2$, $K_3PO_4$, $Cs_2CO_3$
$K_2CO_3$, TlOH, KF, CsF, $Bu_4F$, NaOH F) Alkyne Lithiation

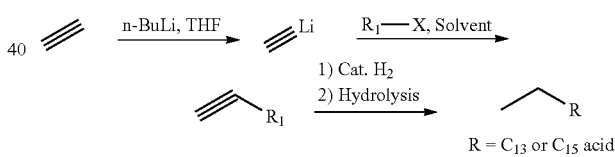

$R_1$ = $C_{13}$-$C_{15}$ COOMe alkyl, alkenyl or alkynyl
X = Cl, Br, I, OTf, OMs, OTs G) Jones Oxidation

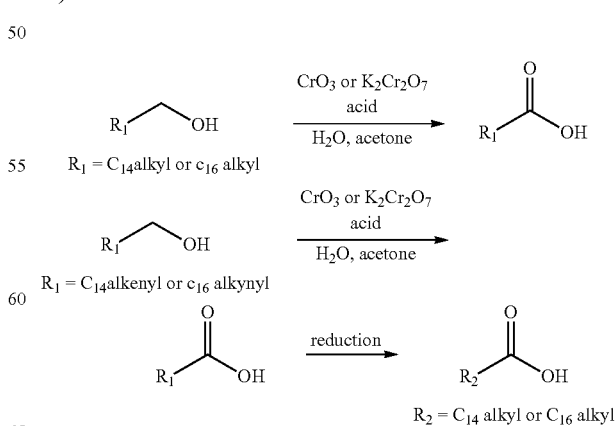

$R_1$ = $C_{14}$alkyl or $c_{16}$ alkyl $R_1$ = $C_{14}$alkenyl or $c_{16}$ alkynyl $R_2$ = $C_{14}$ alkyl or $C_{16}$ alkyl H) Arndt-Eistert Homologation

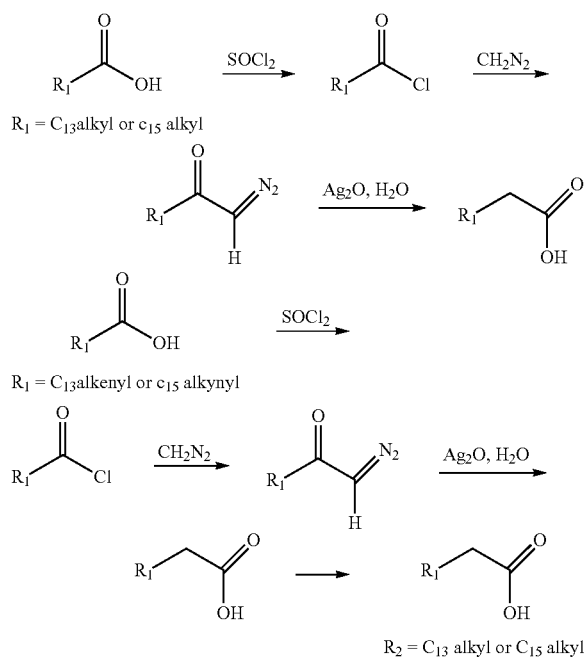

I) Triglyceride Synthesis (Chemical or Enzymatic Synthesis)

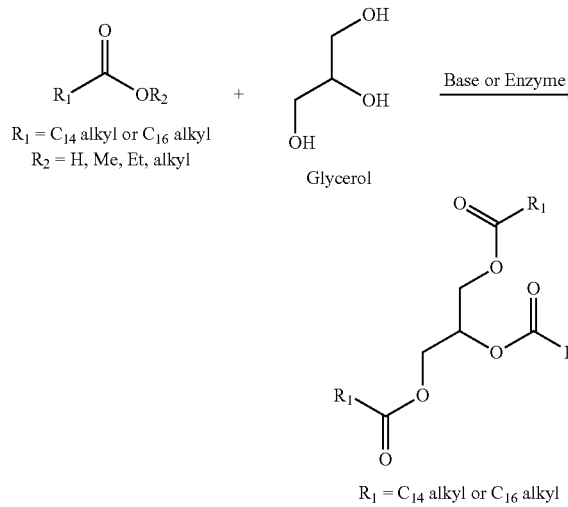

Diagrams 1A-1I Examples of Chemical Synthesis of Odd Chain Fatty Acid and their Cleavage in a Triacylglyceride.

In another embodiment, a representative synthesis of odd chain fatty acid triglycerides from commercially available starting materials is described in Diagram 2, below. In this embodiment, octyl bromide is first converted into corresponding boronate ester, which is then subjected to Suzuki coupling with 7-bromoheptanoic acid methyl ester to yield C15 methyl ester. The methyl esters are then converted to triglycerides by treating with glycerol. The fatty acids/esters can be synthesized using other methods described in Diagram 2 using other commercially available starting materials.

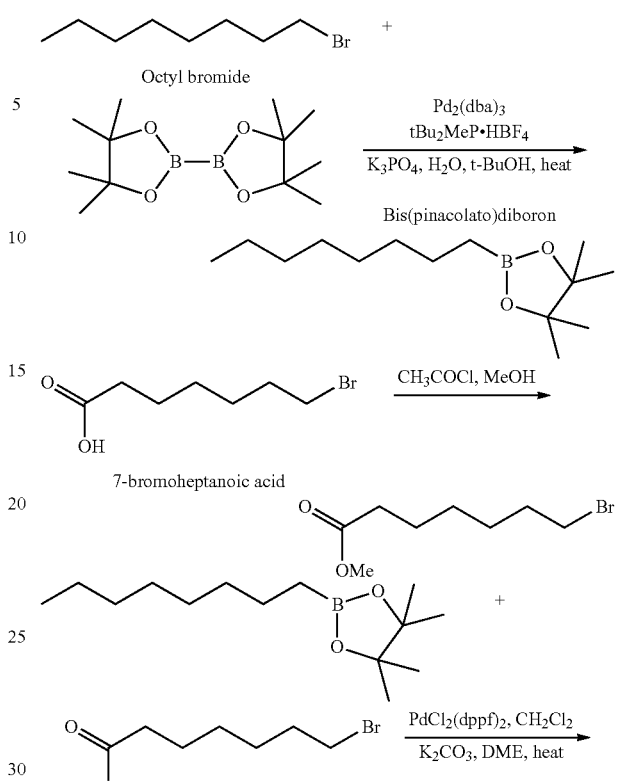

Diagram 2 Example Reactions for the Synthetic Production of Odd Chain Fatty Acid Triglyceride from Commercially Available Starting Materials.

Human Use of Anaplerotic Oils

The widespread use of pentadecanoic (C15:0) and heptadecanoic acid (C17:0) levels in human blood plasma as biomarkers for low incidence of diabetes type 2 and cardiovascular disease challenges the prevailing dietary guidelines around saturated fatty acid intake. Recently, the prospective cohort study "PURE" concluded that dairy consumption, responsible for 45% of the total saturated fat intake, was associated with lower risks of cardiovascular disease and mortality, which echoes the long debate around the French Paradox and the fact that dairy is also the main dietary source of odd-chain fatty acids (OCFAs). Milk fat has C15:0 and C17:0 present only trace amounts (<2% total fatty acids, TFA) compared to the prevalent even-chain saturated fatty acids (~70% TFA).

As described herein, natural oils that contains saturated fatty acids that are predominantly odd-chain (odd-chain fatty acids (OCFA)) may be used as a supplement to typical dietary intake of OCFA. In one implementation, as described herein, *Aurantiochytrium acetophilum* strain HS399 is capable of accumulating lipids of up to 85% of its weight, such as when grown according to the techniques described herein (e.g., such as heterotrophic conditions). *A. acetophilum* HS399 naturally produces palmitic acid (C16:0) (e.g., at 45 TFA) and docosahexaenoic acid (DHA, C22:6 n-3) (e.g., at 40% TFA). The techniques and systems described herein describe a modified cultivation process (e.g., fermentation) that can produce C15:0 (e.g., up to or greater than 40% of TFA), C16:0 (e.g., up to and greater than 15% of TFA), C17:0 (e.g., up to or greater than 8% of TFA) and up to or greater than 28% DHA of TFA.

As an example, the techniques described herein may have the capacity to produce, at industrial scale, a human nutritional oil that will help isolate the effect of dietary even-chain versus dietary odd-chain fatty acids. For example, in some embodiments, the natural oil containing high concentrations of OCFA, described herein, may produce OCFA of >49% TFA. Such a product can be used to expand use of anaplerotic oils as a food additive, and research into anaplerotic metabolism and biomarkers in epidemiology, and ultimately become an important nutritional supplement.

As described above, most OCFA is introduced into the human diet through consumption of dairy-related products. Dairy-related products also have phytanic acid, as do some ruminant animal fats, and certain fish. Phytanic acid in consumed foods can provide a type of marker for the source of the OCFA when they are found together in a product, for example, from dairy. In one implementation, a consumable may be produced that comprises higher levels of OCFA, without the presence of Phytanic acid. That is, for example, the techniques described herein can produce higher levels of OCFA without producing phytanic acid. As such, in this example, the resulting biomass and/or oils can be used in food and will comprise higher levels of OCFA without phytanic acid.

In one aspect, saturated fat with a higher concentration of OCFA also has a higher melting point. In one implementation, those saturated fats with a melting point that is approximately 35 degrees Celsius or higher can contain a desired amount of OCFA, such as those that may be produced by the techniques described herein. In one implementation, those saturated fats with the elevated melting points (e.g., ≥35° C.) can be introduced into human food. In one implementation, one or more portion of biomass resulting from techniques described herein, comprising those saturated fats with the elevated melting points (e.g., ≥35° C.), may be used for human consumption. In this way, for example, using saturated fats with elevated melting points can result in consumption of elevated amounts of OCFA. As one example, those saturated fats with OCFA concentrations higher than ten percent will typically have a melting temperature greater than 35 degrees Celsius.

Example 19—Incorporating Anaplerotic Oil Rich in OCFA into Food

The average saturated fat (SFA) intake of a person based on a 2,500-calorie diet is about 25-28 g SFA/person day (See for example World Health Organization; see also for example US Department of Health; Otto et al., 2012). It is typically recommended that saturated fat intake should be less than 10% of the total energy intake. Id. In one aspect, consumption of about 26 g/person day of a microbial anaplerotic oil (MAO), such as an algal anaplerotic oil (AAO) described above, can contribute with approximately half of the average saturated fat intake (~14 g SFA/person day). That is, for example, the MAO derived from one or more techniques described herein may provide forty-five percent (e.g., or more) of the SFA per person day when consumed.

In one implementation, in this aspect, significant amounts of the dietary even chain saturated fat found in standard naturally occurring foods (e.g., all-natural beef, as opposed to plant-based beef substitute) can be replaced with odd chain saturated fat from the MAO, for example, without significantly changing the dietary habits of the consumer. For example, the inclusion levels of the MAO, comprising approximately 45% OCFAs, may depend on each product. However, generally, the dietary even chain saturated fat can be replaced with odd chain saturated fat. As an example, if a whole milk serving (244 g) typically has 4.6 g of saturated fat, a portion of the even-chain saturated fat can be replaced with the MAO, as follows: 4.6 g of saturated fat in milk/0.45 OCFA in the MAO=10.2 g of MAO can be used to replace the even-chain fat with the OCFA. That is, for example, 10.2 g of the MAO replaces the 4.6 g of saturated fat in the milk to have approximately the same amount of fatty acid present in the milk, except it would be OCFA instead of even-chain fatty acid.

In an implementation regarding standard naturally occurring foods, the MAO or AAO can be incorporated both as a direct food ingredient, as a nutritional supplement, and used in many different food products as a food additive, such as those belonging to the categories listed below, and others not listed. As one example, any food that comprises fatty acid may be appropriate for replacement of the even-chain fatty acid with the OCFA found in the MAO described herein. Further, the MAO described herein may be incorporated into foods as an additive or nutritional supplement to provide benefits associated with consumption of OCFA.

Dairy Products: Milk, cheese, cream, yogurt, butter, powder milk

Eggs and egg products

Spreads, sauces, dressings and condiments: mayonnaise, margarine, cheese spreads, salad dressings, nut spreads Meat products: Poultry, swine, cattle, lamb, lard, sausages, cured meat, jerky, Sports foods: energy bars, protein concentrates, protein supplements Snacks and crackers Produce: fruits and vegetables Drinks: sodas, juices, energy drinks etc.

Gelatins and puddings

Soups and broths

Frozen desserts

Seafood: fish, crustaceans, mollusks etc.

Plant based meat and seafood: tuna equivalent, burger equivalent etc.

Pasta & Rice: spaghetti, noodles etc.

Bakery: brad, tortillas, pita, naan, cakes, desserts

Breakfast foods: cookies, corn flakes, pop corns, oats, breakfast cereals, pastries and pie Chocolates containing food Culinary oils: cooking and dressing oil Soy-based products: tofu, soy sauce, miso etc.

Soft and hard candy

Food additives: Olive oil conserve

Canned foods

Frozen foods

Infant formulae

Analogs to the products listed above

In another implementation regarding plant-based foods, one may identify the amount of saturated OCFAs (e.g., tridecanoic, pentadecanoic, and heptadecanoic fatty acids) present in a standard food (e.g., ¼ pound of natural beef burger). One may then add an amount of MAO or AAO that contains the same amount of saturated OCFAs found in the standard food to a target corresponding plant-based food (e.g., ¼ pound plant-based burger). In this way, the plant-based substitute food (in this example, the plant-based burger) now contains the same amount of OCFAs that would be contained in its standard food counterpart (in this example, the natural beef burger) and thereby the plant-based substitute food becomes the plant-based equivalent to its counterpart standard food. It should be clearly understood that substantial benefit may also be derived from adding an amount of MAO or AAO to the target plant-based substitute food so that the amount of saturated OCFAs in the target plant-based substitute food exceeds that contained in its standard food counterpart. It should also be clearly understood that substantial benefit may also be derived from adding an amount of MAO or AAO to the target plant-based substitute food so that the amount of saturated OCFAs in the target plant-based substitute food is lower than that contained it its standard food counterpart.

In one implementation regarding plant-based foods, one may identify the amount of saturated fat present in a standard food (e.g., cow milk-based butter). One may then prepare a plant-based substitute food (e.g. soy based butter) and add an amount of MAO or AAO that contains an amount of saturated OCFAs to the plant-based food (e.g. soy based butter), wherein the plant-based substitute food (in this example, the plant-based butter) now contains a lower amount of saturated OCFAs than that contained in its standard food counterpart (in this example, the cow milk based butter). Thus, the plant-based butter substitute becomes a healthier alternative to its counterpart standard butter.

In another implementation, one may add an amount of MAO or AAO to a plant-based food that does not naturally contain any OCFAs. For example, plant-based dairy products may contain zero OCFAs. One may then add an amount of MAO or AAO to the plant-based food (in this example, the plant-based dairy product) so that it now contains saturated OCFAs.

The invention disclosed herein may be applied in several ways. In one embodiment, the saturated fat in a standard naturally occurring food may be removed by processes such as separation with a solvent, separation via filtration, molecular distillation, or any other means capable of removing saturated fat; then, the saturated OCFAs may be added to the target food product via the inclusion of the MAO or AAO. In another embodiment, the saturated fat in a standard naturally occurring food may remain unchanged and then the saturated OCFAs may be added to the target food product via the inclusion of the MAO or AAO. And in another embodiment, one may determine a targeted daily amount of OCFAs to include in the target food and may then add that targeted daily amount of saturated OCFAs to the target food (this would apply when the target food initially contains zero OCFAs); or, alternatively, when the target food does contain some saturated OCFAs (but contains less OCFAs than the targeted daily amount of OCFAs) one may add an amount of saturated OCFAs via the inclusion of the MAO or AAO so that the total amount of OCFAs (naturally occurring OCFAs+OCFAs added via AAO/MAO) matches the targeted daily amount of OCFAs.

A demonstration was performed to illustrate the addition of Algal Anaplerotic Oil (AAO) to different groups of food suitable for animal (both human and non-human) consumption. Samples of food were weighted and then freeze dried for 48 h. Consequently, samples were weighted on a dry basis and spiked with Algal Anaplerotic Oil as indicated in Tables 28-30 below. Total lipids were analyzed using the Folch method (AOAC 996.06) and the FAMES were analyzed by gas chromatography using nonadecanoic (C19:0) acid as an internal standard. The AAO was added to supply 20-30% of the highest inclusion levels for the AAO targeted amount of 6.0 g/day in a serving size of each of the food samples. In Tables 28-30, the OCFA (% TFA) refers to the total amount of saturated C13:0, C15:0 and C17:0 fatty acids in the particular food item.

Table 28 below shows an example of the fatty acid composition of various types of milk: whole fat milk, low fat milk, almond milk, and soy milk. Specifically, as shown in the examples, OCFA comprised about 24% of the TFA in low fat milk; OCFA comprised about 26.3% TFA in almond milk; and OCFA comprised about 10% TFA in soy milk. In some embodiments, after addition of microbial anaplerotic oil to milk, the OCFA may comprise about 1-30% of TFA of the milk. In other embodiments, the OCFA may comprise about 2-5% of the TFA of the milk. In other embodiments, the OCFA may comprise about 5-10% of the TFA of the milk. In other embodiments, the OCFA may comprise about 10-15% of the TFA of the milk. In other embodiments, the OCFA may comprise about 15-20% of the TFA of the milk. In other embodiments, the OCFA may comprise about 20-25% of the TFA of the milk. In other embodiments, the OCFA may comprise about 25-30% of the TFA of the milk. It should be clearly understood that substantial benefit may still be derived from higher or lower rates of inclusion of OCFA in the milk.

In this example, it should be clearly understood that the milk products may be standard natural animal milk (from cows, goats, etc.) or plant-based substitute milk (e.g., soy or almond milk). Where the milk is a plant-based substitute milk, an amount of AAO or MAO may be added in order to match or exceed the amount of saturated OCFAs present in the standard naturally occurring milk counterpart.

TABLE 28

| Fatty Acid Composition of Milk before and After Algal Anaplerotic Oil Addition | | | | | | | |
|---|---|---|---|---|---|---|---|
| | Whole Fat Milk | Low Fat Milk Control | Low Fat Milk + AAO | Almond Control | Almond + AAO | Soy Control | Soy + AAO |
| TFA (% DW) | 24.1 | 6.0 | 10.7 | 9.7 | 18.5 | 22.6 | 27.3 |
| C10:0 | 1.7 | 1.1 | 0.7 | — | — | — | — |
| C12:0 | 2.5 | 2.1 | 1.3 | — | — | — | — |
| C13:0 | — | — | 0.6 | — | 0.7 | — | 0.2 |

TABLE 28-continued

Fatty Acid Composition of Milk before and After Algal Anaplerotic Oil Addition

|  | Whole Fat Milk | Low Fat Milk Control | Low Fat Milk + AAO | Almond Control | Almond + AAO | Soy Control | Soy + AAO |
|---|---|---|---|---|---|---|---|
| C14:0 | 9.6 | 9.1 | 6.1 | — | 0.5 | — | 0.2 |
| C14:1 | 0.7 | 0.7 | 0.4 | — | — | — | — |
| C15:0 | 1.0 | 1.0 | 18.7 | — | 20.7 | 0.1 | 7.8 |
| C16:0 | 30.2 | 31.1 | 22.4 | 20.8 | 15.1 | 10.6 | 10.2 |
| C16:1 | 1.6 | 1.7 | 1.2 | 1.7 | 1.1 | — | 0.1 |
| C17:0 | 0.7 | 0.7 | 4.6 | — | 4.9 | 0.2 | 2.0 |
| C17:1 | — | — | — | 0.4 | 0.2 | — | — |
| C18:0 | 14.8 | 15.2 | 9.5 | 4.7 | 2.7 | 4.1 | 3.5 |
| C18:1n9 | 31.1 | 31.0 | 19.5 | — | — | 21.6 | 18.0 |
| C18:2n6 | 4.5 | 4.2 | 2.8 | 72.3 | 40.2 | 54.1 | 45.1 |
| C18:3n3 | 0.8 | 0.7 | 0.5 | — | — | 8.4 | 7.0 |
| C18:3n6 | — | — | — | — | — | — | — |
| C19:0 IS | 6.9 | 25.8 | 14.3 | 15.4 | 7.9 | 7.1 | 6.2 |
| C20:0 | 0.2 | — | — | — | — | 0.3 | 0.3 |
| C20:1n9 | 0.6 | 1.4 | — | — | — | 0.2 | 0.2 |
| C20:2 | — | — | — | — | — | — | — |
| C20:3n3 | — | — | — | — | — | — | — |
| C20:3n6 | — | — | — | — | — | — | — |
| C20:4n6 | — | — | — | — | — | — | — |
| C20:5n3 EPA | — | — | — | — | 0.3 | 0.3 | 0.4 |
| C22:1n9 | — | — | — | — | — | — | — |
| C22:5n6 DPA | — | — | 1.7 | — | 2.0 | — | 0.8 |
| C22:6n3 DHA | — | — | 10.0 | — | 11.5 | — | 4.3 |
| C24:1 & C22:5n3 | — | — | — | — | — | — | — |
| OCFA (% TFA) | 1.7 | 1.7 | 24.0 | — | 26.3 | 0.3 | 10.0 |
| Serving size (g) | 240 | 240 | 240 | 240 | 240 | 240 | 240 |
| AAO per serving (g) | — | — | 2.0 | — | 0.9 | — | 1.7 |
| Fat Content (% WW) | 3.8 | 1.0 | 1.8 | 1.0 | 1.4 | 1.9 | 2.6 |

Table 29 below shows an example of the fatty acid composition of varying types of dairy-containing products such as yogurt, ice cream, and chocolate. Specifically, as shown in the examples, OCFA comprised about 28.2% of the TFA in yogurt; OCFA comprised about 13.1% of the TFA in ice cream; and OCFA comprised about 5.8% of the TFA in chocolate. In some embodiments, after addition of microbial anaplerotic oil to dairy-containing products, the OCFA may comprise about 5-30% of TFA of the dairy-containing product. In other embodiments, the OCFA may comprise about 5-10% of the TFA of the dairy-containing product. In other embodiments, the OCFA may comprise about 10-15% of the TFA of the dairy-containing product. In other embodiments, the OCFA may comprise about 15-20% of the TFA of the dairy-containing product. In other embodiments, the OCFA may comprise about 20-25% of the TFA of the dairy-containing product. In other embodiments, the OCFA may comprise about 25-30% of the TFA of the dairy-containing product. It should be clearly understood that substantial benefit may still be derived from higher or lower rates of inclusion of OCFA in the dairy-containing products.

In this example, it should be clearly understood that the dairy-containing products may be standard natural dairy-containing products (i.e., containing milk from cows, goats, etc.) or plant-based substitute dairy-containing products (i.e., containing soy milk or almond milk). Where the dairy-containing product is a plant-based substitute dairy-containing product, an amount of AAO or MAO may be added in order to match or exceed the amount of saturated OCFAs present in the standard naturally occurring dairy-containing counterpart.

It should be clearly understood that "dairy-containing products" may also include butter. For example, by starting with a plant-based milk (e.g., soy, almond, etc.) and adding an amount of MAO or AAO to it, a plant-based butter product may be created wherein the amount of saturated OCFAs in the plant-based butter substitute is lower that contained in its natural dairy-containing butter counterpart wherein the natural dairy-containing butter counterpart was made with milk coming from an animal such as a cow or goat.

It should also be clearly understood that further substantial benefit may be derived from adding MAO or AAO to non-dairy containing products, such as noodles, wherein the food contains vegetable oil, canola oil, or any other oil suitable for food production. As with the other examples contained herein, an amount of MAO or AAO may be added to the non-dairy containing product, such as noodles, in order to add a desired amount of saturated OCFAs thereto.

TABLE 29

Fatty Acid Composition of Dairy-Containing Products before and After Algal Anaplerotic Oil Addition

|  | Yogurt Control | Yogurt + AAO | Ice Cream Control | Ice Cream + AAO | Chocolate Control | Chocolate + AAO |
|---|---|---|---|---|---|---|
| TFA (% DW) | 7.3 | 13.6 | 19.6 | 24.0 | 41.7 | 45.7 |
| C10:0 | 1.2 | 1.0 | 1.8 | 1.4 | — | — |

TABLE 29-continued

Fatty Acid Composition of Dairy-Containing Products
before and After Algal Anaplerotic Oil Addition

| | Yogurt Control | Yogurt + AAO | Ice Cream Control | Ice Cream + AAO | Chocolate Control | Chocolate + AAO |
|---|---|---|---|---|---|---|
| C12:0 | 2.7 | 1.7 | 2.9 | 2.4 | — | — |
| C13:0 | — | 0.7 | 0.1 | 0.4 | — | 0.1 |
| C14:0 | 11.7 | 6.7 | 11.0 | 9.1 | 0.1 | 0.2 |
| C14:1 | 0.8 | 0.5 | 0.8 | 0.6 | — | — |
| C15:0 | 1.3 | 22.1 | 1.2 | 10.1 | — | 4.4 |
| C16:0 | 35.8 | 22.5 | 35.5 | 30.0 | 26.7 | 24.9 |
| C16:1 | 1.8 | 1.1 | 1.7 | 1.5 | 0.3 | 0.3 |
| C17:0 | 0.8 | 5.4 | 0.7 | 2.6 | 0.2 | 1.2 |
| C17:1 | — | 0.2 | 0.3 | 0.2 | — | — |
| C18:0 | 14.0 | 7.5 | 14.1 | 11.3 | 35.6 | 32.2 |
| C18:1n9 | 26.0 | 14.2 | 25.3 | 20.3 | 32.5 | 29.7 |
| C18:2n6 | 3.2 | 1.8 | 3.8 | 3.1 | 3.1 | 2.8 |
| C18:3n3 | 0.7 | 0.4 | 0.5 | 0.4 | 0.2 | 0.2 |
| C18:3n6 | — | — | — | — | — | — |
| C19:0 IS | 22.4 | 11.5 | 8.2 | 6.5 | 3.8 | 2.7 |
| C20:0 | — | — | 0.2 | 0.1 | 1.1 | 1.0 |
| C20:1n9 | — | — | — | — | — | — |
| C20:2 | — | — | — | — | — | — |
| C20:3n3 | — | — | 0.2 | 0.2 | — | — |
| C20:3n6 | — | — | — | 0.2 | — | — |
| C20:4n6 | — | — | — | — | — | — |
| C20:5n3 EPA | — | 0.4 | — | 0.2 | 0.2 | 0.2 |
| C22:1n9 | — | — | — | — | — | — |
| C22:5n6 DPA | — | 2.0 | — | 0.9 | — | 0.4 |
| C22:6n3 DHA | — | 11.9 | — | 5.0 | — | 2.4 |
| C24:1 & C22:5n3 | — | — | — | — | — | — |
| OCFA (% TFA) | 2.2 | 28.2 | 1.9 | 13.1 | 0.2 | 5.8 |
| Serving size (g) | 113 | 113 | 89 | 89 | 35 | 35 |
| AAO per serving (g) | — | 1.5 | — | 1.9 | — | 2.1 |
| Fat Content (% WW) | 2.6 | 3.9 | 9.9 | 12.0 | 38.4 | 44.5 |

Table 30 below shows an example of the fatty acid composition of varying types of animal products such as salmon meat, turkey meat, and imitation eggs (e.g., made of mung bean protein isolate or any other suitable plant-based material). Specifically, as shown in the examples, OCFA comprised about 8.7% of the TFA in salmon meat; OCFA comprised about 29.3% of the TFA in turkey meat; and OCFA comprised about 13.7% of the TFA in poultry eggs. In some embodiments, after addition of microbial anaplerotic oil to animal products, the OCFA may comprise about 8-30% of TFA of the animal product. In other embodiments, the OCFA may comprise about 8-10% of the TFA of the animal product. In other embodiments, the OCFA may comprise about 10-15% of the TFA of the animal product. In other embodiments, the OCFA may comprise about 15-20% of the TFA of the animal product. In other embodiments, the OCFA may comprise about 20-25% of the TFA of the animal product. In other embodiments, the OCFA may comprise about 25-30% of the TFA of the animal product. It should be clearly understood that substantial benefit may still be derived from higher or lower rates of inclusion of OCFA in the animal products.

In this example, it should be clearly understood that the animal products or meat may be standard natural meat or plant-based substitute meat. Where the meat is a plant-based substitute meat, an amount of AAO or MAO may be added in order to match or exceed the amount of saturated OCFAs present in the standard naturally occurring meat counterpart. It should also be clearly understood that the word "meat" as used herein refers to any red meat, white meat, fish, and other seafood.

TABLE 30

Fatty Acid Composition of Animal Products before
and After Algal Anaplerotic Oil Addition

| | Salmon Control | Salmon + AAO | Turkey Control | Turkey + AAO | Eggs Control | Eggs + AAO |
|---|---|---|---|---|---|---|
| TFA (% DW) | 19.4 | 23.7 | 7.0 | 11.0 | 37.3 | 47.0 |
| C10:0 | — | — | — | — | — | — |
| C12:0 | — | 0.1 | — | — | — | — |
| C13:0 | — | 0.2 | — | 0.7 | — | 0.3 |
| C14:0 | 1.8 | 1.7 | 0.7 | 0.8 | — | 0.3 |
| C14:1 | — | — | — | — | — | — |
| C15:0 | 0.2 | 6.8 | — | 23.0 | — | 10.7 |
| C16:0 | 11.4 | 10.9 | 17.4 | 12.9 | 5.2 | 5.8 |
| C16:1 | 2.3 | 2.1 | 1.3 | 0.7 | 0.2 | 0.2 |
| C17:0 | 0.2 | 1.7 | 0.4 | 5.6 | 0.1 | 2.6 |
| C17:1 | 0.3 | 0.3 | — | — | 0.2 | 0.1 |
| C18:0 | 3.8 | 3.2 | 9.7 | 5.3 | 1.9 | 1.5 |

TABLE 30-continued

Fatty Acid Composition of Animal Products before and After Algal Anaplerotic Oil Addition

|  | Salmon Control | Salmon + AAO | Turkey Control | Turkey + AAO | Eggs Control | Eggs + AAO |
|---|---|---|---|---|---|---|
| C18:1n9 | 41.8 | 35.8 | 27.6 | 13.4 | 61.3 | 47.4 |
| C18:2n6 | 17.6 | 15.1 | 36.9 | 18.6 | 21.1 | 16.3 |
| C18:3n3 | 5.0 | 4.3 | 2.9 | 1.6 | 7.4 | 5.7 |
| C18:3n6 | 0.3 | 0.2 | — | — | — | — |
| C19:0 IS | 7.7 | 6.2 | 22.5 | 12.4 | 4.0 | 3.4 |
| C20:0 | 0.3 | 0.3 | — | — | 0.6 | 0.5 |
| C20:1n9 | 2.9 | 2.5 | — | — | 1.4 | 1.1 |
| C20:2 | 1.4 | 1.2 | — | — | — | — |
| C20:3n3 | 0.5 | 0.5 | 3.2 | 2.5 | — | — |
| C20:3n6 | 0.6 | 0.5 | — | — | — | — |
| C20:4n6 | 0.4 | 0.4 | — | — | — | — |
| C20:5n3 EPA | 3.1 | 2.8 | — | 0.4 | 0.4 | 0.4 |
| C22:1n9 | 0.3 | 0.2 | — | — | — | — |
| C22:5n6 DPA | — | 0.7 | — | 2.3 | — | 1.0 |
| C22:6n3 DHA | 4.4 | 7.3 | — | 12.3 | — | 5.8 |
| C24:1 & C22:5n3 | 1.5 | 1.3 | — | — | 0.2 | 0.2 |
| OCFA (% TFA) | 0.4 | 8.7 | 0.4 | 29.3 | 0.1 | 13.7 |
| Serving size (g) | 113 | 113 | 113 | 113 | 44 | 44 |
| AAO per serving (g) | — | 1.5 | — | 1.6 | — | 1.7 |
| Fat Content (% WW) | 5.2 | 6.5 | 1.3 | 2.7 | 11.0 | 14.9 |

Cyanocobalamin Affects Metabolism of Glucose and Propionate in Humans and Animals Animal feed may be prepared to increase the cyanocobalamin concentration therein to ensure that the chicken can assimilate the propionate that is produced from β-oxidation of odd chain fatty acids and therefore avoid propionic acidemia. The metabolism of propionate requires cyanocobalamin, which is a cofactor of methyl-malonyl-CoA mutase that produces succinyl-CoA. Succinyl-CoA enters the citric acid cycle and contributes to gluconeogenesis. The examples below also show how propionate metabolism links to glucose metabolism as well as the importance of cyanocobalamin to metabolize propionate.

Example 20

A demonstration was performed to illustrate the impact of cyanocobalamin on *Aurantiochytrium acetophilum* HS399 glucose metabolism. *Aurantiochytrium acetophilum* HS399 was cultivated in the presence and absence of cyanocobalamin. In this demonstration, four treatments were prepared with varying concentrations of propionate and cyanocobalamin (3 g/L/0.0003704, 3 g/L/0 μM, 9 g/L/0.0003704 and 9 g/L/0 μM). Respective Erlenmeyer flasks (250 mL) were inoculated (1% v/v) in triplicates with a 24 h old culture of *A. acetophilum* HS399 and incubated in an orbital shaker at 180 rpm and 27° C. The respective Erlenmeyer flasks contained 100 mL of a medium supplemented with (g/L): dextrose (100), ammonium acetate (4.6), NaCl (12.5), MgSO4 7H2O (2.5), KH2PO4 (0.5), KCl (0.5) and CaCl2 (0.1). This medium also contained trace element solution (5 ml/L) and vitamin solution (1 ml/L). The trace element solution contained (g/L): EDTA di-sodium salt (6), FeCl3 6H2O (0.29), H2BO3 (6.84), MnCl2 4H2O(0.86), ZnCl2 (0.06), NiSO4 6H2O (0.052), CuSO4 5H2O (0.002), Na2MoO4H2O (0.005). The vitamin solution contained (mg/L): thiamine (100) and biotin (0.5). All culture materials were autoclaved (121° C., 15 min) and media was filter sterilized before use. A propionate stock (200 g/L) was prepared using sodium propionate and was used to supplement the cultures the respective propionate concentration. Daily samples were collected to analyze the cell dry weight, residual glucose, culture pH, lipid and fatty acid composition of the cultures. Cell dry weights were analyzed by vacuum filtration (0.2 μm) and washed with a solution of ammonium bicarbonate. Residual glucose was analyzed using a colorimetric method based on glucose peroxidase activity. Biomass for lipid analysis was centrifuged and washed using purified water. The washed biomass was freeze dried. Total lipids were analyzed using the Folch method (AOAC 996.06) and the FAMES were analyzed by gas chromatography using nonadecanoic (C19:0) acid as an internal standard.

FIG. 51 is a graphical representation of example results 5100 illustrating growth and residual propionate in *A. acetophilum* HS399 cultures that are subject to propionic anaplerosis triggered by cyanocobalamin. In FIG. 51, the different letters (a, b) in respective time points indicate statistically significant differences according to this implementation ($p<0.05$). FIG. 52 is a graphical representation of example results 5200 illustrating residual glucose in *A. acetophilum* HS399 cultures subject to propionic anaplerosis triggered by cyanocobalamin. In FIG. 52, the different letters (e, f, g, h) in each time point indicate statistically significant differences according to a t-student test ($p<0.05$).

In this implementation, a culture can be fed 3 and 9 g/L of odd numbered propionic acid that is a product of the oxidation of longer chain fatty acids C15:0 and C17:0 in the presence or absence of cyanocobalamin (0 vs 0.37 μM) in shake flask cultures. As described above, OCFAs anaplerosis can merely take place in the presence of cyanocobalamin. In this implementation, the cell dry weight and residual propionate can be monitored, and residual glucose in the media can be analyzed. As an example, while the growth in the first 48 h may not be impacted by the cyanocobalamin, as illustrated by the results 5100 of FIG. 51, the residual glucose data indicates that glucose uptake rate may be significantly ($P<0.01$ t-student) lower in the cyanocobalamin-anaplerotic treatment, as illustrated in the results 5200 of FIG. 52. For example, these results indicate a link between OCFAs anaplerosis and glucose metabolism. Cell dry weight reached the same titers independently of the cyanocobalamin concentration.

Example 21

A demonstration was performed to illustrate the impact of cyanocobalamin on *Aurantiochytrium acetophilum* HS399 propionate metabolism. *Aurantiochytrium acetophilum* HS399 was cultivated in the presence and absence of cyanocobalamin. In this demonstration, two treatments were prepared with varying concentrations of cyanocobalamin (370 nM and 0 nM). Respective Erlenmeyer flasks (250 mL) were inoculated (1% v/v) in quintuplets with a 24 h old culture of *A. acetophilum* HS399 and incubated in an orbital shaker at 180 rpm and 27° C. The respective Erlenmeyer flasks contained 100 mL of a medium supplemented with (g/L): dextrose (100), ammonium acetate (4.6), NaCl (12.5), MgSO4 7H2O (2.5), KH2PO4 (0.5), KCl (0.5) and CaCl2 (0.1). This medium also contained trace element solution (5 ml/L) and vitamin solution (1 ml/L). The trace element solution contained (g/L): EDTA di-sodium salt (6), FeCl3 6H2O (0.29), H2BO3 (6.84), MnCl2 4H2O(0.86), ZnCl2 (0.06), NiSO4 6H2O (0.052), CuSO4 5H2O (0.002), Na2MoO4H2O (0.005). The vitamin solution contained (mg/L): thiamine (100) and biotin (0.5). All culture materials were autoclaved (121° C., 15 min) and media was filter sterilized before use. A propionate stock (200 g/L) was prepared using sodium propionate and was used to supplement the cultures with 16 g/L of propionate. Daily samples were collected to analyze the cell dry weight, residual glucose, culture pH, lipid and fatty acid composition of the cultures. Cell dry weights were analyzed by vacuum filtration (0.2 µm) and washed with a solution of ammonium bicarbonate. Residual glucose was analyzed using a colorimetric method based on glucose peroxidase activity. Biomass for lipid analysis was centrifuged and washed using purified water. The washed biomass was freeze dried. Total lipids were analyzed using the Folch method (AOAC 996.06) and the FAMES were analyzed by gas chromatography using nonadecanoic (C19:0) acid as an internal standard.

Figure 56:
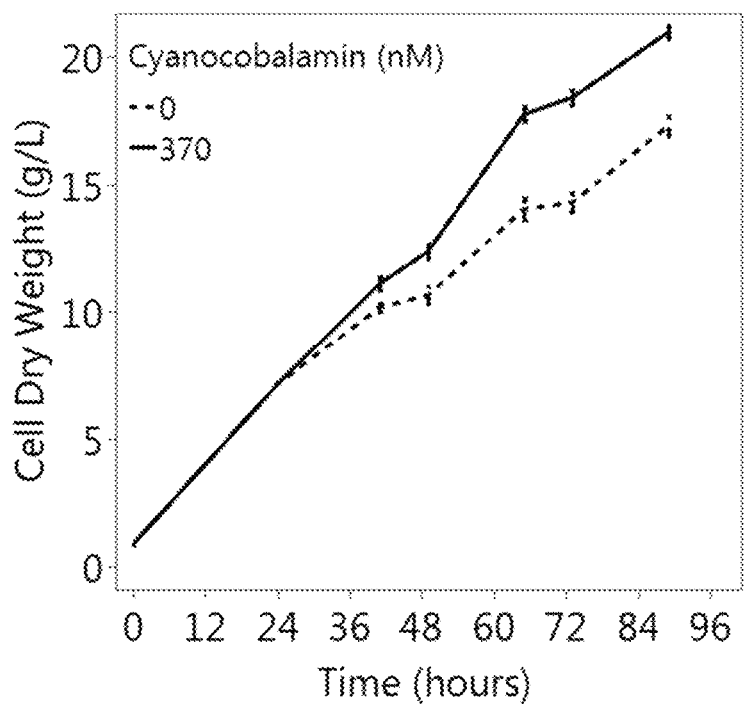
FIG. 56 is a graphical representation illustrating the growth of *Aurantiochytrium acetophilum* HS399 that has been subjected to propionic anaplerosis triggered by cyanocobalamin.
Figure 57:
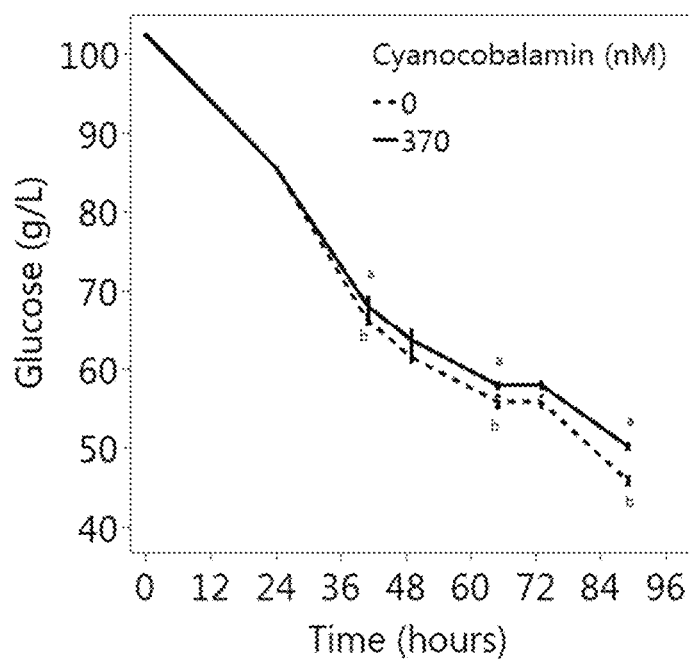
FIG. 57 is a graphical representation illustrating the residual glucose levels in an *Aurantiochytrium acetophilum* HS399 culture that has been subjected to propionic anaplerosis triggered by cyanocobalamin.
Figure 58:
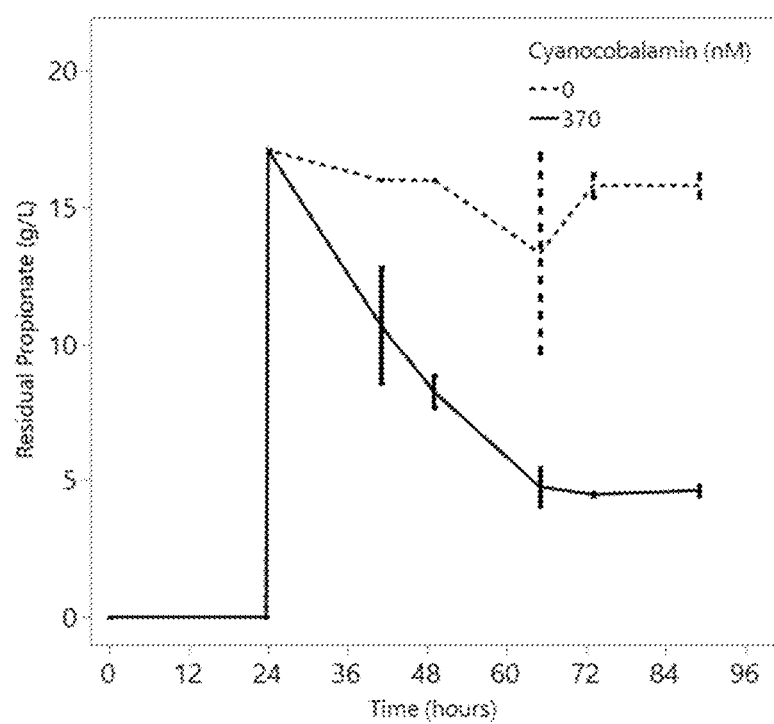
FIG. 58 is a graphical representation illustrating the residual propionate levels in an *Aurantiochytrium acetophilum* HS399 culture that has been subjected to propionic anaplerosis triggered by cyanocobalamin.

FIGS. 56, 57 and 58 are a graphical representation of example results illustrating growth, residual glucose and propionate in *A. acetophilum* HS399 cultures that are subject to propionic anaplerosis triggered by cyanocobalamin. In FIG. 57, the different letters (a, b) in respective time points indicate statistically significant differences according to this implementation (p<0.01). These figures show that human and non-human animals need to have a balanced diet which includes sufficient amounts of cyanocobalamin to ensure proper metabolism of propionate.

In this implementation, a culture can be fed 16 g/L of odd numbered propionic acid that is a product of the oxidation of longer chain fatty acids C15:0 and C17:0 in the presence or absence of cyanocobalamin (0 vs 370 nM) in shake flask cultures. As described above, OCFAs anaplerosis can merely take place in the presence of cyanocobalamin. In this implementation, the cell dry weight and residual propionate can be monitored, and residual glucose in the media can be analyzed. In this implementation, supplementation of a higher concentration of cyanocobalamin did show a positive difference in cell dry weight. The results shown in FIG. 57, the residual glucose data indicates that glucose uptake rate may be significantly (P<0.01 t-student) lower in the cyanocobalamin-anaplerotic treatment. For example, these results indicate a link between OCFAs anaplerosis and glucose metabolism. FIG. 58 shows that cultures deficient in cyanocobalamin couldn't oxidize propionate through the citric acid cycle, causing a chronical higher residual propionate in the culture.

While this disclosure describes anaplerotic oil production using the microalgae *A. acetophilum* HS399, and the yeast-fungi *Yarrowia lipolytica*, it should be appreciated that the method disclosed can be used with various other species of *Aurantiochytrium*, thraustochytrids, or other species of microorganisms including microalgae yeast, fungi and bacteria.

The term "microalgae" refers to microscopic single cell organisms such as microalgae, cyanobacteria, algae, diatoms, dinoflagellates, freshwater organisms, marine organisms, or other similar single cell organisms capable of growth in phototrophic, mixotrophic, or heterotrophic culture conditions. The term fungi refers to microscopic and macroscopic single cell organisms such us yeast and filamentous fungi.

In some embodiments, microalgae biomass, excreted products, or extracts may be sourced from multiple types of microalgae, to make a composition that is beneficial when applied to plants or soil. Non-limiting examples of microalgae that can be used in the compositions and methods of the claimed subject matter comprise microalgae in the classes: Eustigmatophyceae, Chlorophyceae, Prasinophyceae, Haptophyceae, Cyanidiophyceae, Prymnesiophyceae, Porphyridiophyceae, Labyrinthulomycetes, Trebouxiophyceae, Bacillariophyceae, and Cyanophyceae. The class Cyanidiophyceae includes species of *Galdieria*. The class Chlorophyceae includes species of *Chlorella, Haematococcus, Scenedesmus, Chlamydomonas*, and *Micractinium*. The class Prymnesiophyceae includes species of *Isochrysis* and *Pavlova*. The class Eustigmatophyceae includes species of *Nannochloropsis*. The class Porphyridiophyceae includes species of *Porphyridium*. The class Labyrinthulomycetes includes species of *Schizochytrium* and *Aurantiochytrium*. The class Prasinophyceae includes species of *Tetraselmis*. The class Trebouxiophyceae includes species of *Chlorella*. The class Bacillariophyceae includes species of *Phaeodactylum*. The class Cyanophyceae includes species of *Spirulina*.

Non-limiting examples of microalgae genus and species that can be used in the compositions and methods of the claimed subject matter include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Aurantiochytrium* sp., *Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomonas* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella sac-* charophila var. ellipsoidea, Chlorella salina, Chlorella simplex, Chlorella sorokiniana, Chlorella sp., Chlorella sphaerica, Chlorella stigmatophora, Chlorella vanniellii, Chlorella vulgaris, Chlorella vulgaris fo. tertia, Chlorella vulgaris var. autotrophica, Chlorella vulgaris var. viridis, Chlorella vulgaris var. vulgaris, Chlorella vulgaris var. vulgaris fo. tertia, Chlorella vulgaris var. vulgaris fo. viridis, Chlorella xanthella, Chlorella zofingiensis, Chlorella trebouxioides, Chlorella vulgaris, Chlorococcum infusionum, Chlorococcum sp., Chlorogonium, Chroomonas sp., Chrysosphaera sp., Cricosphaera sp., Crypthecodinium cohnii, Cryptomonas sp., Cyclotella cryptica, Cyclotella meneghiniana, Cyclotella sp., Dunaliella sp., Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera sp., Ellipsoidon sp., Euglena spp., Franceia sp., Fragilaria crotonensis, Fragilaria sp., Galdieria sp., Gleocapsa sp., Gloeothamnion sp., Haematococcus pluvialis, Hymenomonas sp., Isochrysis aff. galbana, Isochrysis galbana, Lepocinclis, Micractinium, Monoraphidium minutum, Monoraphidium sp., Nannochloris sp., Nannochloropsis salina, Nannochloropsis sp., Navicula acceptata, Navicula biskanterae, Navicula pseudotenelloides, Navicula pelliculosa, Navicula saprophila, Navicula sp., Nephrochloris sp., Nephroselmis sp., Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia sp., Ochromonas sp., Oocystis parva, Oocystis pusilla, Oocystis sp., Oscillatoria limnetica, Oscillatoria sp., Oscillatoria subbrevis, Parachlorella kessleri, Pascheria acidophila, Pavlova sp., Phaeodactylum tricomutum, Phagus, Phormidium, Platymonas sp., Pleurochrysis camerae, Pleurochrysis dentate, Pleurochrysis sp., Porphyridium sp., Prototheca wickerhamii, Prototheca stagnora, Prototheca portoricensis, Prototheca moriformis, Prototheca zopfii, Pseudochlorella aquatica, Pyramimonas sp., Pyrobotrys, Rhodococcus opacus, Sarcinoid chrysophyte, Scenedesmus armatus, Schizochytrium, Spirogyra, Spirulina platensis, Stichococcus sp., Synechococcus sp., Synechocystisf, Tagetes erecta, Tagetes patula, Tetraedron, Tetraselmis sp., Tetraselmis suecica, Thalassiosira weissflogii, and Viridiella fridericiana.

Taxonomic classification has been in flux for organisms in the genus *Schizochytrium*. Some organisms previously classified as *Schizochytrium* have been reclassified as *Aurantiochytrium*, *Thraustochytrium*, or *Oblongichytrium*. See Yokoyama et al. Taxonomic rearrangement of the genus *Schizochytrium* sensu lato based on morphology, chemotaxonomic characteristics, and 18S rRNA gene phylogeny (Thrausochytriaceae, Labyrinthulomycetes): emendation for *Schizochytrium* and erection of *Aurantiochytrium* and *Oblongichytrium* gen. nov. Mycoscience (2007) 48:199-211. Those of skill in the art will recognize that *Schizochytrium*, *Aurantiochytrium*, *Thraustochytrium*, and *Oblongichytrium* appear closely related in many taxonomic classification trees for microalgae, and strains and species may be re-classified from time to time. Thus, for references throughout the instant specification for *Schizochytrium*, it is recognized that microalgae strains in related taxonomic classifications with similar characteristics to *Schizochytrium*, such as *Aurantiochytrium*, would reasonably be expected to produce similar results.

In some embodiments, the microalgae may be cultured in phototrophic, mixotrophic, or heterotrophic culture conditions in an aqueous culture medium. The organic carbon sources suitable for growing microalgae mixotrophically or heterotrophically may comprise: acetate, acetic acid, ammonium linoleate, arabinose, arginine, aspartic acid, butyric acid, cellulose, citric acid, ethanol, fructose, fatty acids, galactose, glucose, glycerol, glycine, lactic acid, lactose, maleic acid, maltose, mannose, methanol, molasses, peptone, plant based hydrolysate, proline, propionic acid, ribose, saccharose, partial or complete hydrolysates of starch, sucrose, tartaric, TCA-cycle organic acids, thin stillage, urea, industrial waste solutions, yeast extract, and combinations thereof. The organic carbon source may comprise any single source, combination of sources, and dilutions of single sources or combinations of sources. In some embodiments, the microalgae may be cultured in axenic conditions. In some embodiments, the microalgae may be cultured in non-axenic conditions.

In one non-limiting embodiment, the microalgae of the culture in an aqueous culture medium may comprise *Chlorella* sp. cultured in mixotrophic conditions comprising a culture medium primary comprised of water with trace nutrients (e.g., nitrates, phosphates, vitamins, metals found in BG-11 recipe [available from UTEX The Culture Collection of Algae at the University of Texas at Austin, Austin, Tex.]), light as an energy source for photosynthesis, and organic carbon (e.g., acetate, acetic acid) as both an energy source and a source of carbon. In some embodiments, the culture media may comprise BG-11 media or a media derived from BG-11 culture media (e.g., in which additional component(s) are added to the media and/or one or more elements of the media is increased by 5%, 10%, 15%, 20%, 25%, 33%, 50%, or more over unmodified BG-11 media). In some embodiments, the *Chlorella* may be cultured in non-axenic mixotrophic conditions in the presence of contaminating organisms, such as but not limited to bacteria. Additional detail on methods of culturing such microalgae in non-axenic mixotrophic conditions may be found in WO2014/074769A2 (Ganuza et al.), hereby incorporated by reference.

In some embodiments, by artificially controlling aspects of the microalgae culturing process such as the organic carbon feed (e.g., acetic acid, acetate), oxygen levels, pH, and light, the culturing process differs from the culturing process that microalgae experiences in nature. In addition to controlling various aspects of the culturing process, intervention by human operators or automated systems occurs during the non-axenic mixotrophic culturing of microalgae through contamination control methods to prevent the microalgae from being overrun and outcompeted by contaminating organisms (e.g., fungi, bacteria). Contamination control methods for microalgae cultures are known in the art and such suitable contamination control methods for non-axenic mixotrophic microalgae cultures are disclosed in WO2014/074769A2 (Ganuza et al.), hereby incorporated by reference. By intervening in the microalgae culturing process, the impact of the contaminating microorganisms can be mitigated by suppressing the proliferation of containing organism populations and the effect on the microalgal cells (e.g., lysing, infection, death, clumping). Thus, through artificial control of aspects of the culturing process and intervening in the culturing process with contamination control methods, the microalgae culture produced as a whole and used in the described inventive compositions differs from the culture that results from a microalgae culturing process that occurs in nature.

In some embodiments, during the culturing process the microalgae culture may also comprise cell debris and compounds excreted from the microalgae cells into the culture medium. The output of the microalgae culturing process provides the active ingredient for composition that is applied to plants for improving yield and quality without separate addition to or supplementation of the composition with other active ingredients not found in the mixotrophic microalgae whole cells and accompanying culture medium from the culturing process such as, but not limited to: microalgae extracts, macroalgae, macroalgae extracts, liquid fertilizers, granular fertilizers, mineral complexes (e.g., calcium, sodium, zinc, manganese, cobalt, silicon), fungi, bacteria, nematodes, protozoa, digestate solids, chemicals (e.g., ethanolamine, borax, boric acid), humic acid, nitrogen and nitrogen derivatives, phosphorus rock, pesticides, herbicides, insecticides, enzymes, plant fiber (e.g., coconut fiber).

While OCFA production increase has been described herein in terms of algae, fungus yeast, and other microbial, the techniques and systems described herein may not be limited merely to these types of organisms. In one aspect, there are some plant sources that naturally contain OCFA, specifically C15 and C17, which could therefore be genetically modified to increase production of these OCFAs. That is, for example, much like with the production of OCFAs in algae, fungus and yeast, the plant genetic code may be modified to increase the already naturally occurring OCFA. As an example, the genetic code that increases OCFA production in microorganisms may be identified, and, using gene splicing techniques, such as CRISPR-type techniques, the OCFA code may be inserted into certain plants. Additionally, genetic trait selection may be undertaken to identify and breed plants that express improved OCFA production, resulting in a plant that has higher OCFA production. Also, a combination of genetic code manipulation and trait selection may be used to produce plants with improved OCFA production.

In addition to microalgae, some plants are able to serve as additional natural sources of long odd chain fatty acids. As shown in FIG. 55, as Table 26, there are several plants that naturally contain C15:0 fatty acid, including, but not limited to: grape, *silybum marianum* (a thistle), wheat germ, and rapeseed. Additionally, several plants naturally contain C17:0 fatty acid, including, but not limited to: safflower, grape, *silybum marianum*, hemp, sunflower, wheatgerm, pumpkin seed, almond, rapeseed, and peanut. Typically, these plants merely produce trace levels of C15:0 and C17:0.

Higher plants do not typically produce odd chain fatty acids (OCFAs) at commercially significant levels, however several plants (e.g., see plants in Table 16) present a metabolic pathway capable of synthetizing OCFAs. For example, the alpha oxidation pathway is a catabolic route typically associated with the degradation of β-methyl branched fatty acids (see ref 5—Buchhaupt et al., 2014). The enzyme α-oxygenase (αDOX), a heme protein, introduces an oxygen molecule to the α-C of a fatty acid, leading to a decarboxylation. An aldehyde dehydrogenase enzyme completes the oxidation of the resulting aldehyde to the corresponding fatty acid with one less carbon atom. This pathway eliminates the methyl group of the branched fatty acids, resulting in a straight chain (even) fatty acid, but it could also eliminate the methyl group of an even chain fatty acid, which would result in the production of OCFAs (see ref. 8—Takahashi et al., 1992). This pathway has been described in pea plants (see ref. 7—Shine and Stumpf, 1974), tobacco leaves, cucumber, potato (see ref 6—Hamberg et al., 1999), and could potentially be overexpressed in other plants, including oleaginous crops (e.g., soy, canola, flax, sunflower etc.), and directed to the production of OCFAs in plants. OCFAs production in oleaginous crops would benefit from the productivities and infrastructure available for such agricultural commodities.

All references, including publications, patent applications, and patents, cited herein, are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All provided ranges of values are intended to include the end points of the ranges, as well as values between the end points.

The citation and incorporation of patent documents herein is done for convenience only and does not reflect any view of the validity, patentability, and/or enforceability of such patent documents.

The inventive concepts described herein include all modifications and equivalents of the subject matter recited in the claims and/or aspects appended hereto as permitted by applicable law.

REFERENCES

1. Weitkunat, K., Schumann, S., Nickel, D., Hornemann, S., Petzke, K. J., Schulze, M. B., . . . Klaus, S. (2017). Odd-chain fatty acids as a biomarker for dietary fiber intake: a novel pathway for endogenous production from propionate. The American Journal of Clinical Nutrition, 105(6), ajcn 152702. https://doi.org/10.3945/ajcn.117.152702.
2. Rezanka, T., & Sigler, K. (2009). Odd-numbered very-long-chain fatty acids from the microbial, animal and plant kingdoms. Progress in Lipid Research, 48(3-4), 206-238. https://doi.org/10.1016/j.plipres.2009.03.003.
3. Chaung, K.-C., Chu, C.-Y., Su, Y.-M., & Chen, Y.-M. (2012). Effect of culture conditions on growth, lipid content, and fatty acid composition of *Aurantiochytrium mangrovei* strain BL10. AMB Express, 2(1), 42. https://doi.org/10.1186/2191-0855-2-42.
4. Fan K W, Chen F, Jones E B, Vrijmoed L L. Eicosapentaenoic and docosahexaenoic acids production by and okara-utilizing potential of thraustochytrids. J Ind Microbiol Biotechnol. 2001; 27(June):199-202. doi:10.1038/sj.jim.7000169.
5. Zhu, L., Zhang, X., Ji, L., Song, X., & Kuang, C. (2007). Changes of lipid content and fatty acid composition of *Schizochytrium limacinum* in response to different temperatures and salinities. Process Biochemistry, 42(2), 210-214. https://doi.org/10.1016/j.procbio.2006.08.002.
6. Buchhaupt, M., Kähne, F., Etschmann, M. M. W. & Schrader, J. Chapter 37—Biotechnological Production of Fatty Aldehydes. Flavour Science (Elsevier Inc., 2014). doi:10.1016/B978-0-12-398549-1.00037-4.

7. Hamberg, M., Sanz, a & Castresana, C. α-Oxidation of fatty acids in higher plants. J. Biol. Chem. 274, 24503 (1999).
8. Shine, W. E. & Stumpf, P. K. Fat Metabolism in Higher Plants Recent Studies on Plant a-Oxidation Systems. Arch. Biochem. Biophys. 147-157 (1974).
9. Takahashi, T., Takahashi, H., Takeda, H. & Shichiri, M. Alpha-oxidation of fatty acids in fasted or diabetic rats. Diabetes Res. Clin. Pract. 16, 103-108 (1992).
10. Park Y K, Dulermo T, Amaro R L, Nicaud J M. Optimization of odd chain fatty acid production by *Yarrowia lipolytica*. Biotechnol Biofuels. 2018; 11(158):1-12. doi:

Although a particular feature of the disclosed techniques and systems may have been disclosed with respect to only one of several implementations, such feature may be combined with one or more other features of the other implementations as may be desired and advantageous for any given or particular application. Also, to the extent that the terms "including", "includes", "having", "has", "with", or variants thereof are used in the detailed description and/or in the claims, such terms are intended to be inclusive in a manner similar to the term "comprising."

This written description uses examples to disclose the claimed subject matter, including the best mode, and also to enable one of ordinary skill in the art to practice the claimed subject matter, including making and using any devices or systems and performing any incorporated methods. The patentable scope of the inventive concepts, described herein, are defined by the claims, and may include other examples that occur to those skilled in the art. Such other examples are intended to be within the scope of the claims if they have structural elements that are not different from the literal language of the claims, or if they include equivalent structural elements with insubstantial differences from the literal language of the claims.

In the specification and claims, reference will be made to "animals." As used herein, "animals" refers to members of the kingdom Animalia, which includes humans and non-human animals (e.g., poultry, fish, etc.).

In the specification and claims, reference will be made to "food." As used herein, "food" refers to consumable products, in solid form (e.g., fish meat, poultry meat, yogurt, eggs, etc.), liquid (e.g., milk, juice), or a mixture of solid and liquid forms (e.g., ice cream). The word "food" also refers generically to either standard naturally occurring foods or plant-based substitute foods.

In the specification and claims, reference will be made to a number of terms that have the following meanings. The singular forms "a", "an" and "the" include plural referents unless the context clearly dictates otherwise. Approximating language, as used herein throughout the specification and claims, may be applied to modify a quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Moreover, unless specifically stated otherwise, a use of the terms "first," "second," etc., do not denote an order or importance, but rather the terms "first," "second," etc., are used to distinguish one element from another.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

The best mode for carrying out the claimed subject matter has been described for purposes of illustrating the best mode known to the applicant at the time and enable one of ordinary skill in the art to practice the claimed subject matter, including making and using devices or systems and performing incorporated methods. The examples are illustrative only and not meant to limit the claimed subject matter, as measured by the scope and merit of the claims. The claimed subject matter has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof. The patentable scope of the inventive concepts, described herein, are defined by the claims, and may include other examples that occur to one of ordinary skill in the art. Such other examples are intended to be within the scope of the claims if they have structural elements that do not differentiate from the literal language of the claims, or if they include equivalent structural elements with insubstantial differences from the literal language of the claims.

What is claimed is:

1. A method of incorporating saturated odd-chain fatty acids (OCFA) into food for human and non-human animal consumption, the method comprising:
   replacing saturated fat of the food with microbial anaplerotic oil comprising the OCFA.

2. The method of claim 1, wherein replacing the saturated fat comprises:
   (a) identifying a unit amount of the saturated fat present in the food;
   (b) determining an amount of the saturated fat for removal from the food;
   (c) determining an amount of the microbial anaplerotic oil to incorporate into the food to replace the saturated fat to be removed from the food,
   wherein determining the amount of the microbial anaplerotic oil comprises:
   (i) identifying an amount of the OCFA present in the microbial anaplerotic oil as a percent of the microbial anaplerotic oil; and
   (ii) determining the amount of the microbial anaplerotic oil to incorporate into the food based on the percent identified in step (c) (i) and the amount of the saturated fat to be removed from the food;
   (d) removing the determined amount of the saturated fat from the food; and
   (e) adding the determined amount of the microbial anaplerotic oil to the food.

3. The method of claim 2, wherein the saturated fat is removed by a process selected from the group consisting of separation with a solvent, separation via filtration, and molecular distillation.

4. The method of claim 1, wherein the saturated fat comprises even-chain fatty acids (ECFA).

5. The method of claim 4, wherein the ECFA comprise tetradecanoic acid (C14:0), hexadecenoic acid (C16:0), octadecanoic acid (C18:0), or a combination thereof.

6. The method of claim 1, wherein the OCFA comprise tridecanoic acid (C13:0), pentadecanoic acid (C15:0), heptadecanoic acid (C17:0), or a combination thereof.

7. The method of claim 1, wherein the microbial anaplerotic oil further comprises docosahexaenoic acid (DHA).

8. The method of claim 1, wherein the microbial anaplerotic oil further comprises eicosapentaenoic acid (EPA).

9. The method of claim 1, wherein the food is a dairy product.

10. The method of claim 9, wherein the dairy product is selected from the group consisting of milk, cheese, cream, yogurt, butter, and powder milk.

11. The method of claim 1, wherein the food is an infant formula.

12. The method of claim 1, wherein the microbial anaplerotic oil is derived from a microorganism from the class Labyrinthulomycetes.

13. The method of claim 12, wherein the microorganism is a thraustochytrid.

14. A method of incorporating saturated odd-chain fatty acids (OCFA) into food for human and non-human animal consumption, the method comprising: identifying a target amount of the OCFA for incorporation into the food; and adding an amount of microbial anaplerotic oil containing the target amount of the OCFA to the food.

15. The method of claim 14, wherein the OCFA comprise tridecanoic acid (C13:0), pentadecanoic acid (C15:0), heptadecanoic acid (C17:0), or a combination thereof.

16. The method of claim 14, wherein the food is a naturally occurring food.

17. The method of claim 14, wherein the food is a plant-based food.

18. The method of claim 17, wherein the food is a substitute for a naturally occurring food, wherein the target amount of the OCFA is equal to an amount of the OCFA in the naturally occurring food.

19. The method of claim 17, wherein the food is a substitute for a naturally occurring food, wherein the target amount of the OCFA exceeds an amount of the OCFA in the naturally occurring food.

20. The method of claim 14, wherein the target amount of the OCFA is a targeted daily amount of the OCFA.

* * * * *